US009347871B2

(12) United States Patent
Fujinuma et al.

(10) Patent No.: US 9,347,871 B2
(45) Date of Patent: May 24, 2016

(54) LASER SCANNING TYPE OBSERVATION APPARATUS HAVING A DELAY CIRCUIT UNIT, A MULTI-STAGE DELAY SETTING UNIT AND A DECISION UNIT

(71) Applicant: OLYMPUS CORPORATION, Tokyo (JP)

(72) Inventors: Ken Fujinuma, Tokyo (JP); Shintaro Takahashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 133 days.

(21) Appl. No.: 14/458,474

(22) Filed: Aug. 13, 2014

(65) Prior Publication Data

US 2015/0028193 A1 Jan. 29, 2015

Related U.S. Application Data

(63) Continuation of application No. PCT/JP2013/053573, filed on Feb. 14, 2013.

(30) Foreign Application Priority Data

| Feb. 15, 2012 | (JP) | 2012-030871 |
| Jul. 18, 2012 | (JP) | 2012-159912 |
| Jul. 18, 2012 | (JP) | 2012-159913 |
| Jul. 18, 2012 | (JP) | 2012-159914 |
| Nov. 19, 2012 | (JP) | 2012-253378 |

(51) Int. Cl.
*G02B 21/00* (2006.01)
*G01N 21/17* (2006.01)
(Continued)

(52) U.S. Cl.
CPC . *G01N 21/17* (2013.01); *G01J 1/44* (2013.01); *G02B 21/002* (2013.01);
(Continued)

(58) Field of Classification Search
CPC .. G02B 21/002; G01J 1/44; G01N 2201/0697
USPC .......... 250/201.3, 214 R, 208.1, 235; 356/73, 356/318, 445, 446; 359/201, 368, 385–389, 359/393
See application file for complete search history.

(56) References Cited

U.S. PATENT DOCUMENTS

| 6,608,717 B1 | 8/2003 | Medford et al. | |
| 6,717,723 B2 * | 4/2004 | Arai | G02B 21/002 359/202.1 |

(Continued)

FOREIGN PATENT DOCUMENTS

| JP | 2003-043369 A | 2/2003 |
| JP | 2005-049864 A | 2/2005 |

(Continued)

OTHER PUBLICATIONS

Extended Supplementary European Search Report dated Jun. 22, 2015 from related European Application No. 13 74 8538.9.
(Continued)

*Primary Examiner* — Que T Le
(74) *Attorney, Agent, or Firm* — Scully, Scott, Murphy & Presser, P.C.

(57) ABSTRACT

A laser scanning type observation apparatus includes a pulsed-laser oscillation means irradiating pulsed laser to an object, a detector receiving light from the object to output a detection signal, a means detecting pulsed-laser oscillation to output a synchronous signal, a circuit delaying the synchronous signal for an optional amount of time to output a trigger signal, a means sampling the detection signal in synchronization with the trigger signal, a memory storing the sampled detection signal, a setting unit capable of setting delay time for delaying the synchronous signal in two or more stages within one period of the synchronous signal, and a decision unit determining an optimum delay stage for image formation using data on intensities of the detection signal at the respective delay stages, wherein the setting means fixes delay time for delaying the synchronous signal at delay time corresponding to the delay stage determined by the decision unit.

10 Claims, 32 Drawing Sheets

(51) Int. Cl.
*G02B 23/24* (2006.01)
*G02B 21/16* (2006.01)
*G01J 1/44* (2006.01)
*G01J 1/42* (2006.01)

(52) U.S. Cl.
CPC ........... *G02B 21/0084* (2013.01); *G02B 21/16* (2013.01); *G02B 23/24* (2013.01); *G01J 2001/4242* (2013.01); *G01N 2201/0697* (2013.01); *G01N 2201/06113* (2013.01)

(56) References Cited

U.S. PATENT DOCUMENTS

| | | |
|---|---|---|
| 2001/0015411 A1 | 8/2001 | Ohdaira et al. |
| 2011/0149290 A1 | 6/2011 | Schulte et al. |

FOREIGN PATENT DOCUMENTS

| | | |
|---|---|---|
| JP | 2007-102235 A | 4/2007 |
| JP | 2007-264664 A | 10/2007 |
| JP | 4407423 B2 | 2/2010 |
| JP | 4667571 B2 | 4/2011 |
| WO | 2011/052248 A1 | 5/2011 |

OTHER PUBLICATIONS

Gahlaut, N., and Miller, L.W., "Time-Resolved Micropsy for Imaging Lanthanide Luminescence in Living Cells", Cytometry Part A, Sep. 7, 2010, vol. 77A, No. 12, pp. 1113-1125.

Periasamy, A., et al., "Time-resolved fluorescence lifetime imaging microscopy using a picosecond pulsed tunable dye laser system", Review of Scientific Instruments, Oct. 1, 1996, vol. 67, No. 10, pp. 3722-3731.

Yu, W., et al., "Flourescence Lifetime Imaging: New Microscopy Technologies", Emerging Tools for Single-Cell Analysis: Advances in Optical Measurement Technologies, Cytometric Cellular Analysis, Jan. 1, 2000, pp. 139-173.

International Search Report dated May 14, 2013 issued in PCT/JP2013/053573.

English Abstract of JP 2006-053096 A, dated Feb. 23, 2006.
English Abstract of JP 2001-159734 A, dated Jun. 12, 2001.

* cited by examiner

LIGHT OF PULSED LASER

MONITOR SIGNAL OF LASER

MONITOR SIGNAL AFTER PASSING THROUGH HIGH MAGNIFICATION AMPLIFIER AND FILTER

MONITOR SIGNAL AFTER PASSING THROUGH CLOCK DEVICE

FIG.30

$\div 2 \rightarrow \dfrac{1}{2}$ $\div 3 \rightarrow \dfrac{0}{2}+\dfrac{1}{2^2}+\dfrac{0}{2^3}+\dfrac{1}{2^4}+\dfrac{0}{2^5}+\dfrac{1}{2^6}+\dfrac{0}{2^7}+\dfrac{1}{2^8}+\dfrac{0}{2^9}+\dfrac{1}{2^{10}}+\dfrac{0}{2^{11}}+\dfrac{1}{2^{12}}$ $\div 4 \rightarrow \dfrac{0}{2}+\dfrac{1}{2^2}$ $\div 5 \rightarrow \dfrac{0}{2}+\dfrac{0}{2^2}+\dfrac{1}{2^3}+\dfrac{1}{2^4}+\dfrac{0}{2^5}+\dfrac{0}{2^6}+\dfrac{1}{2^7}+\dfrac{1}{2^8}+\dfrac{0}{2^9}+\dfrac{0}{2^{10}}+\dfrac{1}{2^{11}}+\dfrac{1}{2^{12}}$ $\div 6 \rightarrow \dfrac{0}{2}+\dfrac{0}{2^2}+\dfrac{1}{2^3}+\dfrac{0}{2^4}+\dfrac{1}{2^5}+\dfrac{0}{2^6}+\dfrac{1}{2^7}+\dfrac{0}{2^8}+\dfrac{1}{2^9}+\dfrac{0}{2^{10}}+\dfrac{1}{2^{11}}+\dfrac{0}{2^{12}}$ $\div 7 \rightarrow \dfrac{0}{2}+\dfrac{0}{2^2}+\dfrac{1}{2^3}+\dfrac{0}{2^4}+\dfrac{0}{2^5}+\dfrac{1}{2^6}+\dfrac{0}{2^7}+\dfrac{0}{2^8}+\dfrac{1}{2^9}+\dfrac{0}{2^{10}}+\dfrac{0}{2^{11}}+\dfrac{1}{2^{12}}$ $\div 8 \rightarrow \dfrac{0}{2}+\dfrac{0}{2^2}+\dfrac{1}{2^3}$ $\div 9 \rightarrow \dfrac{0}{2}+\dfrac{0}{2^2}+\dfrac{0}{2^3}+\dfrac{1}{2^4}+\dfrac{1}{2^5}+\dfrac{1}{2^6}+\dfrac{0}{2^7}+\dfrac{0}{2^8}+\dfrac{0}{2^9}+\dfrac{1}{2^{10}}+\dfrac{1}{2^{11}}+\dfrac{1}{2^{12}}$ $\div 10 \rightarrow \dfrac{0}{2}+\dfrac{0}{2^2}+\dfrac{0}{2^3}+\dfrac{1}{2^4}+\dfrac{1}{2^5}+\dfrac{0}{2^6}+\dfrac{0}{2^7}+\dfrac{1}{2^8}+\dfrac{1}{2^9}+\dfrac{0}{2^{10}}+\dfrac{0}{2^{11}}+\dfrac{1}{2^{12}}$ $\div 11 \rightarrow \dfrac{0}{2}+\dfrac{0}{2^2}+\dfrac{0}{2^3}+\dfrac{1}{2^4}+\dfrac{0}{2^5}+\dfrac{1}{2^6}+\dfrac{1}{2^7}+\dfrac{1}{2^8}+\dfrac{0}{2^9}+\dfrac{1}{2^{10}}+\dfrac{0}{2^{11}}+\dfrac{0}{2^{12}}$ $\div 12 \rightarrow \dfrac{0}{2}+\dfrac{0}{2^2}+\dfrac{0}{2^3}+\dfrac{1}{2^4}+\dfrac{0}{2^5}+\dfrac{1}{2^6}+\dfrac{0}{2^7}+\dfrac{1}{2^8}+\dfrac{0}{2^9}+\dfrac{1}{2^{10}}+\dfrac{0}{2^{11}}+\dfrac{1}{2^{12}}$ $\div 13 \rightarrow \dfrac{0}{2}+\dfrac{0}{2^2}+\dfrac{0}{2^3}+\dfrac{1}{2^4}+\dfrac{0}{2^5}+\dfrac{0}{2^6}+\dfrac{1}{2^7}+\dfrac{1}{2^8}+\dfrac{1}{2^9}+\dfrac{0}{2^{10}}+\dfrac{1}{2^{11}}+\dfrac{1}{2^{12}}$ $\div 14 \rightarrow \dfrac{0}{2}+\dfrac{0}{2^2}+\dfrac{0}{2^3}+\dfrac{1}{2^4}+\dfrac{0}{2^5}+\dfrac{0}{2^6}+\dfrac{1}{2^7}+\dfrac{0}{2^8}+\dfrac{0}{2^9}+\dfrac{1}{2^{10}}+\dfrac{0}{2^{11}}+\dfrac{0}{2^{12}}$ $\div 15 \rightarrow \dfrac{0}{2}+\dfrac{0}{2^2}+\dfrac{0}{2^3}+\dfrac{1}{2^4}+\dfrac{0}{2^5}+\dfrac{0}{2^6}+\dfrac{0}{2^7}+\dfrac{1}{2^8}+\dfrac{0}{2^9}+\dfrac{0}{2^{10}}+\dfrac{0}{2^{11}}+\dfrac{1}{2^{12}}$ $\div 16 \rightarrow \dfrac{0}{2}+\dfrac{0}{2^2}+\dfrac{0}{2^3}+\dfrac{1}{2^4}$

FIG.31A $\frac{1}{2}$ → SHIFT BY 1 BIT → S(1)

$\frac{1}{2^2}$ → SHIFT BY 2 BITS → S(2)

$\frac{1}{2^3}$ → SHIFT BY 3 BITS → S(3)

$\frac{1}{2^4}$ → SHIFT BY 4 BITS → S(4)

$\frac{1}{2^5}$ → SHIFT BY 5 BITS → S(5)

$\frac{1}{2^6}$ → SHIFT BY 6 BITS → S(6)

$\frac{1}{2^7}$ → SHIFT BY 7 BITS → S(7)

$\frac{1}{2^8}$ → SHIFT BY 8 BITS → S(8)

$\frac{1}{2^9}$ → SHIFT BY 9 BITS → S(9)

$\frac{1}{2^{10}}$ → SHIFT BY 10 BITS → S(10)

$\frac{1}{2^{11}}$ → SHIFT BY 11 BITS → S(11)

$\frac{1}{2^{12}}$ → SHIFT BY 12 BITS → S(12)

FIG.31B

IN THE CASE WHERE INPUT SIGNAL IS 13 BIT SIGNAL AND DIVISORS ARE 2 TO 16

```
÷2  → S(1)
÷3  → S(2)+S(4)+S(6)+S(8)+S(10)+S(12)
÷4  → S(2)
÷5  → S(3)+S(4)+S(7)+S(8)+S(11)+S(12)
÷6  → S(3)+S(5)+S(7)+S(9)+S(11)
÷7  → S(3)+S(6)+S(9)+S(12)
÷8  → S(3)
÷9  → S(4)+S(5)+S(6)+S(10)+S(11)+S(12)
÷10 → S(4)+S(5)+S(8)+S(9)+S(12)
÷11 → S(4)+S(6)+S(7)+S(8)+S(10)
÷12 → S(4)+S(6)+S(8)+S(10)+S(12)
÷13 → S(4)+S(7)+S(8)+S(9)+S(11)+S(12)
÷14 → S(4)+S(7)+S(10)
÷15 → S(4)+S(8)+S(12)
÷16 → S(4)
```

LASER SCANNING TYPE OBSERVATION APPARATUS HAVING A DELAY CIRCUIT UNIT, A MULTI-STAGE DELAY SETTING UNIT AND A DECISION UNIT

This application claims benefits of Japanese Patent Applications No. 2012-030871 filed in Japan on Feb. 15, 2012, Japanese Patent Applications No. 2012-159912 filed in Japan on Jul. 18, 2012, Japanese Patent Applications No. 2012-159913 filed in Japan on Jul. 18, 2012, Japanese Patent Applications No. 2012-159914 filed in Japan on Jul. 18, 2012, and Japanese Patent Applications No. 2012-253378 filed in Japan on Nov. 19, 2012, the contents of which are hereby incorporated by this reference.

BACKGROUND OF THE INVENTION

1. Field of the Invention

This invention relates to a laser scanning type observation apparatus, such as laser scanning microscope and laser scanning endoscope, in which a pulsed laser is irradiated to a test object and then detection signals acquired by receiving light from the test object are sampled.

2. Description of Related Art

In general, as shown in FIG. 1 for example, a laser scanning microscope is configured to include: a light source 51 generating laser oscillation; a half mirror 52 splitting a laser beam from the light source 51 and splitting light from a test object 59; a galvanometer mirror 53 performing laser beam scanning in the X-direction and in the Y-direction; an objective lens 54 irradiating the laser beam to the test object 59; a pinhole 55 eliminating scattered light or the like from the light traveling from the test object 59 to extract only light traveling from a focal position; a light-receiving device 56 receiving the light that has passed through the pinhole 55; and an image-processing unit 57 to which analog electrical signals generated by photoelectric conversion by the light-receiving device 56 are supplied. The image-processing unit 57 converts the supplied analog signals into digital signals with a sampling clock optionally determined by an independent oscillator or the like, and then the converted digital signals are stored in a memory that is not shown in the drawings. And then, an image which is made to synchronize with a scan with the laser beam is formed with the digital signals stored in the memory, and the formed image is displayed on a monitor display 58.

Continuous wave lasers are commonly used for laser scanning microscopes. However, laser beams with various wavelengths have been used in recent years because of diversification of test objects for research, and laser beams are often generated also by causing pulse oscillation with a mode-locking method or the like. And, for example, mode-locking ultra-short pulsed lasers have been used in order to detect multi-photon fluorescence from a test object.

In a scanning microscope with pulsed light, pulsed light is irradiated to a test object, light from the test object is received by a light-detecting unit, detection signals outputted by the light-detecting unit are sampled, and an image is formed by using the intensities of the sampled detection signals as pixel values. In this case, the detection signals acquired by receiving the light from the test object become signals the light intensities of which attenuate as time passes by.

Accordingly, if the detection signals from the light-detecting unit are sampled just as the intensities of the detection signals have the maximum values respectively, it is possible to capture images with the highest sensitivity of detection.

As shown in FIG. 2 for example, the following Japanese Granted Patent No. 4667571 discloses a laser scanning microscope which includes: a laser device 61 playing a role as a pulsed laser oscillation means that generates pulsed laser oscillation; a photoelectric conversion unit 62 playing a role as a light-detecting unit that receives light from a test object 70 to output electrical signals; an A/D converter 63 playing a role as a sampling means that samples the electrical signals from the light detecting unit 62; a memory 64 storing data that are sampled by the sampling means 63; and a laser-oscillation-synchronizing-signal generating circuit 66 playing a role as a synchronous signal-generating means that outputs a synchronous signal made to synchronize with oscillation of pulsed laser in response to laser oscillation signals detected by a laser-oscillation detecting unit 65 detecting the pulsed laser oscillation. And, the laser scanning microscope disclosed in Japanese Granted Patent No. 4667571 further includes: a delay circuit unit 67 delaying the synchronous signal for a set amount of time to output trigger signals; and an external input circuit 68 for providing an amount of delay time $\Delta t$ with which the synchronous signal is delayed by the delay circuit unit 67, wherein the sampling means 63 samples the signals while the trigger signals from the delay circuit unit 67 are being used as a sampling clock. And, Japanese Granted Patent No. 4667571 suggests a method of performing sampling that is made to synchronize with an oscillation mode of laser in order to efficiently acquire detection signals in detection of multi-photon fluorescence. Besides, in FIG. 2, the numeral reference 69 denotes an image-displaying unit that displays an image formed by detection signals stored in the memory 64.

In the laser scanning microscope disclosed in Japanese Granted Patent No. 4667571, detection signals after photoelectric conversion are chronologically compared with trigger signals, and then a value of delay time which is inputted through the external input circuit 68 is changed so that peaks of the detection signals correspond with timing of the trigger signals outputted or so that images have the brightest brightness. As a result, it is possible to adjust timing at which the detection signals are sampled just as their intensities have the maximum values, in the laser scanning microscope disclosed in Japanese Granted Patent No. 4667571.

SUMMARY OF THE INVENTION

A laser scanning type observation apparatus according to the present invention is characterized in that the laser scanning type observation apparatus includes: a pulsed-laser oscillation means which generates pulsed-laser oscillation to irradiate a pulsed laser beam to a test object; a light detecting unit which receives light from the test object to output a detection signal; a synchronous signal generating means which detects the oscillation of pulsed laser from the pulsed-laser oscillation means to output a synchronous signal that is made to synchronize with oscillation of the pulsed laser beam; a delay circuit unit which delays the synchronous signal outputted by the synchronous signal generating means for an optional amount of time, to output a trigger signal; a sampling means which samples the detection signal outputted by the light detecting unit while the sampling of the detection signal is being made to synchronize with the trigger signal outputted by the delay circuit unit; and a memory unit in which the detection signal sampled by the sampling means is stored, wherein: the laser scanning type observation apparatus includes a multi-stage delay setting unit by which delay time for delaying the synchronous signal by the delay circuit unit can be set at at least two or more stages within one period of the synchronous signal, and the laser scanning type observation apparatus includes a decision unit which determines an optimum delay stage for image formation using data on intensities of the detection signal at the respective delay stages, the detection signal at the respective delay stages being sampled by the sampling means while the sampling of the detection signal at the respective delay stages by the sampling means is being made to synchronize with a trigger signal outputted by the delay circuit unit in accordance with the two or more stages of delay time set by the multi-stage delay setting unit and then the data on the intensities of the detection signal at the respective delay stages being stored in the memory unit; the multi-stage delay setting unit sets delay time for which the synchronous signal is delayed by the delay circuit unit, to delay time corresponding to the optimum delay stage for image formation which is determined by the decision unit; and the multi-stage delay setting unit fixes the delay time for which the synchronous signal is delayed by the delay circuit unit, at the delay time corresponding to the optimum delay stage for image formation, so as to be capable of performing observation.

Also, in a laser scanning type observation apparatus according to the present invention, it is preferred that the decision unit decides on a delay stage at which the detection signal has the largest intensity of the intensities of the detection signal at the respective delay stages which are stored in the memory unit as data, as an optimum delay stage for image formation.

Also, in a laser scanning type observation apparatus according to the present invention, it is preferred that the laser scanning type observation apparatus further includes a delay setting switch through which the multi-stage delay setting unit and the decision unit are made to set delay time corresponding to an optimum delay stage for image formation afresh.

Also, in a laser scanning type observation apparatus according to the present invention, it is preferred that: the laser scanning type observation apparatus further includes an ON-OFF switching unit which switches an on-operation of irradiation and an off-operation of irradiation to each other, the on-operation of irradiation causing irradiation of a pulsed laser beam generated by the pulsed-laser oscillation means to the test object and the off-operation of irradiation causing a stop of irradiation of a pulsed laser beam generated by the pulsed-laser oscillation means to the test object; and the decision unit determines an optimum delay stage for image formation, using data on intensities of the detection signal at the respective delay stages which are set by the multi-stage delay setting unit when the on-operation of irradiation or the off-operation of irradiation is performed by the ON-OFF switching unit.

Also, in a laser scanning type observation apparatus according to the present invention, it is preferred that the decision unit further calculates a value of contrast of the detection signal, using the data on the intensities of the detection signal at the respective delay stages which are set by the multi-stage delay setting unit when the on-operation of irradiation or the off-operation of irradiation is performed by the ON-OFF switching unit.

Also, in a laser scanning type observation apparatus according to the present invention, it is preferred that the decision unit further detects background noise, using the data on the intensities of the detection signal at the respective delay stages which are set by the multi-stage delay setting unit when the off-operation of irradiation is performed by the ON-OFF switching unit.

Also, in a laser scanning type observation apparatus according to the present invention, it is preferred that: the laser scanning type observation apparatus further includes a delay optical path unit which splits an optical path of the pulsed laser emitted by the pulsed-laser oscillation means into at least two or more optical paths and which multiplies a period of the pulsed laser emitted by the pulsed-laser oscillation means due to a difference between the different optical paths in length to irradiate a pulsed laser with the multiplied period to the test object; the ON-OFF switching unit is placed on at least one of the optical paths into which the optical path of the pulsed laser emitted by the pulsed-laser oscillation means is split by the delay optical path unit; and the ON-OFF switching unit switches from the on-operation of irradiation and the off-operation of irradiation to each other within one period of oscillation of the pulsed laser emitted by the pulsed-laser oscillation means.

Also, in a laser scanning type observation apparatus according to the present invention, it is preferred that: the synchronous signal generating means and the delay circuit unit constitute a sampling-clock generating means which outputs a sampling clock using a signal for the detection of the oscillation of pulsed laser from the pulsed-laser oscillation means, the sampling clock being made to synchronize with an oscillation mode of the pulsed-laser oscillation means; the laser scanning type observation apparatus further includes an AC-coupled amplifier which amplifies the detection signal outputted by the light detecting unit to output the amplified signal; the sampling means samples the detection signal which is amplified to be outputted by the AC-coupled amplifier while the sampling of the detection signal by the sampling means is being made to synchronize with the sampling clock outputted by the sampling-clock generating means; the laser scanning type observation apparatus further includes a processing unit which outputs a signal value for image formation with the detection signal that is sampled by the sampling means; the sampling means includes an AD converter means of two systems; and the processing unit includes a delay setting means and a difference calculating unit, the delay setting means consisting of the memory unit and the decision unit, the memory unit storing the detection signal sampled by the sampling means, the delay setting means being capable of adjusting and setting an amount of a delay of timing at which the detection signal is sampled by each of the two systems of the AD converter means, relative to each of the two systems, and the difference calculating unit outputting a difference between detection signals from the AD converter means of two systems as a signal value for image formation, the detection signals from the AD converter means of two systems being sampled at the timings set by the delay setting means.

Also, in a laser scanning microscope apparatus according to the present invention, it is preferred that the delay setting means adjusts amounts of delays of timings at which the detection signal is sampled by two systems of the AD converter means respectively, to make the amounts of the delays of the timings differ from each other by a half period of the oscillation frequency of the pulsed laser.

Also, in a laser scanning microscope apparatus according to the present invention, it is preferred that: the delay setting means adjusts an amount of a delay of timing at which the detection signal is sampled by a first system of the AD converter means of two systems so that a detection signal from the first system of the AD converter means has the maximum value; and the delay setting means adjusts an amount of a delay of timing at which the detection signal is sampled by a second system of the AD converter means of two systems so that a detection signal from the second system of the AD converter means has the minimum value.

According to the present invention, it is possible to acquire a laser scanning type observation apparatus: capable of sampling detection signals at the optimum timing for forming images without complicated adjustment for various observation conditions; and, in addition, capable of improving image qualities by maximizing contrast between detection signals and by removing background noise.

Also, according to the present invention, it is possible to acquire a laser scanning microscope apparatus: capable of detecting detection signals with large intensities; and capable of improving image qualities, even when an AC-coupled amplifier is used for the laser scanning microscope apparatus.

These and other features and advantages of the present invention will become apparent from the following detailed description of the preferred embodiments when taken in conjunction with the accompanying drawings.

BRIEF DESCRIPTION OF THE DRAWINGS

FIG. 13A is a view showing pulsed laser passing through a first optical path of the delay optical path unit, FIG. 13B is a view showing pulsed laser passing through a second optical path of the delay optical path unit to be delayed, FIG. 13C is a view showing pulsed laser passing through a third optical path of the delay optical path unit to be delayed, FIG. 13D is a view showing pulsed laser passing through a fourth optical path of the delay optical path unit to be delayed, and FIG. 13E is a view showing a pulse train with a period that is multiplied by making pulsed lasers pass through the first to fourth optical paths of the delay optical path unit respectively.

FIG. 19A is a view showing one example of the combinations, FIG. 19B is a view showing another example of the combinations, and FIG. 19C is a view showing yet another example of the combinations.

FIG. 20A is a view showing a waveform of light of pulsed laser emitted from the pulsed-laser oscillation means, FIG. 20B is a view showing a waveform of a monitor signal from the pulsed-laser oscillation means when pulsed-laser oscillation means generates pulsed laser oscillation, FIG. 20C is a view showing a waveform of the monitor signal shown in FIG. 20B after the monitor signal passes through a high magnification amplifier provided for the synchronous signal generating means and through a band-pass filter, and FIG. 20D is a view showing a waveform of sampling clock outputted by a clock device after the signal shown in FIG. 20C is inputted into the clock device provided for the delay circuit unit.

FIG. 22A is a block diagram showing a fundamental structure of a PLL oscillator, and FIG. 22B is a block diagram showing a fundamental structure of a PLL frequency synthesizer.

FIG. 28A is a view conceptually showing a movement of the laser-irradiation point, FIG. 28B is a graph showing the movement of the laser-irradiation point shown in FIG. 28A with the relation between scanning position and time, FIG. 28C is a graph showing the movement of the laser-irradiation point shown in FIG. 28A with the relation between scanning speed and time, and FIG. 28D is a graph showing the relation between the number of data on the detection signal sampled to be added to one another and time corresponding to a set scanning point in an imaging area.

FIG. 30 is an explanatory view showing examples of expressions of the reciprocals of 2 to 16 with a formula of addition of powers of ½.

FIGS. 31A and 31B are explanatory views showing an example of a structure of a divider circuit shown in FIG. 29, FIG. 31A is an explanatory view showing a register in which a binary result from a division by a power of two is acquired by shifting a binary digit to the right by one bit in binary notation, and FIG. 31B is an explanatory view showing an example of addition in a combination of registers shown in FIG. 31A in accordance with divisors.

DETAILED DESCRIPTION OF THE PREFERRED EMBODIMENTS

Figure 1:
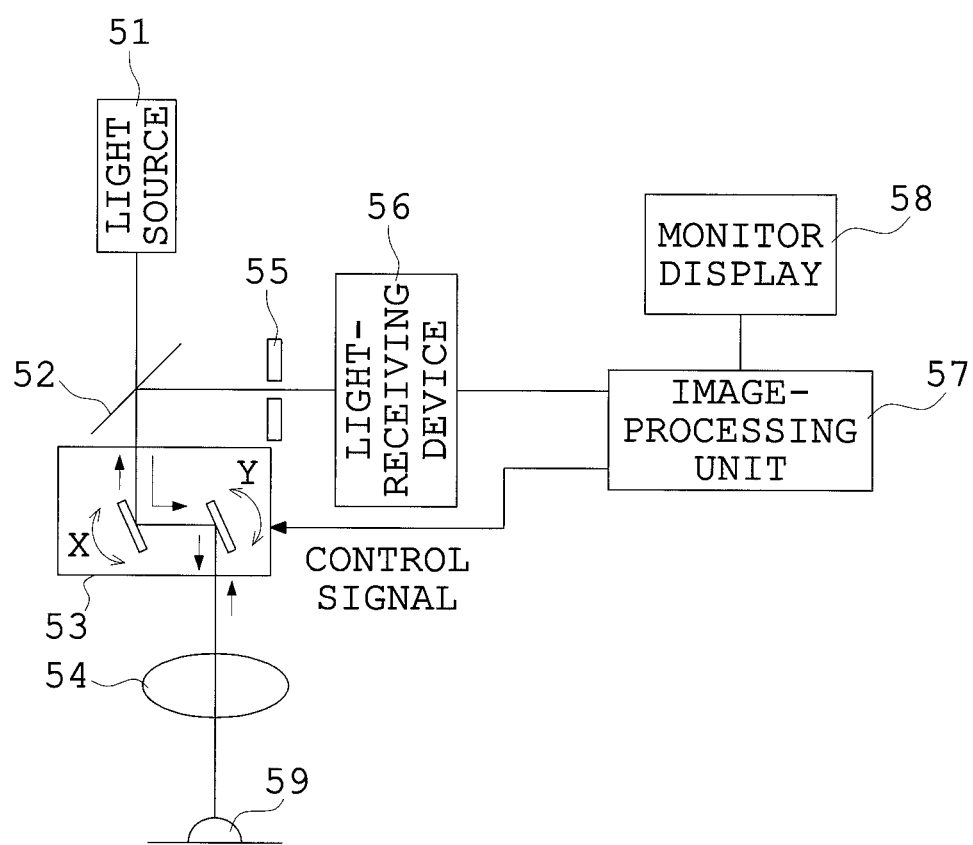
FIG. 1 is an explanatory view showing an example of structures of popular laser scanning microscopes in the prior art.
Figure 2:
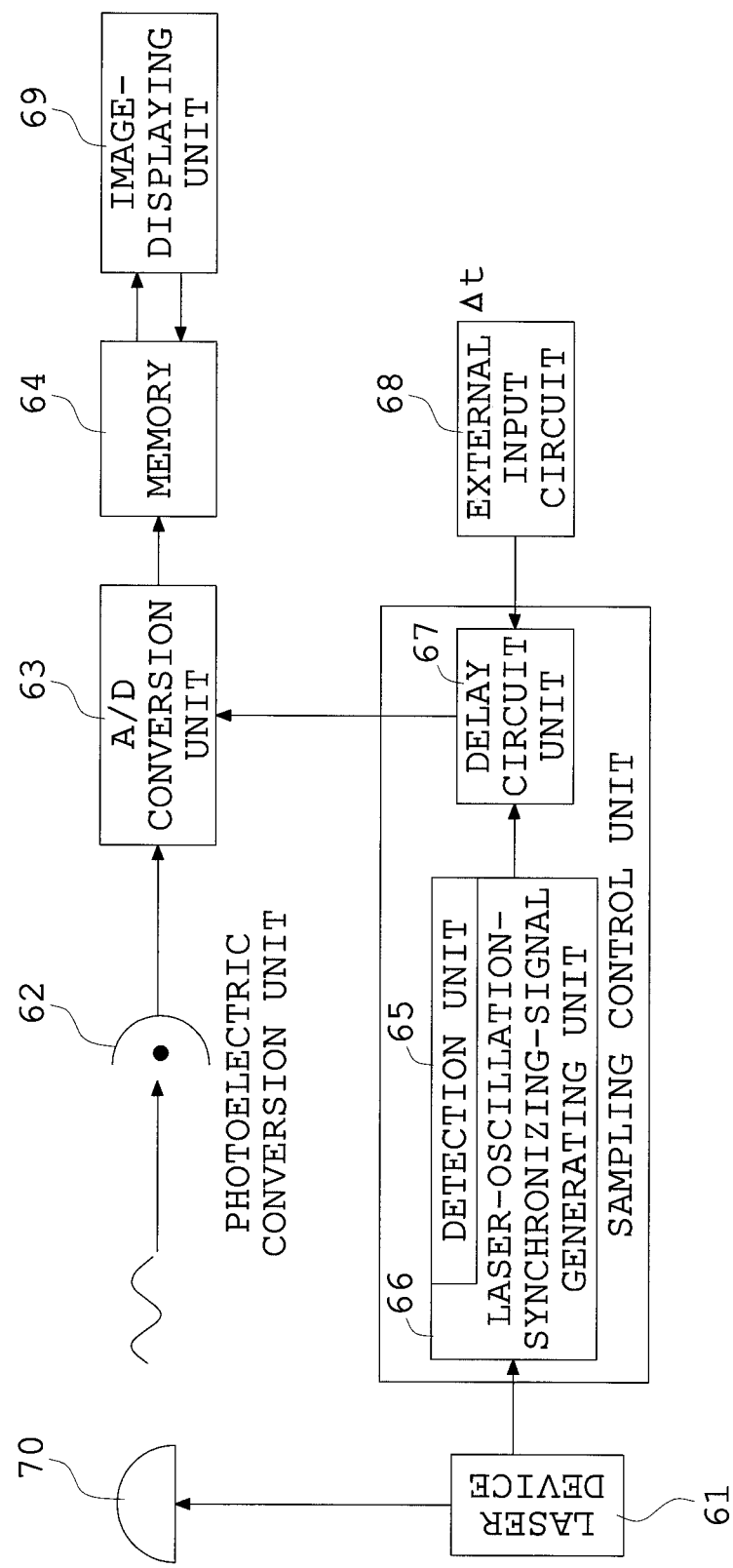
FIG. 2 is a block diagram schematically showing a structure of a laser scanning microscope disclosed in Japanese Granted Patent No. 4667571.

Prior to an explanation about embodiments of the present invention, operation effects in the present invention are explained.

A laser scanning type observation apparatus according to the present invention is configured to include: a pulsed-laser oscillation means which generates pulsed-laser oscillation to irradiate a pulsed laser beam to a test object; a light detecting unit which receives light from the test object to output a detection signal; a synchronous signal generating means which detects the oscillation of pulsed laser from the pulsed-laser oscillation means to output a synchronous signal that is made to synchronize with the oscillation of the pulsed laser beam; a delay circuit unit which delays the synchronous signal outputted by the synchronous signal generating means for an optional amount of time, to output a trigger signal; a sampling means which samples the detection signal outputted by the light detecting unit while the sampling of the detection signal is being made to synchronize with the trigger signal outputted by the delay circuit unit; and a memory unit in which the detection signal sampled by the sampling means is stored, wherein: the laser scanning type observation apparatus includes a multi-stage delay setting unit by which delay time for delaying the synchronous signal by the delay circuit unit can be set in at least two or more stages within one period of the synchronous signal, and the laser scanning type observation apparatus includes a decision unit which determines an optimum delay stage for image formation with data on the intensities of the detection signal at the respective delay stages, the detection signal at the respective delay stages being sampled by the sampling means while the sampling of the detection signal at the respective delay stages by the sampling means is being made to synchronize with a trigger signal outputted by the delay circuit unit in accordance with the two or more stages of delay time set by the multi-stage delay setting unit and then the data on the intensities of the detection signal at the respective delay stages being stored in the memory unit; the multi-stage delay setting unit sets delay time for which the synchronous signal is delayed by the delay circuit unit, to delay time corresponding to the optimum delay stage for image formation which is determined by the decision unit; and the multi-stage delay setting unit fixes the delay time for which the synchronous signal is delayed by the delay circuit unit, at the delay time corresponding to the optimum delay stage for image formation, so as to be capable of performing observation.

As in a laser scanning type observation apparatus according to the present invention, when the laser scanning type observation apparatus is provided with the multi-stage delay setting unit by which delay time for delaying the synchronous signal by the delay circuit unit can be set in at least two or more stages within one period of the synchronous signal, detection signals can be sampled with at least two or more kinds of timing, so that it is possible to select optimum timing for sampling of detection signals more precisely even though timing at which the intensity of a detection signal becomes the maximum one differs from timing set in design because of variations in products, variations in observation environments, variations in types of or states of test object, or the like.

Also, the laser scanning type observation apparatus is provided with a decision unit determining an optimum delay stage for image formation by using data on the intensity of the detection signal at the respective delay stages, the detection signal at the respective delay stages being sampled by the sampling means with the sampling of the detection signal at the respective delay stages made to synchronize with the trigger signal outputted by the delay circuit unit in accordance with the two or more stages of delay time set by the multi-stage delay setting unit and the data on the intensities of the detection signal at the respective delay stages being stored in the memory unit. As a result, it is possible to automatically select optimum timing for sampling of detection signals.

Also, the multi-stage delay setting unit is configured: to set delay time for which the synchronous signal is delayed by the delay circuit unit, to delay time corresponding to the optimum delay stage for image formation which is determined by the decision unit; and to fix the delay time for which the synchronous signal is delayed by the delay circuit at the delay time corresponding to the optimum stage for image formation at which the signal is delayed, so as to be capable of performing observation. As a result, it is possible to automatically sample detection signals at optimum timing for sampling that is determined by the decision unit.

Accordingly, the laser scanning type observation apparatus according to the present invention makes it possible to sample detection signals at optimum timing for image formation without a complicated adjustment to the apparatus in various observation conditions.

Besides, in a laser scanning type observation apparatus according to the present invention, it is preferred that the decision unit decides on a delay stage at which the detection signal has the largest intensity of the intensities of the detection signal at the respective delay stages which are stored in the memory unit as data, as an optimum delay stage for image formation.

Also, in a laser scanning type observation apparatus according to the present invention, when the laser scanning type observation apparatus further includes a delay setting switch through which the multi-stage delay setting unit and the decision unit are made to set delay time corresponding to an optimum delay stage for image formation afresh, a mere simple operation of the apparatus by a user makes it possible to sample detection signals at optimum timing for image formation, even though an observation condition like laboratory or test object for example is changed.

Also, in a laser scanning type observation apparatus according to the present invention, it is preferred that: the laser scanning type observation apparatus further includes an ON-OFF switching unit which switches an on-operation of irradiation and an off-operation of irradiation to each other, the on-operation of irradiation causing irradiation of a pulsed laser beam generated by the pulsed-laser oscillation means to the test object and the off-operation of irradiation causing a stop of irradiation of a pulsed laser beam generated by the pulsed-laser oscillation means to the test object; and the decision unit determines an optimum delay time for image formation, by using data on intensities of the detection signal at the respective delay stages which are set by the multi-stage delay setting unit when the on-operation of irradiation or the off-operation of irradiation is performed by the ON-OFF switching unit.

Such a configuration of the apparatus makes it possible to detect the intensities of a detection signal even when pulsed laser is not irradiated to a test object, makes it possible to adjust the apparatus to optimum sampling timing for improving image qualities which is decided on with a factor except intensity of detection signal, the factor being for example contrast value or background noise, and makes it possible to improve image qualities yet more by removing background noises in formation of images.

Besides, in a laser scanning type observation apparatus according to the present invention, it is preferred that the decision unit further calculates a value of contrast of the detection signal, by using the data on the intensities of the detection signal at the respective delay stages which are set by the multi-stage delay setting unit when the on-operation of irradiation or the off-operation of irradiation is performed by the ON-OFF switching unit.

Such a configuration of the apparatus makes it possible to decide on timing at which a detection signal has the maximum contrast as optimum timing for image formation, so that it is possible to improve image qualities.

Also, in a laser scanning type observation apparatus according to the present invention, it is preferred that the decision unit further detects background noise, by using the data on the intensities of the detection signal at the respective delay stages which are set by the multi-stage delay setting unit when the off-operation of irradiation is performed by the ON-OFF switching unit.

Such a configuration of the apparatus makes it possible to measure a background noise value in setting each timing simultaneously with an adjustment of sampling timing to improve image qualities yet more by removing the background noise in image formation.

Also, in a laser scanning type observation apparatus according to the present invention, it is preferred that: the laser scanning type observation apparatus further includes a delay optical path unit which splits the optical path of the pulsed laser emitted by the pulsed-laser oscillation means into at least two or more optical paths and which multiplies a period of the pulsed laser emitted by the pulsed-laser oscillation means due to a difference between the different optical paths in length to irradiate a pulsed laser with the multiplied period to the test object; the ON-OFF switching unit is placed on at least one of the optical paths into which the pulsed laser emitted by the pulsed-laser oscillation means is split by the delay optical path unit; and the ON-OFF switching unit switches from the on-operation of irradiation and the off-operation of irradiation to each other within one period of oscillation of the pulsed laser emitted by the pulsed-laser oscillation means.

Such a configuration of the apparatus makes it possible to change irradiation and non-irradiation of laser to the test object to each other at high speed and makes it possible to perform a series of processes for sampling detection signals at optimum timing for image formation and at high speed, so that it is possible to improve a resolution of a moving image by optimizing sampling timing in inter-frame operation or the like.

Besides, laser scanning type observation apparatuses according to the present invention include, for example, laser scanning microscopes and laser scanning endoscopes. Also, for example, reflected light, fluorescence, or scattering light is applicable to the present invention, as light traveling from a test object.

Also, in a laser scanning type observation apparatus according to the present invention, it is preferred that: the synchronous signal generating means and the delay circuit unit constitute a sampling-clock generating means which outputs a sampling clock using a signal for the detection of the oscillation of pulsed laser from the pulsed-laser oscillation means, the sampling clock being made to synchronize with an oscillation mode of the pulsed-laser oscillation means; the laser scanning type observation apparatus further includes an AC-coupled amplifier which amplifies the detection signal outputted by the light detecting unit to output the amplified signal; the sampling means samples the detection signal which is amplified to be outputted by the AC-coupled amplifier while the sampling of the detection signal by the sampling means is being made to synchronize with the sampling clock outputted by the sampling-clock generating means and; the laser scanning type observation apparatus further includes a processing unit which outputs a signal value for image formation with the detection signal that is sampled by the sampling means; the sampling means includes an AD converter means of two systems; and the processing unit includes a delay setting means consisting of the memory unit and the decision unit, the memory unit storing the detection signal sampled by the sampling means, the delay setting means being capable of adjusting and setting an amount of a delay of timing at which the detection signal is sampled by each of the two systems of the AD converter means, relative to each system of the AD converter means, and the processing unit includes a difference calculating unit outputting a difference between detection signals from the AD converter means of two systems as a signal value for image formation, the detection signals from the AD converter means of two systems being sampled with timings that are set by the delay setting means respectively.

Figure 3:
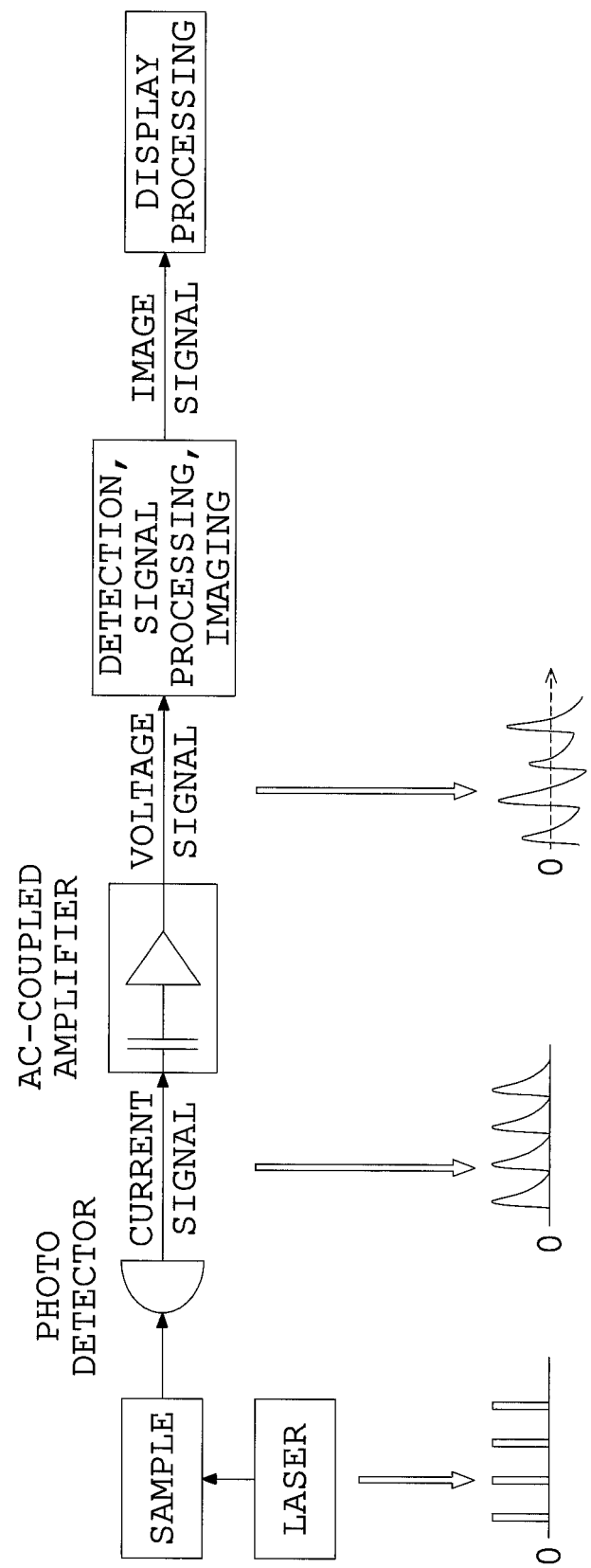
FIG. 3 is an explanatory view schematically showing a structure of a laser scanning microscope in which a detection signal outputted by a light detecting unit is amplified by an AC-coupled amplifier and conceptually showing a waveform of oscillation of pulsed laser, a waveform of a current signal outputted by the light detecting unit performing photoelectric conversion, and a waveform of a voltage signal amplified by the AC-coupled amplifier.

In a laser scanning microscope in which detection signal outputted by a light detecting unit is amplified by an AC-coupled amplifier, as shown in FIG. 3 for example, a laser is irradiated to a sample (test object), light from the sample is converted into a current signal by the light detecting unit, and the current signal is amplified by an AC-coupled amplifier and then a voltage signal is outputted. And, the outputted signal is sampled and then the sampled signal is given a set imaging process to be outputted as an image signal.

In this case, when a detection signal outputted by the light detecting unit (current signal) is amplified by the AC-coupled amplifier and the AC-coupled amplifier outputs a voltage signal, the outputted signal becomes a signal from which DC components are removed. As a result, the magnitude of the amplified detection signal (peak value) inevitably becomes a half value of the original peak value.

If the magnitude of the amplified detection signal becomes a half value of the original peak value, the peak value of a wave of the detection signal is considerably affected by the peak value of an adjacent wave in the case where feeble fluorescence is detected for example, so that there is a possibility that an accuracy of image quality deteriorates.

Although there is an idea that the magnitude of amplified detection signal is doubled, as schematically shown in FIG. 3, waveforms of the detection signal formed per period differ from one another in size. In addition, DC components which are removed by amplifying the detection signal to output the amplified signal by an AC-coupled amplifier is an average value. Accordingly, an error between: a peak value of the detection signal having been doubled; and the original peak value becomes large even if signal values of the detection signal in respective waveforms are doubled, so that it is difficult to acquire image quality with high accuracy.

Figure 4:
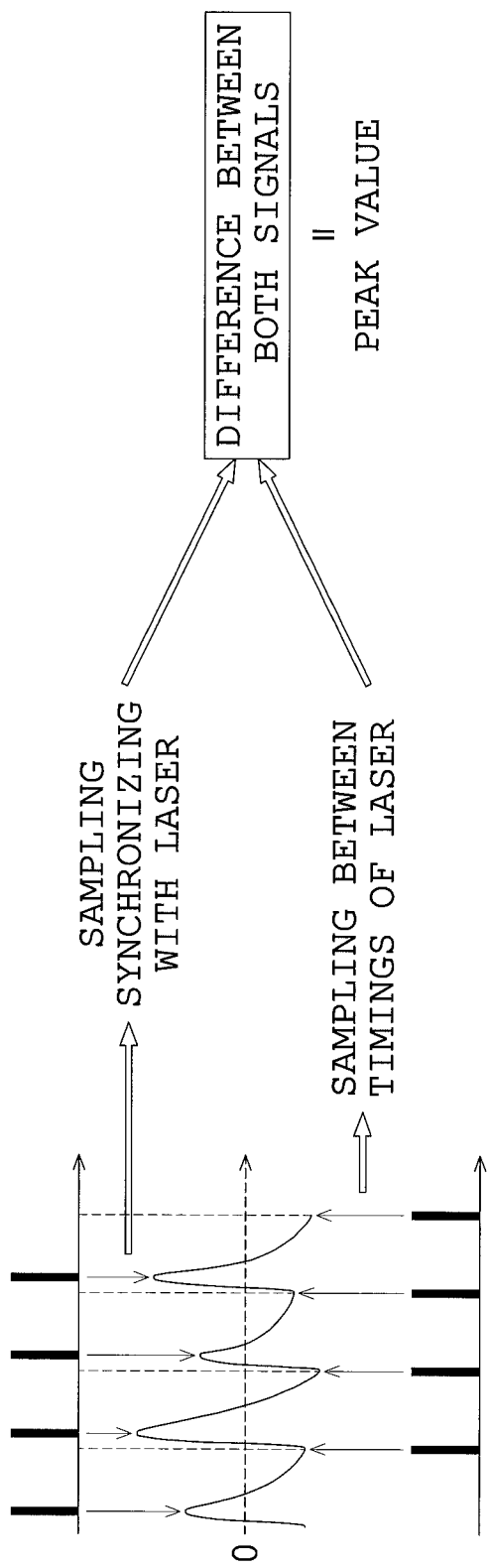
FIG. 4 is an explanatory view conceptually showing a process of outputting signals for image formation with voltage signals amplified by the AC-coupled amplifier in a laser scanning microscopic apparatus according to the present invention.

However, as in the laser scanning microscope apparatus according to the present invention, the sampling means includes an AD converter means of two systems, and the processing unit includes: a delay setting means capable of adjusting and setting an amount of a delay of timing at which the detection signal is sampled by each of the two systems of the AD converter means, relative to each system of the AD converter means; and a difference calculating unit outputting a difference between detection signals outputted from the AD converter means of two systems as a signal value for image formation, the detection signals outputted from the AD converter means of two systems being sampled with respective timings that are set by the delay setting means respectively. As a result, as shown in FIG. 4, the first system of the AD converter means samples the voltage signal amplified to be outputted by the AC-coupled amplifier, at timing at which the waveform of the voltage signal shows its peak, and the second system of the AD converter means samples the voltage signal amplified to be outputted by the AC-coupled amplifier, at timing at which the waveform of the voltage signal shows dip. And then, the difference calculating unit calculates a difference between: the signal sampled by the first system; and the signal sampled by the second system. As a result, even though the magnitude of a detection signal amplified by the AC-coupled amplifier (peak value) becomes a half value of the original peak value, it is possible to acquire the original peak value. As a result, the influence of the peak value of an adjacent wave become small even if feeble fluorescence is detected for example, so that an accuracy of image quality is improved.

Also, in a laser scanning type observation apparatus according to the present invention, it is preferred that the delay setting means adjusts amounts of delays of timings at which the detection signal is sampled by two systems of the AD converter means respectively, to make the amounts of the delays of the timings differ from each other by a half period of the oscillation frequency of the pulsed laser.

Such a manner makes it easy for the first system of AD converter means to sample a voltage signal amplified to be outputted by the AC-coupled amplifier at timing at which the waveform of the voltage signal approximately shows its peak, and makes it easy for the second system of the AD converter means to sample the voltage signal amplified to be outputted by the AC-coupled amplifier at timing at which the waveform of the voltage signal shows dip, for example.

Besides, in a laser scanning microscope apparatus according to the present invention, it is preferred that: the delay setting means adjusts an amount of a delay of timing at which the detection signal is sampled by the first system of the AD converter means of two systems so that a detection signal outputted from the first system of the AD converter means has the maximum value; and the delay setting means adjusts an amount of a delay of timing at which a detection signal is sampled by a second system of the AD converter means of two systems so that a detection signal outputted from the second system of the AD converter means has the minimum value.

Such a manner makes it possible to acquire the original peak value of a detection signal with high accuracy even if the detection signal which is amplified to be outputted by the AC-coupled amplifier is used, so that it is possible to improve an accuracy of image quality yet more.

The embodiments of the present invention are explained below using the drawings.

The First Embodiment

Figure 5:
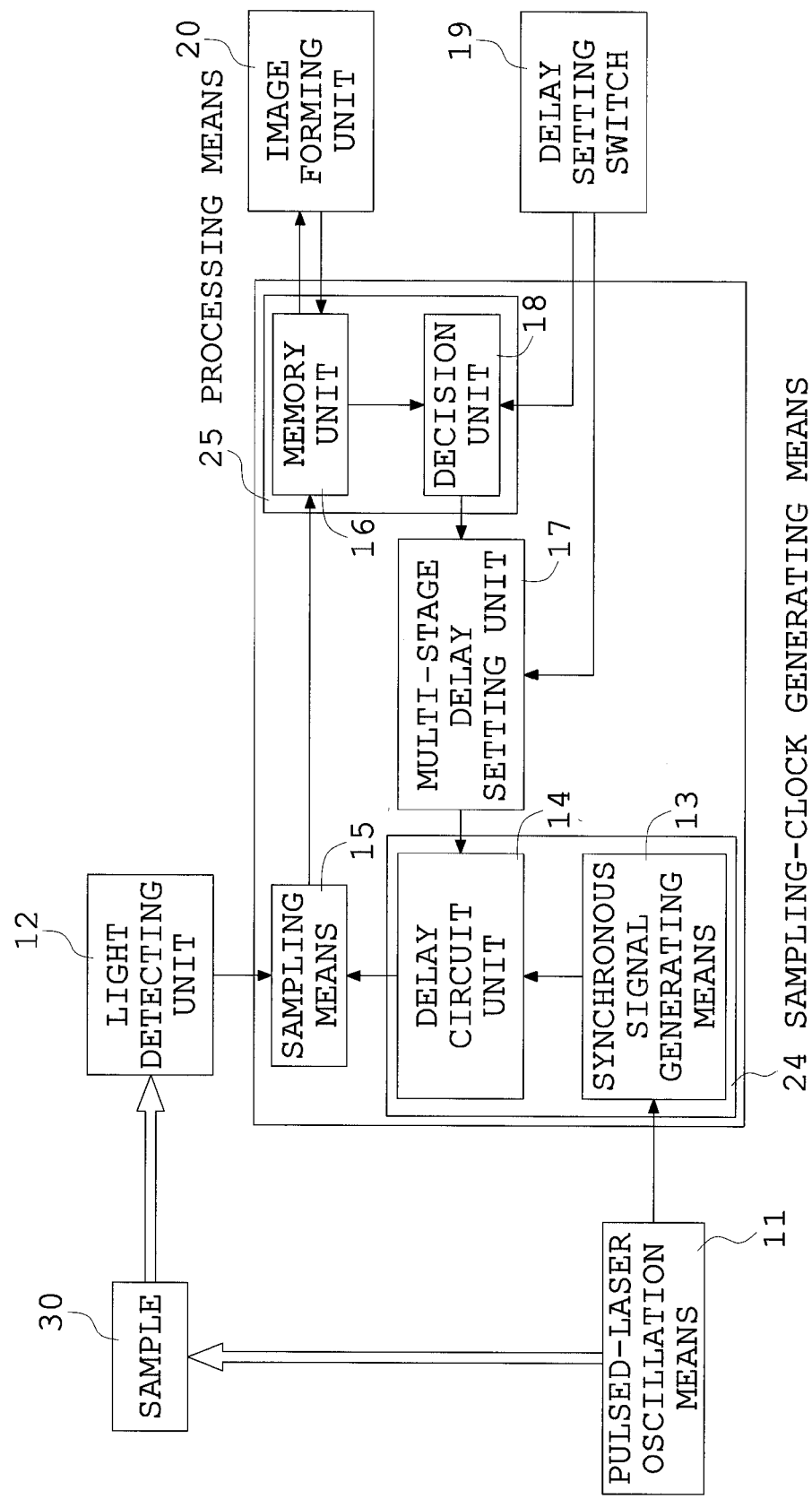
FIG. 5 is a block diagram schematically showing a structure of a laser scanning type observation apparatus of a first embodiment according to the present invention.
Figure 6:
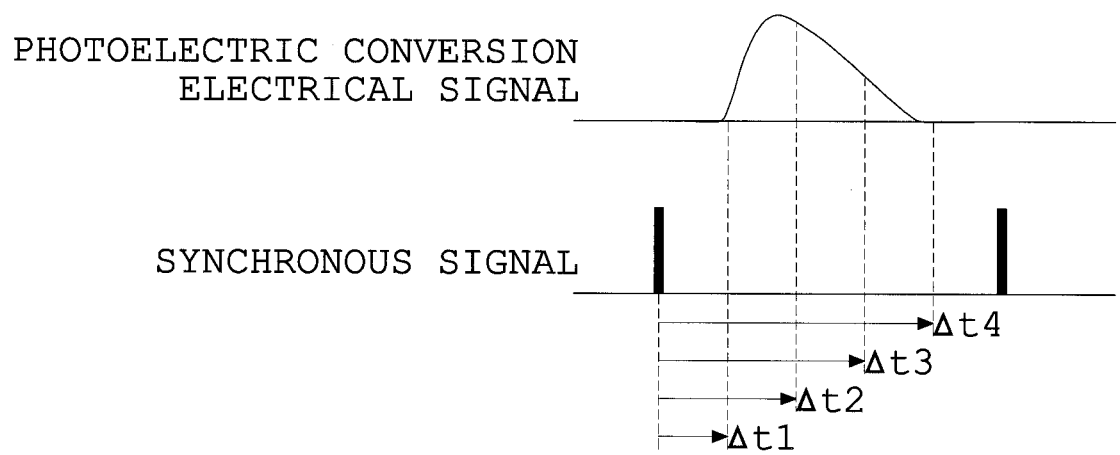
FIG. 6 is an explanatory view showing one example of electrical signals outputted by a light detecting unit performing photoelectric conversion, one example of synchronous signals synchronizing with oscillation of pulsed laser, and one example of timing at which the synchronous signals are delayed, in the laser scanning type observation apparatus shown in FIG. 5.
Figure 7:
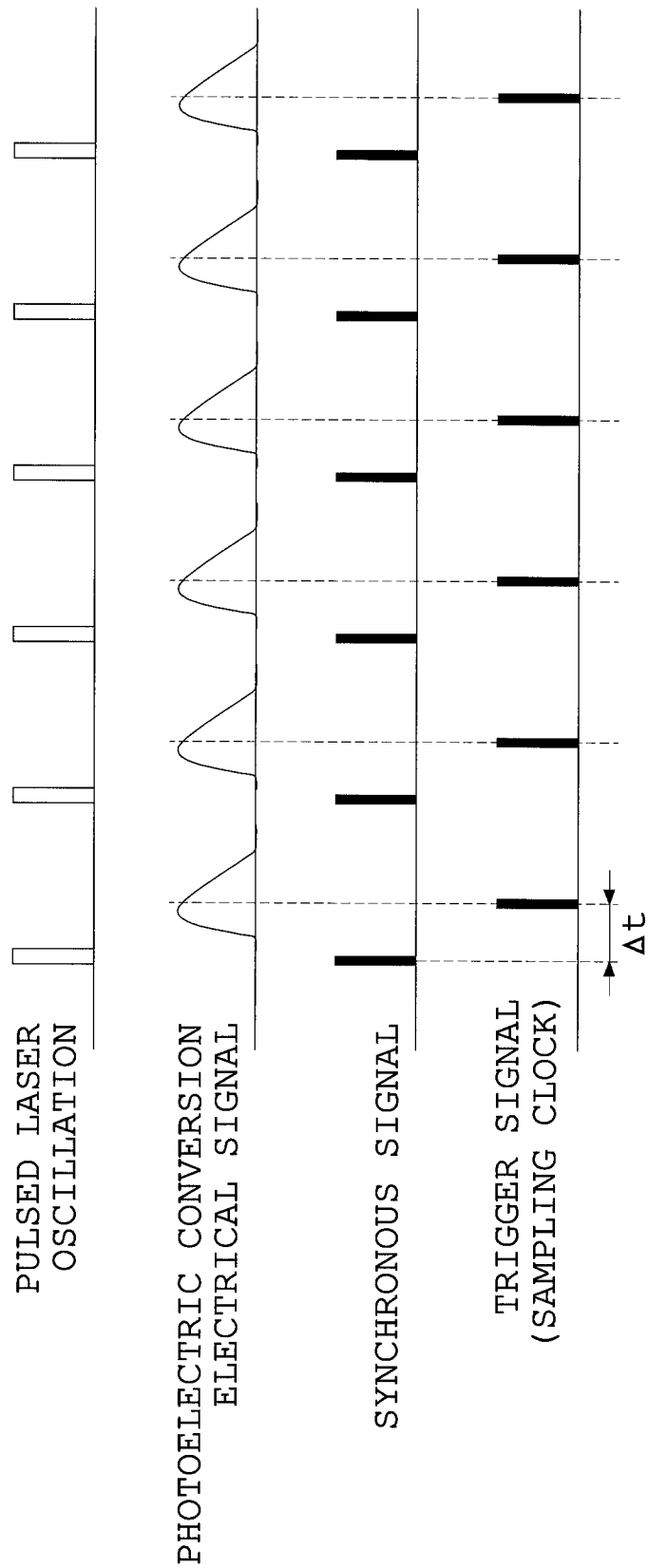
FIG. 7 is an explanatory view showing one example of timing charts of oscillation of pulsed laser, an electric signal into which light is photo-electrically converted by the light detecting unit and which is outputted by the light detecting unit, a synchronous signal synchronizing with the oscillation of the pulsed laser, and a trigger signal (sampling clock) that are outputted with a delay of a set amount of time relative to the synchronous signal, in the laser scanning type observation apparatus shown in FIG. 5.
Figure 8:
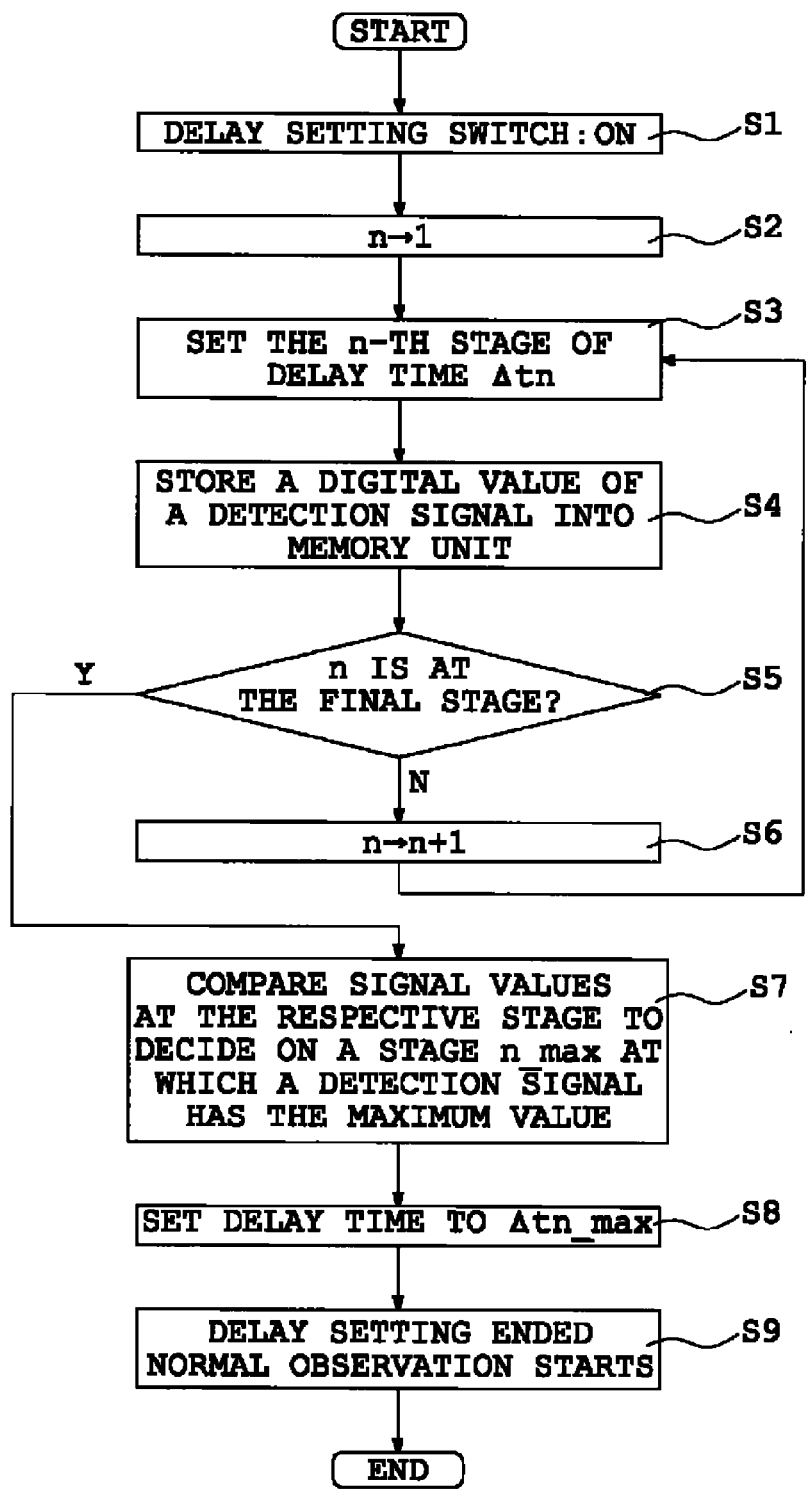
FIG. 8 is a flow chart showing one example of procedures for setting delay time for optimizing timing at which a detection signal is sampled, in the laser scanning type observation apparatus shown in FIG. 5.

FIG. 5 is a block diagram schematically showing a structure of a laser scanning type observation apparatus of a first embodiment according to the present invention. FIG. 6 is an explanatory view showing one example of electrical signals outputted by a light detecting unit performing photoelectric conversion, one example of a synchronous signal synchronizing with an oscillation of pulsed laser, and one example of timing at which the synchronous signal is delayed, in the laser scanning type observation apparatus shown in FIG. 5. FIG. 7 is an explanatory view showing one example of timing charts of oscillation of pulsed laser, an electric signal into which light is photo-electrically converted by the light detecting unit and which is outputted by the light detecting unit, a synchronous signal synchronizing with the oscillation of the pulsed laser, and a trigger signal (sampling clock) that are outputted with a delay of a set amount of time relative to the synchronous signal, in the laser scanning type observation apparatus shown in FIG. 5. FIG. 8 is a flow chart showing one example of procedures for setting delay time for optimizing timing at which a detection signal is sampled, in the laser scanning type observation apparatus shown in FIG. 5.

A laser scanning type observation apparatus according to the present embodiment includes a pulsed-laser oscillation means 11, a light detecting unit 12, a synchronous signal generating means 13, a delay circuit unit 14, a sampling means 15, a memory unit 16, a multi-stage delay setting unit 17, a decision unit 18, and a delay setting switch 19, as shown in FIG. 5. Besides, the reference numeral 20 shown in FIG. 5 denotes an image forming unit which forms a digital image by using the intensities of digital signals read out from the memory unit 16 as pixel values, and the reference numeral 30 shown in FIG. 5 denotes a test object (sample).

The pulsed-laser oscillation means 11 is configured to be a laser device generating pulsed-laser oscillation to irradiate a pulsed laser beam to the test object 30.

The light detecting unit 12 is, for example, a photo detector, a photo multiplier, a CCD imager, or a CMOS imager. And, the light detecting unit 12 receives light which travels from the test object 30 when pulsed laser emitted from the pulsed-laser oscillation means 11 is irradiated to the test object 30, and then the light detecting unit 12 photo-electrically converts the received light into an analog electric signal to output the analog electric signal as a detection signal. Besides, the light detecting unit 12 may be provided with a built-in I/V converter or a built-in amplifier, to have a signal conversion function.

For example, the synchronous signal generating means 13 detects oscillation of pulsed laser from the pulsed-laser oscillation means 11 through: a trigger output signal outputted as an electric signal synchronizing with the oscillation of the pulsed laser from the pulsed laser oscillating unit 11; or an electric signal into which a part of the pulsed laser is photo-electrically converted by a photo detector or a photo multiplier for example, and then the synchronous signal generating means 13 outputs a clock signal synchronizing with the oscillation of the pulsed laser from the pulsed-laser oscillation means 11.

The delay circuit unit 14 delays the clock signal outputted by the synchronous signal generating means 13 by delay time ($\Delta t$) which is optionally set by the multi-stage delay setting unit 17, to output a trigger signal. For example, the delay circuit unit 14 may be configured in a combination of a plurality of delay circuits to make it possible to select desired delay time or may be configured to output a trigger signal which is delayed by desired delay time through a digital signal process with a software or a FPGA (Field-Programmable Gate Array).

And, the synchronous signal generating means 13 and the delay circuit unit 14 constitutes a sampling-clock generating means 24. The sampling-clock generating means 24 outputs a sampling clock which synchronizes with an oscillation mode of the pulsed-laser oscillation means 11, using the signal for the detection of oscillation of pulsed laser from the pulsed-laser oscillation means 11.

The sampling means 15 is composed of an A/D converter having a function of converting an analog signal outputted by the light detecting unit 12 into a digital signal to sample the digital signal while the signal conversion and the sampling are being synchronizing with a trigger signal that is outputted by the delay circuit unit 14.

The memory unit 16 is provided for a processing unit 25, and digital signals sampled by the sampling means 15 are stored (memorized) in the memory unit 16.

The multi-stage delay setting unit 17 performs control to set delay time ($\Delta t$) for delaying a clock signal by the delay circuit unit 14 at at least two or more stages within one period of the clock signal. The delay circuit unit 14 is configured to be capable of changing delay time for delaying a clock signal through a control signal from the multi-stage delay setting unit 17. Besides, the control signal from the multi-stage delay setting unit 17 may be an analog signal or a digital signal. Also, the multi-stage delay setting unit 17 may be provided with settings of delay time and the number of stages of delay time which are given to the delay circuit unit 14 in setting of delay time, in a manufacturing stage, or may be configured so that delay time and the number of stages of delay time can be optionally set through an exterior input means that is not shown in the drawings.

The decision unit 18 is provided for the processing unit 25 and compares data on the intensities of a digital signal at the respective delay stages with one another, the data on the intensities of the digital signal at the respective delay stages being sampled by the sampling means 15 while the sampling by the sampling means 15 is synchronizing with a trigger signal outputted by the delay circuit unit 14 in accordance with delay times at two or more stages which are set by the multi-stage delay setting unit 17 and then the data on the intensities of the digital signal at the respective delay stages being stored (memorized) in the memory unit 16. And then, the decision unit 18 determines an optimum delay stage (delay time) for image formation.

More specifically, as shown in FIG. 6 for example, the decision unit 18 compares data on a detection signal at delay stages set by the multi-stage delay setting unit 17 with one another (the delay stages set by the multi-stage delay setting unit 17 being $\Delta t1$, $\Delta t2$, $\Delta t3$, and $\Delta t4$ in the example shown in FIG. 6, for example), the data on the detection signal at the delay stages being stored (memorized) in the memory unit 16, the decision unit 18 decides on the most optimum delay stage for image formation (which is timing for sampling a detection signal), and the decision unit 18 sends a signal for communicating the delay stage of the decision result to the multi-stage delay setting unit 17 (the delay stage of the decision result being the delay stage Δt2 at which the detection signal has the largest intensity of intensities which the detection signal has at the delay stages set by the multi-stage delay setting unit 17, in the example shown in FIG. 6 for example).

The multi-stage delay setting unit 17 sets the delay circuit unit 14 to a delay time corresponding to the optimum delay stage for image formation that is determined by the decision unit 18, as delay time for delaying a clock signal by the delay circuit unit 14.

The delay setting switch 19 is configured to make it possible for a user to perform a setting process for setting delay time corresponding to optimum delay stage for image formation by the multi-stage delay setting unit 17 and the decision unit 18 through operation of the delay setting switch 19 by the user, afresh and at any time.

A procedure of setting delay time in the laser scanning type observation apparatus according to the first embodiment which is configured in such a manner is explained using FIG. 8.

A user switches the delay setting switch 19 on (Step S1). As a result, the multi-stage delay setting unit 17 and the decision unit 18 start a new setting process for setting delay stage.

More specifically, the multi-stage delay setting unit 17 sets the delay circuit unit 14 to a plurality of delay stages Δtn (n denotes a natural number) to be set (Step S3). As a result, the delay circuit unit 14 delays a synchronous signal outputted by the synchronous signal generating means 13 by time corresponding to each delay stage Δtn which is set by the multi-stage delay setting unit 17, to output a trigger signal.

Next, the sampling means 15 samples a digital detection signal outputted by the light detecting unit 12 while the sampling of the digital detection signal by the sampling means 15 is synchronizing with the trigger signal that is outputted by the delay circuit unit 14, and the detection signal sampled by the sampling means 15 is stored (memorized) in the memory unit 16 (Step S4).

These processes of Steps S3 to S4 are repeated until the delay stages Δtn reach to the final stage (Step S5 and Step S6).

When the delay stages Δtn reach to the final stage, the decision unit 18 compares data on the intensities of the detection signal at the respective delay stages with one another, the data on the intensities of the detection signal at the respective delay stages being stored in the memory unit 16, and then the decision unit 18 decides on a delay stage n_max at which the detection signal has the largest intensity, as optimum delay stage for image formation (Step S7).

Next, the multi-stage delay setting unit 17 sets delay time corresponding to optimum delay stage for image formation determined by the decision unit 18, to the delay time Δtn_max for which the clock signal is delayed by the delay circuit 14 (Step S8). As a result, the process for setting delay stage by the multi-stage delay setting unit 17 and the decision unit 18 is finished. In observation after this process for setting delay stage is finished, the setting of delay time given to the delay circuit unit 14 is fixed at the optimum delay time (Δt2, for example) for observation.

According to the first embodiment, the laser scanning type observation apparatus according to the first embodiment is provided with the multi-stage delay setting unit 17 which can give the delay circuit unit 14 a setting of delay time for delaying a synchronous signal by the delay circuit unit 14 in at least two or more stages within one period of the synchronous signal, so that delay time (Δt) can be changed into at least two or more types of delay time within one period of oscillation of pulsed laser (or, within one period of a clock signal). As a result, it is possible to sample the waveform of a photo-electrically converted electric signal with at least two or more types of timings. As a result, even though timing at which a detection signal has the maximum intensity differs from timing set in design due to variation in productions, a difference in observation environment, or a difference in types of test objects or in states of a test object 30, the apparatus according to the first embodiment makes it possible to select optimum timing for sampling detection signals more accurately.

Also, according to the present embodiment, the laser scanning type observation apparatus according to the present embodiment is provided with the decision unit 18 which determines optimum delay time for image formation using data on the intensities of a detection signal at respective delay stages, the data on the intensities of the detection signal at the respective delay stages being sampled by the sampling means 15 while the sampling by the sampling means 15 is synchronizing with a trigger signal outputted by the delay circuit unit 14 in accordance with two or more stages of delay time set by the multi-stage delay setting unit 17 and then the data on the intensities of the detection signal at the respective delay stages being stored in the memory unit 16, so that it is possible to automatically select optimum timing for detecting the signal.

Also, the multi-stage delay setting unit 17 is configured to set the delay circuit unit 14 to delay time corresponding to the optimum delay stage for image formation which is determined by the decision unit 18 as delay time for delaying a synchronous signal by the delay circuit unit 14 and is configured to make it possible to observe a test object while delay time for delaying the synchronous signal by the delay circuit unit 14 is being fixed at the delay time corresponding to the optimum delay stage for image formation. As a result, it is possible to automatically sample detection signals at optimum timing for detection which is selected by the decision unit 18.

Accordingly, according to the present embodiment, the laser scanning type observation apparatus according to the present embodiment makes it possible to sample detection signals at optimum timing for image formation without complicated adjustment made by a user in various observation conditions.

Also, according to the present embodiment, the laser scanning type observation apparatus according to the present embodiment is provided with the delay setting switch 19 which makes the multi-stage delay setting unit 17 and the decision unit 18 perform a process for setting delay time corresponding to optimum delay stage for image formation, afresh. As a result, it is possible to sample detection signals at optimum timing for image formation only by simple operation performed by a user, even if an observation condition like laboratory or a test object is changed for example.

The Second Embodiment

Figure 9:
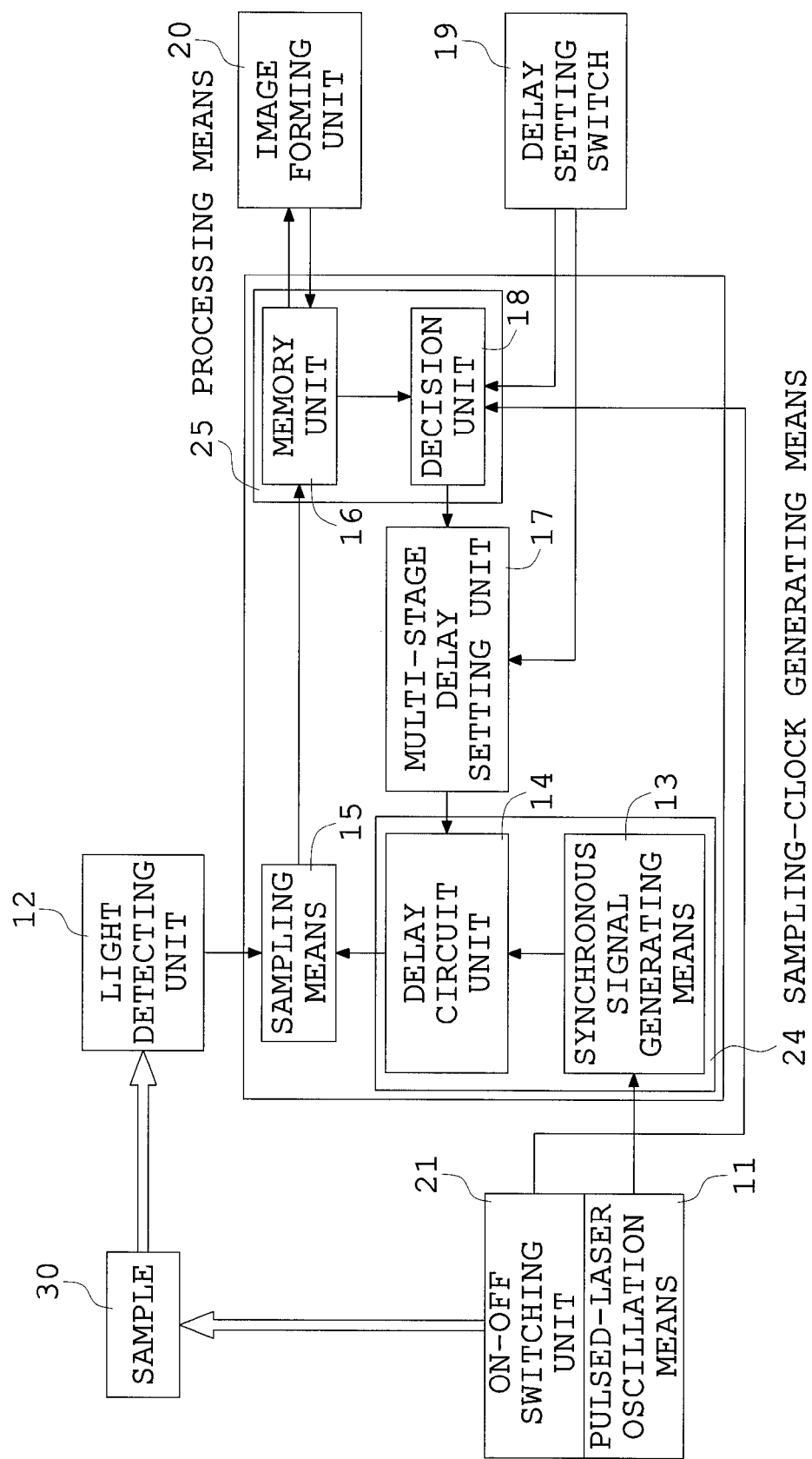
FIG. 9 is a block diagram schematically showing a structure of a laser scanning type observation apparatus according to a second embodiment of the present invention.
Figure 10:
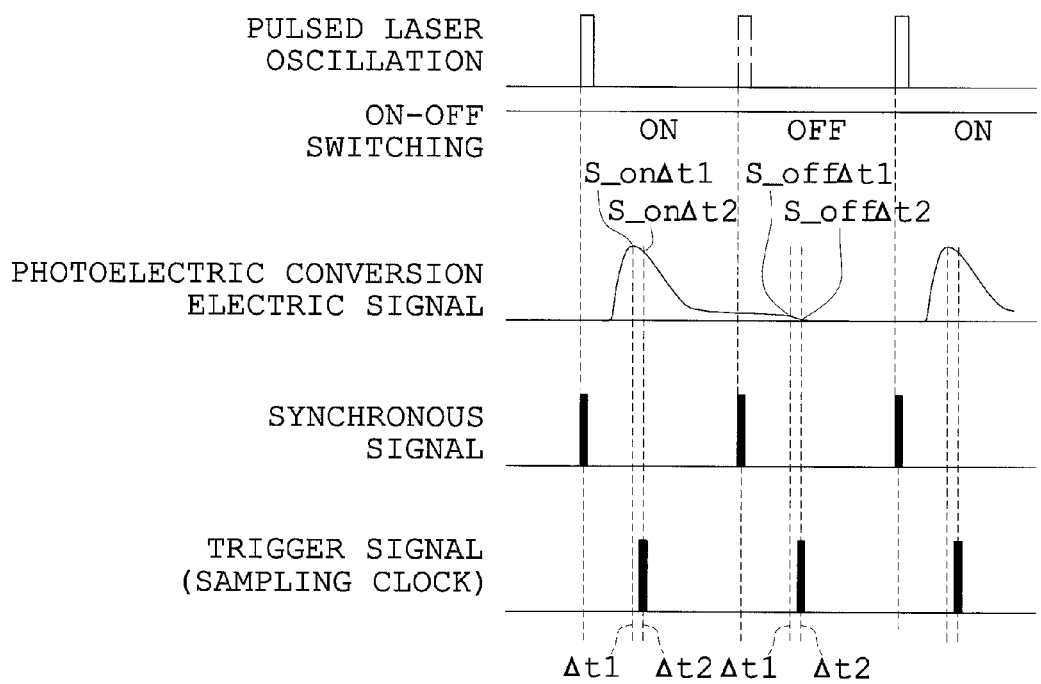
FIG. 10 is an explanatory view showing one example of timing charts of oscillation of pulsed laser, an electric signal into which light is photo-electrically converted by the light detecting unit and which is outputted by the light detecting unit, a synchronous signal synchronizing with the oscillation of the pulsed laser, and a trigger signal (sampling clock) that are outputted with a delay of a set amount of time relative to the synchronous signals, in the laser scanning type observation apparatus shown in FIG. 9.

FIG. 9 is a block diagram schematically showing a structure of a laser scanning type observation apparatus according to a second embodiment of the present invention. FIG. 10 is an explanatory view showing one example of timing charts of oscillation of pulsed laser, an electric signal into which light is photo-electrically converted by the light detecting unit and which is outputted by the light detecting unit, a synchronous signal synchronizing with the oscillation of the pulsed laser, and a trigger signal (sampling clock) that is outputted with a delay of a set amount of time relative to the synchronous signal, in the laser scanning type observation apparatus shown in FIG. 9. Besides, components for the second embodiment which have the same structures as in FIG. 5 are given the same numeral references respectively, and detailed explanations about these components are omitted.

A laser scanning type observation apparatus according to the present embodiment not only has the constitution of the laser scanning type observation apparatus according to the first embodiment as shown in FIG. 5 but also includes an ON-OFF switching unit 21 which is provided for the pulsed-laser oscillation means 11, as shown in FIG. 9. And, the laser scanning type observation apparatus according to the present embodiment is configured to operate in such a way that: irradiation of pulsed laser generated by the pulsed-laser oscillation means 11 to a test object 30 is temporarily stopped when the ON-OFF switching unit 21 performs an off-operation of irradiation; and a light detecting unit 12 can continue to photo-electrically convert light into an electric signal even during the temporary stop of the emission of pulsed laser by the pulsed-laser oscillation means 11.

The ON-OFF switching unit 21 is composed of a light intercepting member capable of switching interception of light and travel of light to each other, like a shutter for example. And, the ON-OFF switching unit 21 changes an on-operation of irradiation and the off-operation of irradiation to each other, the on-operation of irradiation causing irradiation of pulsed laser generated by the pulsed-laser oscillation means 11 to the test object 30 and the off-operation of irradiation causing a stop of irradiation of pulsed laser generated by the pulsed-laser oscillation means 11 to the test object 30

When the decision unit 18 determines an optimum delay stage for image formation, the decision unit 18 uses data on the intensities of a detection signal at respective delay stages that are set by the multi-stage delay setting unit 17 when the ON-OFF switching unit 21 performs the on-operation of irradiation and the off-operation of irradiation respectively.

More specifically, the decision unit 18 further calculates a contrast value of the detection signal using the data on the intensities of the detection signal at respective delay stages that are set by the multi-stage delay setting unit 17 when the ON-OFF switching unit 21 performs the on-operation of irradiation and the off-operation of irradiation respectively.

A common formula such as $\{(S\_on)-(S\_off)\}/\{(S\_on)+(S\_off)\}$ or $(S\_on)/(S\_off)$ is used as a formula for calculating contrast values, for example. In these formulas, S_on denotes the intensity of a detection signal when the ON-OFF switching unit 21 performs the on-operation of irradiation, and S_off denotes the intensity of a detection signal when the ON-OFF switching unit 21 performs the off-operation of irradiation.

Now, in the case where the multi-stage delay setting unit makes a setting of two delay stages of $\Delta t1$ and $\Delta t2$ for example, a process performed by the decision unit 18 for the second embodiment is explained in more detail.

In this explanation, $S\_on\Delta t1$ denotes the intensity of a detection signal at the delay stage $\Delta t1$ when the ON-OFF switching element 21 performs the on-operation of irradiation, $S\_off\Delta t1$ denotes the intensity of the detection signal at the delay stage $\Delta t1$ when the ON-OFF switching element 21 performs the off-operation of irradiation, $S\_on\Delta t2$ denotes the intensity of the detection signal at the delay stage $\Delta t2$ when the ON-OFF switching element 21 performs the on-operation of irradiation, and $S\_off\Delta t2$ denotes the intensity of the detection signal at the delay stage $\Delta t2$ when the ON-OFF switching element 21 performs the off-operation of irradiation. Also, for the sake of convenience, it is presumed that the intensity of the detection signal at the delay stage $\Delta t1$ is larger than the intensity of the detection signal at the delay stage $\Delta t2$ when the ON-OFF switching unit 21 performs the on-operation of irradiation (that is to say, the case where $S\_on\Delta t2<S\_on\Delta t1$ is presumed).

In the laser scanning type observation apparatus according to the first embodiment, the decision unit 18 is configured to decide that the delay stage $\Delta t1$ at which a detection signal has the maximum intensity in the on-operation of irradiation by the ON-OFF switching unit 21 is an optimum delay stage for image formation.

On the other hand, in the laser scanning type observation apparatus according to the second embodiment, the decision unit 18 does not immediately decide that the delay stage at which a detection signal has the maximum intensity in the on-operation of irradiation by the ON-OFF switching unit 21 is an optimum delay stage for image formation but adds to factors for decision also a delay stage at which the maximum contrast is acquired, to determine an optimum delay stage for image formation, for example.

For example, in the case where there is no difference between: the intensity of the detection signal at the delay stage $\Delta t1$ in the off-operation of irradiation by the ON-OFF switching unit 21; and the intensity of the detection signal at the delay stage $\Delta t2$ in the off-operation of irradiation by the ON-OFF switching unit 21 ($S\_off\Delta t1=S\_off\Delta t2$), the contrast $(S\_on\Delta t1)/(S\_off\Delta t1)$ of the detection signal at the delay stage $\Delta t1$ is larger than the contrast $(S\_on\Delta t2)/(S\_off\Delta t2)$ of the detection signal at the delay stage $\Delta t2$. In this case, the decision unit 18 decides that a delay stage at which a detection signal has the maximum intensity in the on-operation of irradiation by the ON-OFF switching unit 21 is an optimum delay stage for image formation, like the laser scanning type observation apparatus according to the first embodiment.

On the other hand, in the case where the intensity of the detection signal at the delay stage $\Delta t1$ in the off-operation of irradiation by the ON-OFF switching unit 21 is larger than the intensity of the detection signal at the delay stage $\Delta t2$ in the off-operation of irradiation by the ON-OFF switching unit 21 ($S\_off\Delta t2<S\_off\Delta t1$) for example, the contrast $(S\_on\Delta t1)/(S\_off\Delta t1)$ of the detection signal at the delay stage $\Delta t1$ is not necessarily larger than the contrast $(S\_on\Delta t2)/(S\_off\Delta t2)$ of the detection signal at the delay stage $\Delta t2$.

That is to say, in this case, it is considered that the intensity of the detection signal acquired by irradiation of pulsed laser in the on-operation of irradiation by the ON-OFF switching unit 21 just before an off-operation of irradiation by the ON-OFF switching unit 21 does not completely attenuate at the delay stage $\Delta t1$ in the off-operation of irradiation by the ON-OFF switching unit 21. The intensity of the remaining detection signal is added to the intensity of a detection signal acquired by the irradiation of the pulsed laser in the on-operation of irradiation by the ON-OFF switching unit 21, so that the intensity of the resulting detection signal becomes large while its contrast becomes weak. As a result, an optimum image is not necessarily formed even though the intensities of the detection signal at this delay stage is used.

And, there may be the case where the contrast $(S\_on\Delta t1)/(S\_off\Delta t1)$ of the detection signal at the delay stage $\Delta t1$ is smaller than the contrast $(S\_on\Delta t2)/(S\_off\Delta t2)$ of the detection signal at the delay stage $\Delta t2$. In this case, it is considered that the intensity of the detection signal acquired by irradiation of pulsed laser in the on-operation of the irradiation by the ON-OFF switching unit 21 just before an off-operation of irradiation by the ON-OFF switching unit 21 attenuates at the delay stage Δt2 in the off-operation of irradiation by the ON-OFF switching unit 21 yet more than it attenuates at the delay stage Δt1 in the off-operation of irradiation by the ON-OFF switching unit 21.

As a result, the contrast of the detection signal is higher at the delay stage Δt2 than at the delay stage Δt1 even though the intensity of the detection signal detected at the delay stage Δt2 in the on-operation of irradiation by the ON-OFF switching unit 21 is smaller than the intensity of the detection signal detected at the delay stage Δt1 in the on-operation of irradiation by the ON-OFF switching unit 21, so that there can occur the case where a more optimum image can be formed with the intensity of the detection signal at the delay stage Δt2 than at the delay stage Δt1.

Accordingly, in the laser scanning type observation apparatus according to the second embodiment, the decision unit 18 is configured: to compare the contrast of a detection signal detected at the delay stage Δt1 with the contrast of the detection signal detected at the delay stage Δt2 in the case where the intensity of the detection signal detected at the delay stage Δt1 in the off-operation of irradiation by the ON-OFF switching unit 21 is larger than the intensity of the detection signal detected at the delay stage Δt2 in the off-operation of irradiation by the ON-OFF switching unit 21 (S_offΔt2<S_offΔt1) for example; and to decide that a delay stage with large contrast of these delay stages is an optimum delay stage for image formation.

In addition, a detection signal outputted by the light detecting unit 12 contains dark current originally existing in the light detecting unit 12 independently of irradiation of pulsed laser, as noise.

In this case, if dark current is removed in forming an image with a sampled detection signal, then image quality can be improved yet more.

Accordingly, the decision unit 18 further detects background noise using data on the intensities of the detection signal at respective delay stages that are set by the multi-stage delay setting unit 17 in the off-operation of irradiation by the ON-OFF switching unit 21.

As described above, the laser scanning type observation apparatus according to the second embodiment is provided with the ON-OFF switching unit 21, so that it becomes possible to sample also an electric signal into which light is photo-electrically converted by the light detecting unit 12, as a detection signal, when pulsed laser is not irradiated to the test object 30. Also, the decision unit 18 not only can compare the intensities of a detection signal with one another but also can calculate contrasts of detection signals which are detected in the on-operation of irradiation to the test object 30 by the ON-OFF switching unit 21 and in the off-operation of irradiation to the test object 30 by the ON-OFF switching unit 21 respectively. As a result, it is possible to adjust sampling timing to optimum sampling timing for improving image quality, the optimum sampling time being determined by taking factors except for intensity of detection signal, such as contrast value and background noise, into consideration.

Also, in the laser scanning type observation apparatus according to the second embodiment, it is possible to acquire a signal value when pulsed laser is not irradiated to the test object 30, so that it is also possible to detect a background noise which is a noise existing when pulsed laser is not irradiated to the test object 30.

That is to say, it is possible to measure a value of a background noise in each setting of timing in parallel with adjustment of sampling timing. As a result, it becomes possible to remove that noise in forming an image by the image forming unit 20, so that it is possible to improve image quality yet more.

The Third Embodiment

Figure 11:
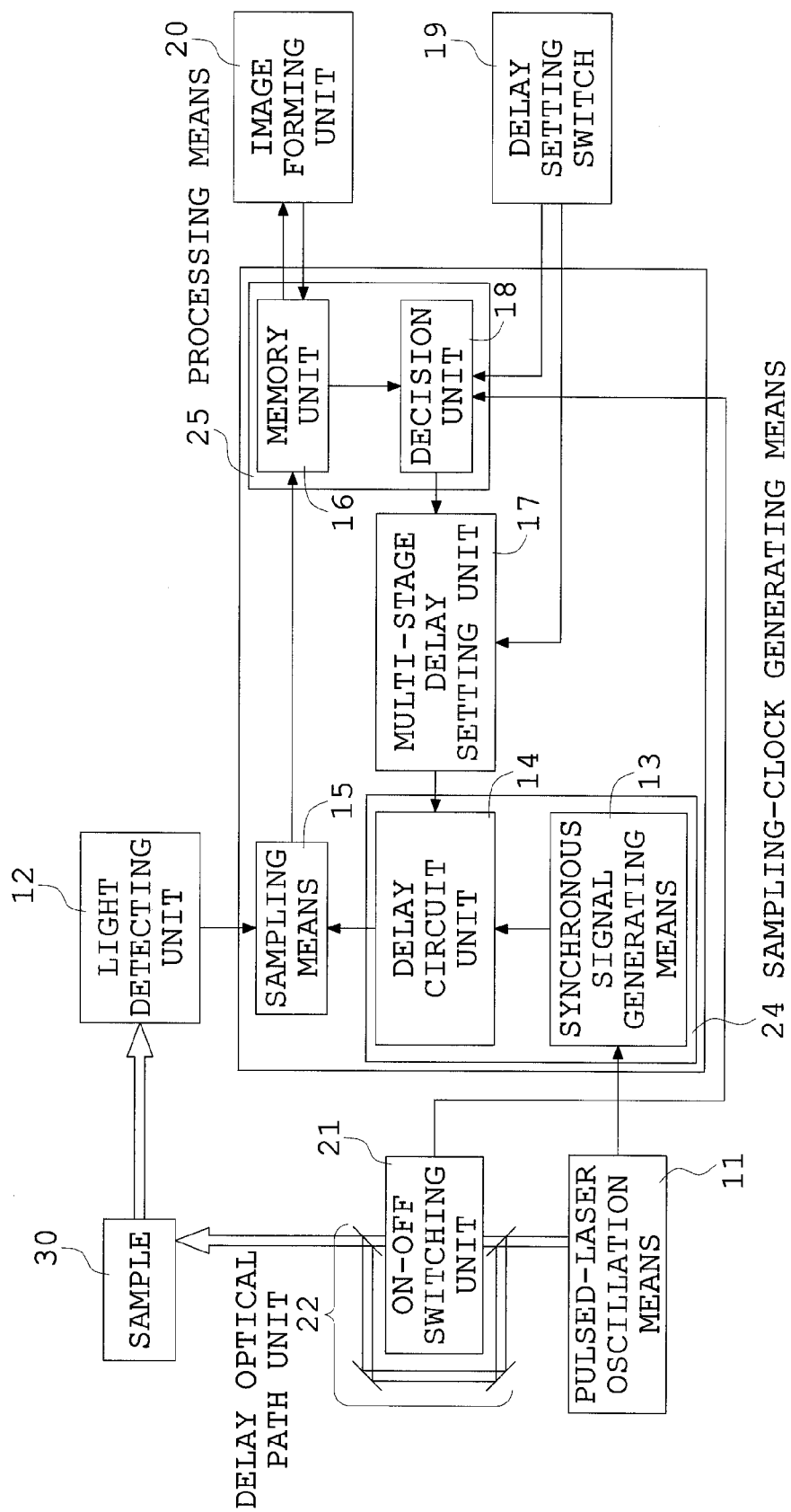
FIG. 11 is a block diagram schematically showing a structure of a laser scanning type observation apparatus according to a third embodiment of the present invention.
Figure 12:
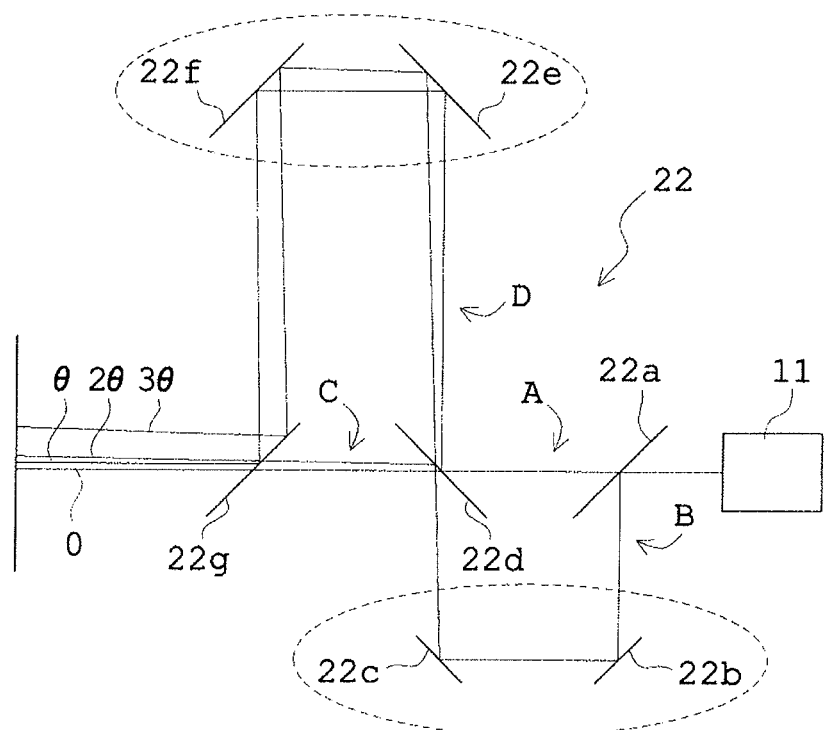
FIG. 12 is an explanatory view showing one example of a delay optical path unit provided for the laser scanning type observation apparatus shown in FIG. 11.
Figure 13A:
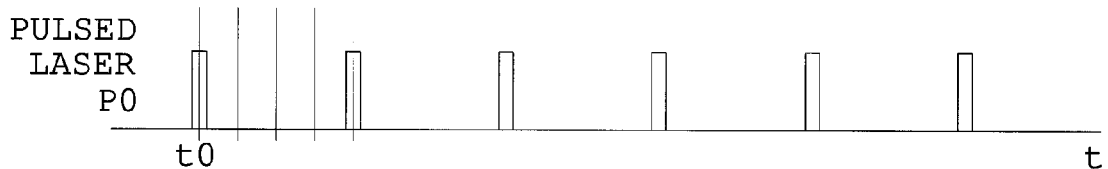
FIGS. 13A to 13E are explanatory views showing a time delay of pulsed laser caused by the delay optical path unit shown in FIG. 12 in the laser scanning type observation apparatus shown in FIG. 11.
Figure 13B:
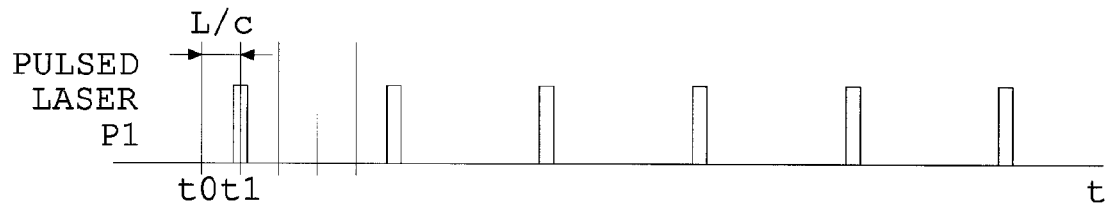
Figure 13C:
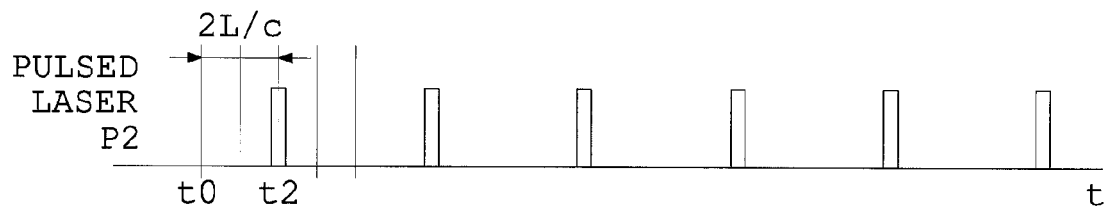
Figure 13D:
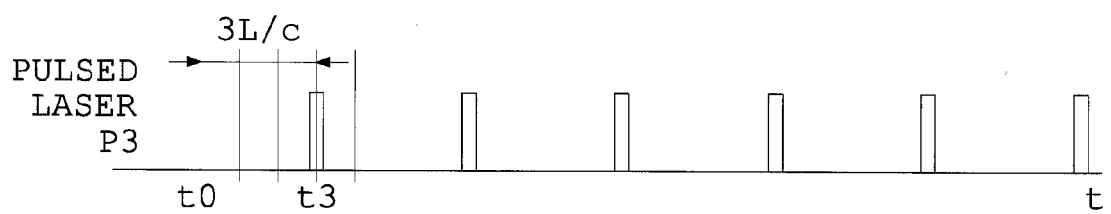
Figure 13E:
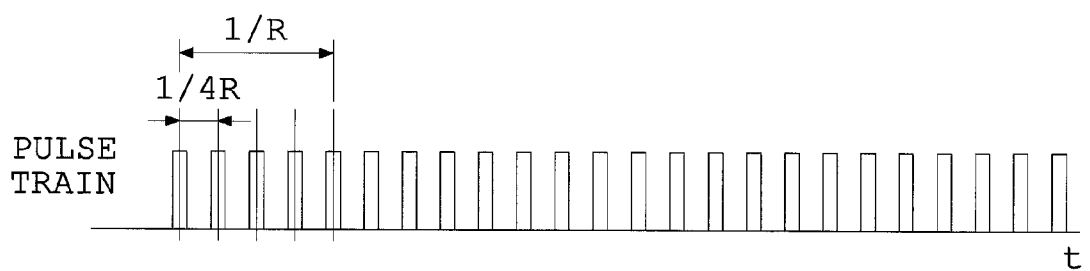

FIG. 11 is a block diagram schematically showing a structure of a laser scanning type observation apparatus according to a third embodiment of the present invention. FIG. 12 is an explanatory view showing one example of a delay optical path unit provided for the laser scanning type observation apparatus shown in FIG. 11. FIGS. 13A to 13E are explanatory views showing a time delay of pulsed laser delayed by the delay optical path unit shown in FIG. 12 in the laser scanning type observation apparatus shown in FIG. 11, FIG. 13A is a view showing pulsed laser passing through a first optical path of the delay optical path unit, FIG. 13B is a view showing pulsed laser passing through a second optical path of the delay optical path unit to be delayed, FIG. 13C is a view showing pulsed laser passing through a third optical path of the delay optical path unit to be delayed, FIG. 13D is a view showing pulsed laser passing through a fourth optical path of the delay optical path unit to be delayed, and FIG. 13E is a view showing a pulse train with a period that is multiplied by making pulsed lasers pass through the first to fourth optical paths of the delay optical path unit.

A laser scanning type observation apparatus according to the present embodiment not only has the constitution of the laser scanning type observation apparatus according to the second embodiment as shown in FIG. 9 but also includes: a delay optical path unit 22; and the ON-OFF switching unit 21 which is placed on at least one of optical paths branching at the delay optical path unit 22, as shown in FIG. 11. And, the laser scanning type observation apparatus according to the present embodiment is configured to operate in such a way that the on-operation of irradiation and the off-operation of irradiation are changed to each other within one period of oscillation of pulsed laser by the pulsed-laser oscillation means 11, the on-operation of irradiation causing irradiation of pulsed laser to the test object 30 and the off-operation of irradiation causing a stop of irradiation of pulsed laser to the test object 30.

The delay optical path unit 22 is configured: to split an optical path of pulsed laser emitted by the pulsed-laser oscillation means 11 into at least two or more optical paths; and to multiply a period of the pulsed laser emitted by the pulsed-laser oscillation means 11 with a difference between the different optical paths in length to irradiate a pulsed laser with the multiplied period to the test object 30.

Now, a structure of the delay optical path unit 22 is explained in detail using FIG. 12. FIG. 12 is an explanatory view showing one example of the delay optical path unit. Besides, in the example shown in FIG. 12, the delay optical path unit 22 has four optical paths which are different from one another in length.

The delay optical path unit 22 in the example shown in FIG. 12 includes a beam splitter 22a, mirrors 22b and 22c, a beam splitter 22d, mirrors 22e and 22f, and a beam splitter 22g.

The beam splitter 22a splits pulsed laser into two optical paths (optical path A and optical B) which are different from each other in length. The angle of rotation from standard state to one of the mirrors 22b and 22c is θ. The mirrors 22b and 22c are arranged: to deflect pulsed laser traveling on one optical path (optical path B) of the optical paths A and B at an angle of 2θ relative to pulsed laser traveling on the other optical path (optical path A); and to delay the pulsed laser traveling on the optical path B so as to make a difference L between the lengths of the optical paths A and B, the optical paths A and B being made to branch by the beam splitter 22a. The beam splitter 22d combines the pulsed lasers that branch through the beam splitter 22a to travel on the two optical paths (optical path A and optical path B) respectively and then further splits pulsed laser into two optical paths different from each other in length. The angle of rotation from standard state of one of the mirrors 22e and 22f is θ/2. The mirrors 22e and 22f are arranged: to deflect pulsed laser traveling on one optical path (optical path D) of the optical paths C and D at an angle of θ relative to pulsed laser traveling on the other optical path (optical path C); and to delay the pulsed laser traveling on the optical path D so as to make a difference 2L between the lengths of the optical paths C and D, the optical paths C and D being made to branch by the beam splitter 22d. The beam splitter 22g combines the pulsed lasers traveling on the two optical paths (optical path C and optical path D).

Now, operation effects which are peculiar to the laser scanning type observation apparatus according to the third embodiment having such a constitution are explained in the case where the delay optical path unit 22 is configured as shown in FIG. 12.

A pulsed laser emitted by the pulsed laser oscillating unit 11 is split into: a pulsed laser P0 traveling on the optical paths A to C; a pulsed laser P1 traveling on the optical paths B to C; a pulsed laser P2 traveling on the optical paths A to D; and a pulsed laser P3 traveling on the optical paths B to D. And, when the letter "c" symbolizes the speed of the pulsed lasers, the pulsed laser P1 is a light beam which is delayed by L/c relative to the pulsed laser P0 and deflected at an angle of 2θ relative to the pulsed laser P0, the pulsed laser P2 is a light beam which is delayed by 2 L/c relative to the pulsed laser P0 and deflected at an angle of 0 relative to the pulsed laser P0, and the pulsed laser P3 is a light beam which is delayed by 3 L/c relative to the pulsed laser P0 and deflected at an angle of 3θ relative to the pulsed laser P0. In this case, when the laser scanning type observation apparatus is configured so that the difference L between the optical paths in length satisfies a condition, L/c=¼R, with respect to a repeat frequency R of the pulsed-laser oscillation means 11, a pulsed laser emitted by the pulsed-laser oscillation means 11 is chronologically multiplexed with a multiplied period of the repeat frequency 4R as shown in FIG. 13E and becomes a light beam spatially multiplexed with an interval of θ between the deflection angles to be irradiated to the test object 30.

As a result, according to the laser scanning type observation apparatus of the present embodiment, it is possible to carry out multiplexing into four pulsed lasers with one oscillation of pulsed laser, so that an amount of acquiring signals per unit time can be increased and an image-forming process can be performed at high speed.

As a result, a series of flows can be performed at high speed, so that it becomes possible to optimize sampling timing in an inter-frame operation or the like, while a user does not have to pay attention to the optimization of sampling timing.

Also, in the laser scanning type observation apparatus according to the present embodiment, the ON-OFF switching unit 21 is placed on at least one of the optical paths branching in the delay optical path unit 22, so that it becomes possible to change irradiation of laser and non-irradiation of laser to each other at high speed by changing the on-operation of irradiation and the off-operation of irradiation to each other one time by the ON-OFF switching unit 21 to intercept only light that travels on a part of the optical paths. That is to say, it becomes possible to change irradiation of laser to the test object 30 and non-irradiation of pulsed laser to the test object 30 to each other many times within one period of oscillation of pulsed laser. Also, it is possible to detect contrasts for multiplexed pulsed laser and background noise to improve qualities of formed images.

Besides, the delay optical path unit 22 shown in FIG. 12 is merely one example, and delay optical path units for the present invention may have any structures making it possible for the laser scanning type observation apparatus to operate in such a way that: a period of pulsed laser emitted by the pulsed-laser oscillation means 11 is multiplied by differences between the different optical paths in length; and pulsed laser with the multiplied period is irradiated to the test object 30. For example, another structure disclosed in the publication of unexamined applications WO/2011052248, which is an application by the present applicant, may be used for the present invention.

The Fourth Embodiment

Figure 14:
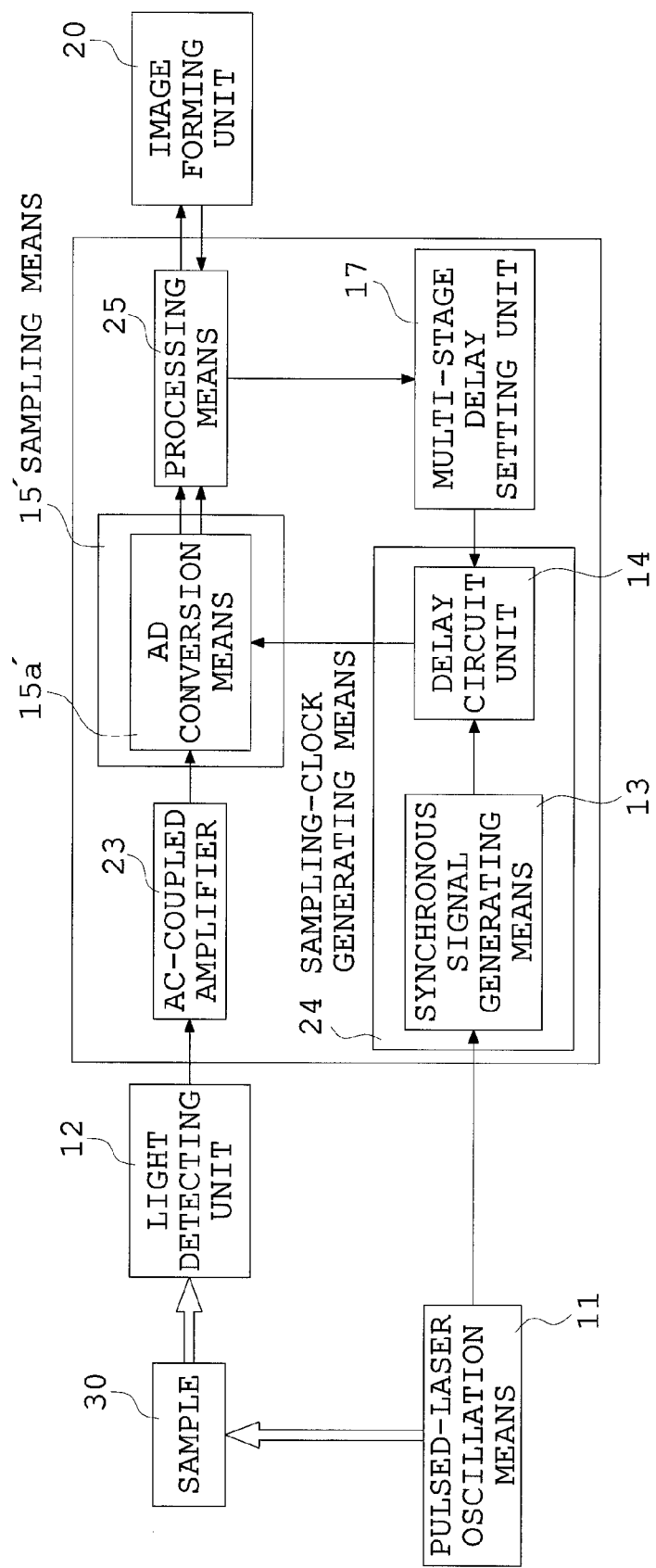
FIG. 14 is a block diagram schematically showing a structure of a laser scanning microscope apparatus according to a fourth embodiment of the present invention.
Figure 15:
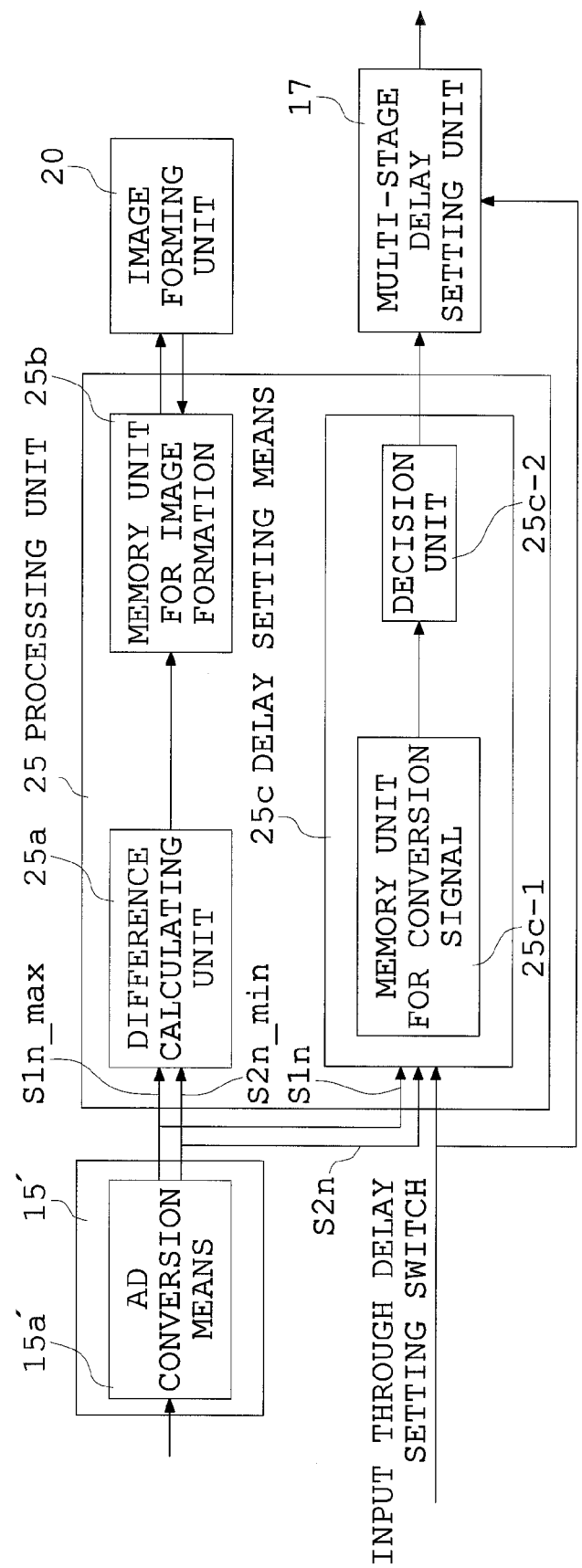
FIG. 15 is a block diagram showing a main part of a structure of the laser scanning microscope apparatus shown in FIG. 14.
Figure 16:
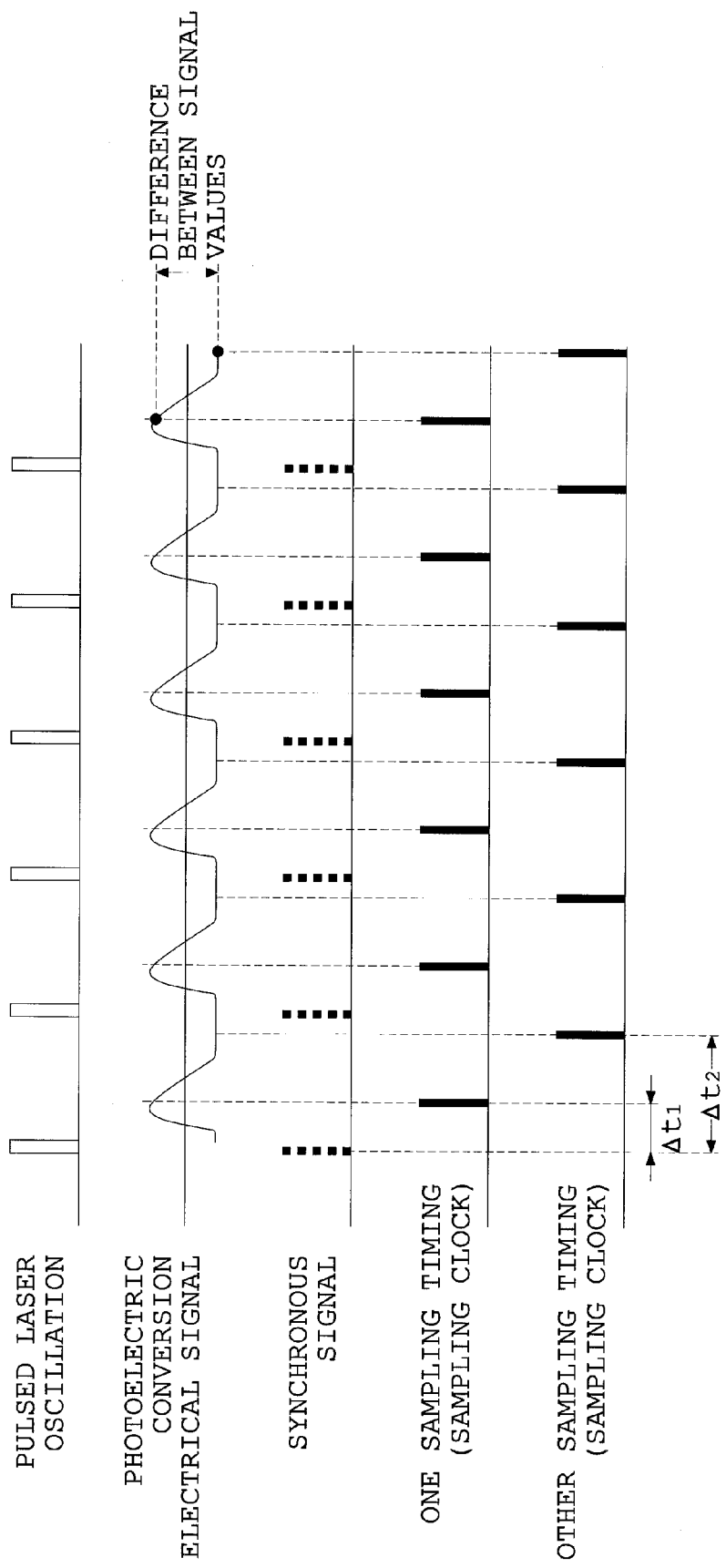
FIG. 16 is an explanatory view showing one example of timing charts of oscillation of pulsed laser, an electric signal into which light is photo-electrically converted by the light detecting unit and which is outputted by the light detecting unit, a synchronous signal synchronizing with the oscillation of the pulsed laser, a sampling clock for sampling via the first system of the AD converter means, the sampling clock for sampling via the first system of the AD converter means being outputted with a delay of a set amount of time relative to the synchronous signal, and a sampling clock for sampling via the second system of the AD converter means, the sampling clock for sampling via the second system of the AD converter means being outputted with a delay of a set amount of time relative to the synchronous signals, in the laser scanning microscope apparatus shown in FIG. 14.
Figure 17:
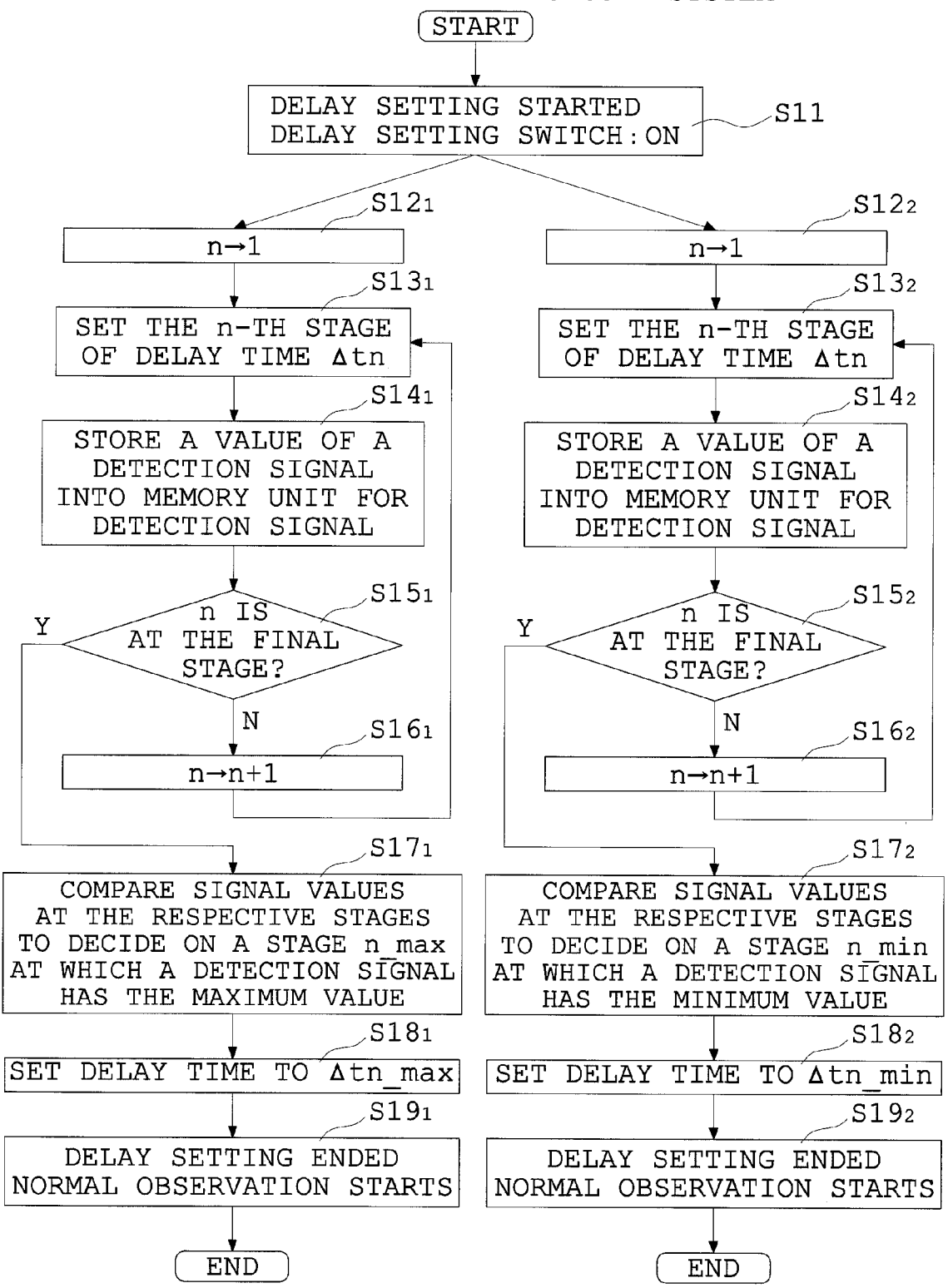
FIG. 17 is a flow chart showing one example of procedures for setting delay time for optimizing timings at which the detection signal is sampled by the AD converter means of two systems respectively, in the laser scanning microscope apparatus shown in FIG. 14.

FIG. 14 is a block diagram schematically showing a structure of a laser scanning microscope apparatus according to a fourth embodiment of the present invention. FIG. 15 is a block diagram showing a main part of the structure of the laser scanning microscope apparatus shown in FIG. 14. FIG. 16 is an explanatory view showing one example of timing charts of oscillation of pulsed laser, an electric signal into which light is photo-electrically converted by the light detecting unit and which is outputted by the light detecting unit, a synchronous signal synchronizing with the oscillation of the pulsed laser, a sampling clock for sampling via the first system of the AD converter means, the sampling clock for sampling via the first system of the AD converter means being outputted with a delay of a set amount of time relative to the synchronous signals, and a sampling clock for sampling via the second system of the AD converter means, the sampling clock for sampling via the second system of the AD converter means being outputted with a delay of a set amount of time relative to the synchronous signals, in the laser scanning microscope apparatus shown in FIG. 14. FIG. 17 is a flow chart showing one example of procedures for setting delay time for optimizing timings at which the detection signal is sampled by the AD converter means of two systems respectively, in the laser scanning microscope apparatus shown in FIG. 14.

A laser scanning microscope according to the present embodiment includes: the pulsed-laser oscillation means 11; the light detecting unit 12; the AC-coupled amplifier 23; the sampling-clock generating means 24; a sampling means 15'; the processing unit 25; and the multi-stage delay setting unit 17, as shown in FIG. 14. Besides, the reference numeral 20 shown in FIG. 14 denotes an image forming unit which forms a digital image using the intensities of digital signals read out from the memory 25b for image formation (refer to FIG. 15) provided for the processing unit 25 as pixel values, and the reference numeral 30 shown in FIG. 14 denotes a test object (sample).

The pulsed-laser oscillation means 11 and the light detecting unit 12 for the fourth embodiment are configured in approximately the same manners as the pulsed-laser oscillation means 11 and the light detecting units 12 for the laser scanning type observation apparatuses according to the first to third embodiments are, respectively.

The sampling-clock generating means 24 includes the synchronous signal generating means 13 and the delay circuit unit 14.

The synchronous signal generating means 13 and the delay circuit unit 14 for the fourth embodiment are configured in approximately the same manners as the synchronous signal generating means 13 and the delay circuit units 14 for the laser scanning type observation apparatuses according to the first to third embodiments are, respectively.

The multi-stage delay setting unit 17 for the fourth embodiment is configured in approximately the same manner as the multi-stage delay setting units 17 for the laser scanning type observation apparatuses according to the first to third embodiments are.

The AC-coupled amplifier 23 amplifies a current signal outputted by the light detecting unit 12 and outputs the amplified signal as a voltage signal.

The sampling means 15' is configured to include an A/D converter means 15a' provided with two systems which convert an analog signal outputted by the light detecting unit 12 into a digital signal to sample the digital signal while the signal conversion and the sampling of the digital signal are synchronizing with a trigger signal outputted by the delay circuit unit 14.

The processing unit 25 includes a difference calculating unit 25a, the memory unit 25b for image formation, and the delay setting means 25c, as shown in FIG. 15.

The difference calculating unit 25a outputs as a signal value for image formation a difference between detection signals (S1$n$_max, S2$n$_min, where n_max and n_min are natural numbers) which are sampled by the AD converter means 15a' of two systems at timing set by the delay setting means 25c.

The memory unit 25b for image formation stores (memorizes) the difference between the detection signals from the AD converter means 15a' of two systems which is outputted by the difference calculating unit 25a (the difference between the detection signals from the AD converter means 15a' of two systems being |S1$n$_max−S2$n$_min|).

The delay setting means 25c includes a memory unit 25c-1 for conversion signal and a decision unit 25c-2.

The memory unit 25c-1 for conversion signal stores (memorizes) detection signals (S1$n$, S2$n$, where n denotes a natural number) from the AD converter means 15a' of two systems.

The decision unit 25c-2 compares data on the intensities of the digital signal at the respective delay stages with one another to determine an optimum delay stage (delay time) for image formation for each system of the AD converter means 15a', the intensities of the digital signal at the respective delay stages for each system of the A/D converter means 15a' being sampled by each of the two systems of the AD converter means 15a' while the respective samplings of the digital signals by the AD converter means 15a' of two systems are synchronizing with a trigger signal outputted by the delay circuit unit 14 in accordance with two or more stages of delay time which are set by the multi-stage delay setting unit 17 and the data on the intensities of the digital signal at the respective delay stages in each system of the A/D converter means 15a' being stored (memorized) by the memory unit 25c-1 for conversion signal.

More specifically, as shown in FIG. 17 for example, the decision unit 25c-2 compares the intensities of the detection signal at the delay stages which are sampled by the first system of the AD converter means 15a' to be stored (memorized) by the memory unit 25c-1 for conversion signal, with one another, and compares the intensities of the detection signal at the delay stages which are sampled by the second system of the AD converter means 15a' to be stored (memorized) by the memory unit 25c-1 for conversion signal, with one another, the delay stages being set by the multi-stage delay setting unit 17. And the, the decision unit 25c-2 determines optimum delay stages for image formation (or, timing at which a detection signal is sampled by each of the first and second systems of the AD converter means 15a') and then sends to the multi-stage delay setting unit 17 a signal for communicating delay stages determined by the decision unit 25c-2 (in FIG. 17 for example, the decision unit 25c-2 decides on a delay stage $\Delta$tn_max at which a detection signal has the largest intensity in delay stages set by the multi-stage delay setting unit 17, as sampling timing for the first system of the AD converter means 15a', and the decision unit 25c-2 decides on a delay stage $\Delta$tn_min at which a detection signal has the smallest intensity in delay stages set by the multi-stage delay setting unit 17, as sampling timing for the second system of the AD converter means 15a').

The delay setting means 25c having such a constitution adjusts an amount of delay of timing for sampling for each of two systems of the AD converter means 15a' to set the amounts of delay of timing for sampling, relative to each of the two systems of the AD converter means 15a'.

Besides, in the example shown in FIG. 17, amounts of delays of timings for samplings by the two systems of the AD converter means 15a' are adjusted so that the two systems of the AD converter means 15a' are set to the delay stage $\Delta$tn_max at which the detection signal has the maximum intensity and to the delay stage $\Delta$tn_min at which the detection signal has the minimum intensity, as respective sampling timings for the two systems of the AD converter means 15a', respectively. However, the delay setting means 25c may adjust and set the two systems of the AD converter means 15a' so that an amount of delay of timing for sampling by one of the two systems of the AD converter means 15a' is made to differ from an amount of delay of timing for sampling by the other of the two systems of the AD converter means 15a' by a half of one period of a frequency of oscillation of pulsed laser.

The multi-stage delay setting unit 17 sets delay time for delaying a clock signal by the delay circuit unit 14, to delay time corresponding to the optimum delay stage for image formation which is determined by the decision unit 25c-2.

Besides, in the laser scanning microscope apparatus according to the present embodiment, a delay setting switch which is not shown in the drawings is further connected to the multi-stage delay setting unit 17 and the decision unit 25c-2, and an operation of the delay setting switch by a user can makes the multi-stage delay setting unit 17 and the decision unit 25c-2 newly perform a setting process for delay time corresponding to an optimum delay stage for image formation, at any time.

A procedure for setting delay time for the laser scanning microscope apparatus according to the fourth embodiment having such a constitution is explained using FIG. 17.

A user switches on the delay setting switch which is not shown in the drawings (Step S11). As a result, the multi-stage delay setting unit 17 and the decision unit 25c-2 newly start a process for setting a delay stage for sampling timing for each of two systems of the AD converter means 15a' in each system.

More specifically, the multi-stage delay setting unit 17 sets the delay circuit unit 14 to a plurality of delay stages $\Delta$tn (n is a natural number) to be set (Steps S13$_1$ and S13$_2$). As a result, the delay circuit unit 14 delays a synchronous signal outputted by the synchronous signal generating means 13 by an amount of time corresponding to each of the delay stages $\Delta$tn which are set by the multi-stage delay setting unit 17, and then the delay circuit unit 14 outputs a trigger signal.

Each of the first and second systems of the AD converter means 15a' samples a digital detection signal outputted by the light detecting unity 12 while the samplings of the digital detection signals by the two systems of the AD converter means $15a'$ are synchronizing with a trigger signal outputted by the delay circuit unit 14. And then, the memory unit $25c$-1 for conversion signal in the processing unit 25 stores (memorizes) digital detection signals which are sampled by the first and second systems of the AD converter means $15a'$ respectively (Steps $S14_1$ and $S14_2$).

The processes of these steps $S13_1$ $S13_2$ to $S14_1$ $S14_2$ are repeated until the final delay stage of the delay stages Δtn comes (Steps $S15_1$, $S15_2$, $S16_1$, and $S16_2$).

After the final delay stage of the delay stages Δtn comes, the decision unit $25c$-2 compares data on the intensities of each of the digital detection signals at the respective delay stages with one another, the data on the intensities of each of the digital detection signals at the respective delay stages being stored by the memory unit $25c$-1 for conversion signal. And, the decision unit $25c$-2 decides that the delay stage nmax at which the detection signal has the maximum intensity is an optimum delay stage for image formation, in the first system (Step $S17_1$). Also, the decision unit $25c$-2 decides that the delay stage n_min at which the detection signal has the minimum intensity is an optimum delay stage for image formation, in the second system (Step $S17_2$).

Next, the multi-stage delay setting unit 17 sets the delay time Δtn#max for delaying clock signal by the delay circuit unit 14 and the delay time Δtn#min for delaying clock signal by the delay circuit unit 14, to delay times corresponding to the optimum delay stages for image formation determined by the decision unit $25c$-2, respectively (Steps $S18_1$ and $S18_2$). As a result, the process for setting delay stage by the multi-stage delay setting unit 17 and the decision unit $25c$-2 finishes. In observation after the setting process finishes, a setting of delay time for the delay circuit unit 14 is fixed at the optimum delay time for observation (in the example shown in FIG. 16, at Δt1 for the first system and at Δt2 for the second system).

Each of the two systems of the AD converter means $15a'$ converts into a digital signal an analog detection signal which is outputted by the light detecting unit 12 and amplified to be outputted by the AC-coupled amplifier 23, while the conversion of the analog detection signal into the digital signal by each of the two systems of the AD converter means $15a'$ is synchronizing with a sampling clock on the basis of the delay time (Δt1, Δt2) for each system at which the setting of delay time for the delay circuit unit 14 is fixed.

The difference calculating unit $25a$ calculates a difference between the detection signals into which the analog signals are converted by the two systems of the AD converter means $15a'$ respectively, and then the difference calculating unit $25a$ outputs the difference between the detection signals as a signal value for image formation. The outputted signal value for image formation is stored (memorized) by the memory unit $25b$ for image formation.

The image forming unit 20 forms a digital image using the intensity of the digital signals read out from the memory unit $25b$ for image formation as a pixel value.

In the laser scanning microscope apparatus according to the fourth embodiment, the sampling means 15' includes the AD converter means $15a'$ of two systems which: perform sampling while timing of the sampling is synchronizing with an oscillation frequency of pulsed laser, and the processing unit 16 includes: the delay setting means $25c$ which can adjust the delay circuit unit 14 to set an amount of delay time of sampling timing for each of the two systems of the AD converter means $15a'$ in each of the two systems; and the difference calculating unit $25a$ which outputs a difference between detection signals from the AD converter means $15a'$ of two systems as a signal value for image formation, the detection signals from the AD converter means $15a'$ of two systems being sampled by the AD converter means $15a'$ of two systems at timings set by the delay setting means $25c$. As a result, the processes of: sampling the voltage signal at timing at which the waveform of the voltage signal amplified to be outputted by the AC-coupled amplifier 23 shows a peak by the first system of the AD converter means $15a'$; sampling the voltage signal at timing at which the waveform of the voltage signal amplified to be outputted by the AC-coupled amplifier 23 shows dip by the second system of the AD converter means $15a'$; and calculating the difference between the signals sampled by the two systems respectively make it possible to acquire its original peak value even though the magnitudes (peak values) of the detection signals amplified by the AC-coupled amplifier 23 are half as large as its original peak value. As a result, even in the case where feeble fluorescence is detected for example, the influence of peak value of an adjacent wave is reduced, so that an accuracy of image quality is improved.

Also, in the laser scanning microscope apparatus according to the fourth embodiment, the delay setting means $25c$ adjusts an amount of a delay time of sampling timing for the first system of the AD converter means $15a'$ of two systems so that a detection signal from the first system of the AD converter means $15a'$ has the maximum intensity in sampling the detection signal, and the delay setting means $25c$ adjusts an amount of a delay time of sampling timing for the second system of the AD converter means $15a'$ of two systems so that the detection signal from the second system of the AD converter means $15a'$ has the minimum intensity, in sampling the detection signal. As a result, even if a detection signal which is amplified by the AC-coupled amplifier 23 to be outputted is used, it is possible to acquire its original peak value high accurately, so that it is possible to improve an accuracy of image quality yet more.

Also, in the laser scanning microscope apparatus according to the fourth embodiment, the delay setting means $25c$ may adjust amounts of delays for sampling timings for the two systems of the AD converter means $15a'$ so that timing at which one of the two systems of the AD converter means $15a'$ samples the detection signal differs from timing at which the other of the two systems of the AD converter means $15a'$ samples the detection signal by a half of a period of an oscillation frequency of pulsed laser.

Such a manner makes it easy for the first system of the AD converter means $15a'$ to sample a voltage signal at timing at which the waveform of the voltage signal amplified to be outputted by the AC-coupled amplifier 23 shows a peak approximately and makes it easy for the second system of the AD converter means $15a'$ to sample the voltage signal at timing at which the waveform of the voltage signal amplified to be outputted by the AC-coupled amplifier 23 shows dip approximately, for example.

Besides, needles to say, the laser scanning microscope apparatus according to the fourth embodiment may be configured: to include an ON-OFF switching unit which change an on-operation of irradiation and an off-operation of irradiation to each other, the on-operation of irradiation causing irradiation of pulsed laser emitted by the pulsed-laser oscillation means 11 to an test object and the off-operation of irradiation causing a stop of irradiation of pulsed laser emitted by the pulsed-laser oscillation means 11 to the test object; and to detect a detection signal while the number of sampling timings is being thinned, or the laser scanning microscope apparatus according to the fourth embodiment may be configured to include a delay optical path unit (which is omitted in the drawings and) which: splits an optical path of pulsed laser emitted by the pulsed-laser oscillation means 11 into at least two or more optical paths; multiplies a period of the oscillation of the pulsed laser emitted by the pulsed-laser oscillation means 11 with a difference between the different optical paths in length; and irradiates pulsed laser with the multiplied frequency to a test object 30, so as to multiply sampling timing, as well as the laser scanning type observation apparatuses according to the first to third embodiments. In this case, the processing unit 25 in the laser scanning microscope apparatus is preferably configured to be capable of dealing with multiplication or frequency division of sampling clock.

Figure 18:
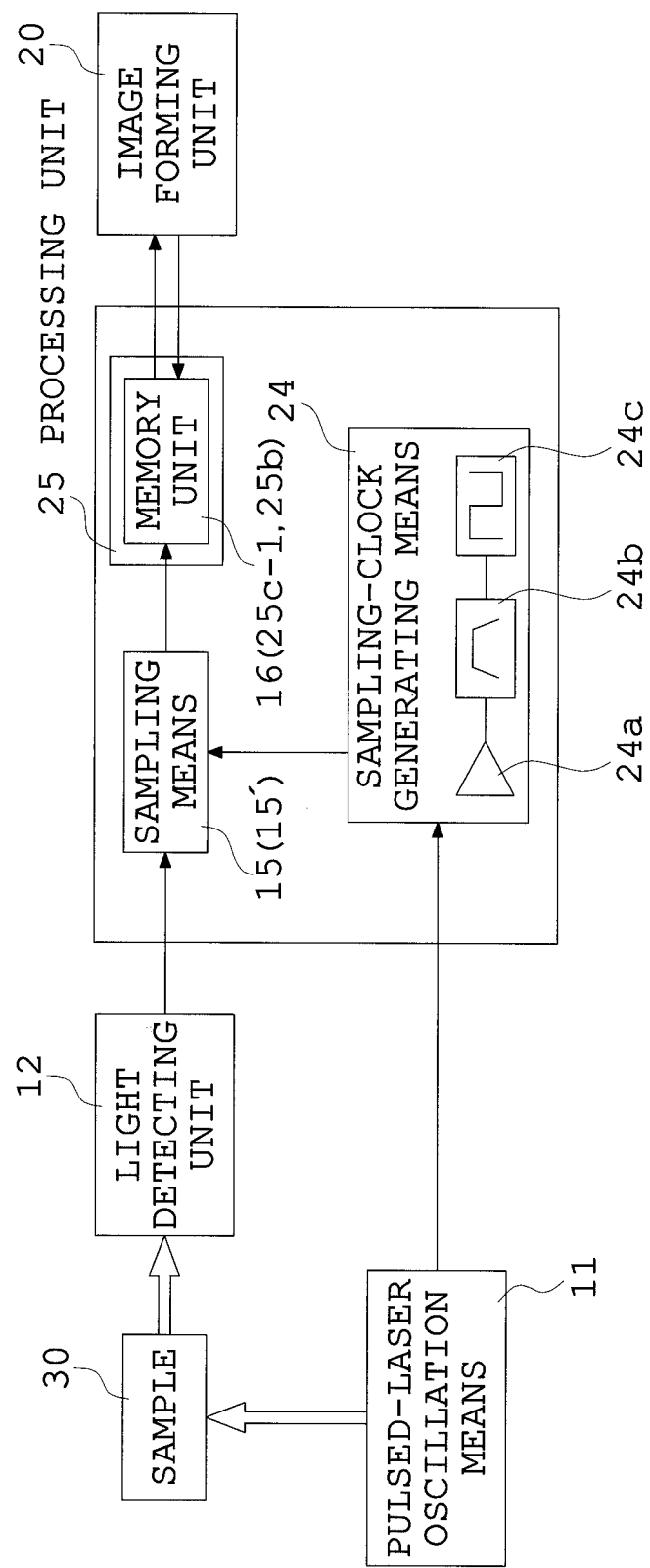
FIG. 18 is a block diagram schematically showing a structure for reducing noise that is contained in monitor signals used for sampling clock in the sampling clock generating means provided for the laser scanning type observation apparatus (laser scanning microscope apparatus) according to each of the above-described embodiments.

Up to now, the embodiments of laser scanning type observation apparatuses according to the present invention have been explained. In addition, in a laser scanning type observation apparatus (laser scanning microscope apparatus) of each of the above-described embodiments according to the present invention, as shown in FIG. 18, it is preferred that: the sampling-clock generating means 24 includes a clock device 24c reshaping a signal for a detection of pulsed laser oscillation by the pulsed-laser oscillation means 11, a high magnification amplifier 24a, and a band pass filter 24b; and the sampling-clock generating means 24 is configured to operate in such a way that the high magnification amplifier 24a and the band pass filter 24b send to the clock device 24c a signal acquired by removing a set frequency component from a monitor signal or the like which is used for a detection of pulsed laser oscillation by the pulsed-laser oscillation means 11, the set frequency component being a component different from a oscillation frequency of the pulsed laser, such as a higher harmonic frequency component. And, such a configuration makes it possible to sample a detection signal such as fluorescence with high accuracy while a noise which is contained in a monitor signal or the like used for sampling clock is reduced, even though the monitor signal synchronizing with pulsed laser is used as sampling clock.

In order to certainly detect a peak of a detected waveform through fluorescence or the like, the use of sampling clock synchronizing with an oscillation mode of a laser light source is required.

Like the laser scanning type observation apparatuses disclosed in the above Japanese Granted Patent No. 4667571 and Japanese Patent KOKAI NO. 2007-102235 respectively, a monitor signal from a pulsed laser oscillator or a time waveform signal generated by a light detecting device detecting a minute amount of an output laser beam taken by a half mirror is reshaped by a clock device, in the prior art.

However, the above signal for a detection of pulsed laser oscillation such as monitor signal really contains many noise components. It is not suitable for practical use as a sampling clock to use the signal waveform including noise components as signal waveform of sampling clock as it is.

That is to say, if the original waveform of a detection signal of pulsed laser oscillation is used as it is, a peak waveform caused by a noise appears irregularly or a peak of pulse becomes a double peak, for example. As a result, even if the original waveform of the signal such as monitor signal is reshaped by the clock device, the clock device does not work, timing at which a sampling means samples signals is wrong, and so on, so that it is difficult to detect a peak of a detected waveform acquired by detecting fluorescence or the like, and it is impossible to use the original signal containing noises, as a sampling clock for sampling a detection signal outputted by the light detecting unit.

A constitution of a laser scanning type observation apparatus shown in FIG. 18 is made in the view of such a conventional problem, and the objective of this constitution shown in FIG. 18 is to make a laser scanning type observation apparatus: making it possible to reduce noises contained in a monitor signal as sampling clock despite the use of the monitor signal synchronizing with pulsed laser as sampling clock for sampling a detection signal outputted by a light detecting unit; and making it possible to sample a detection signal for fluorescence or the like with high accuracy.

Figure 19A:
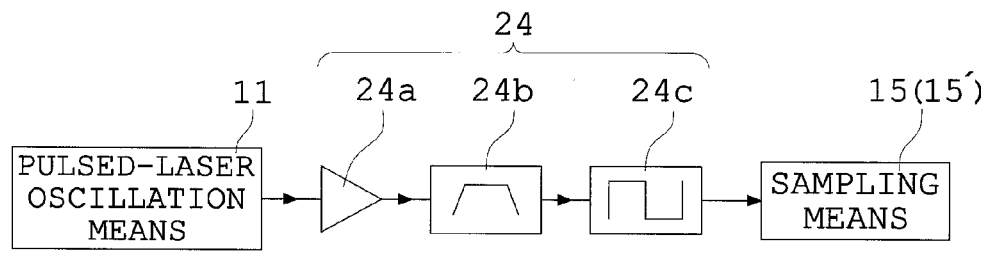
FIGS. 19A, 19B, and 19C are explanatory views showing examples of combinations of devices provided for the sampling clock generating means of the laser scanning type observation apparatus (laser scanning microscope apparatus) shown in FIG. 18.
Figure 19B:
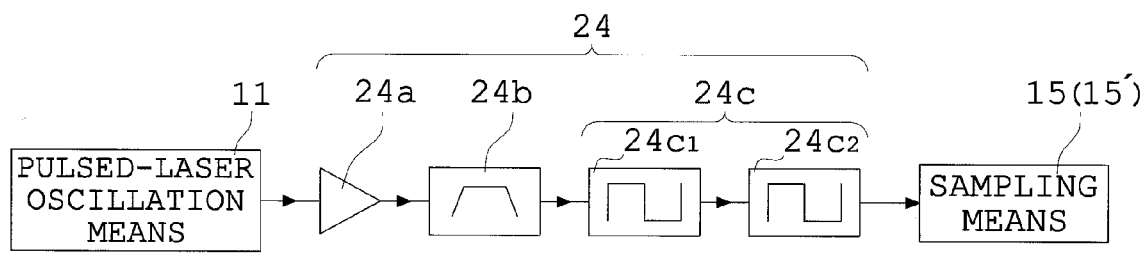
Figure 19C:
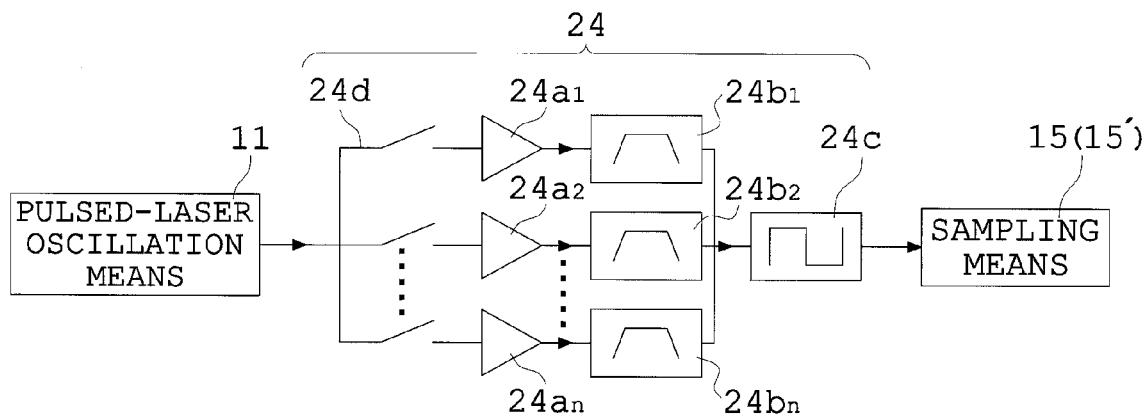
Figure 20A:
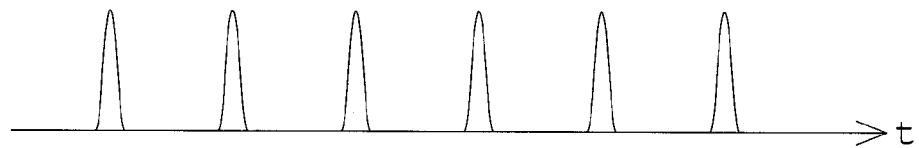
FIGS. 20A to 20D are explanatory views showing a waveform of each type of light emitted from pulsed laser oscillation to generation of sampling clock with the laser scanning type observation apparatus (laser scanning microscope apparatus) shown in FIG. 18.
Figure 20B:
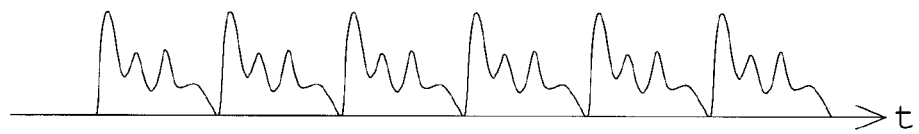
Figure 20C:
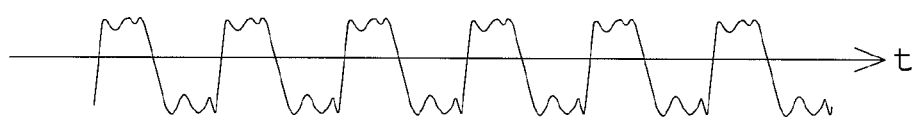
Figure 20D:

FIG. 18 is a block diagram schematically showing a structure for reducing noise that is contained in monitor signals used for sampling clock in the sampling clock generating means provided for the laser scanning type observation apparatus (laser scanning microscope apparatus) of each of the above-described embodiments. FIGS. 19A, 19B, and 19C are explanatory views showing examples of combinations of devices provided for the sampling clock generating means of the laser scanning type observation apparatus (laser scanning microscope apparatus) shown in FIG. 18, FIG. 19A is a view showing one example of the combinations, FIG. 19B is a view showing another example of the combinations, and FIG. 19C is a view showing yet another example of the combinations. FIGS. 20A to 20D are explanatory views showing a waveform of each type of light emitted from pulsed laser oscillation to generation of sampling clock with the laser scanning type observation apparatus (laser scanning microscope apparatus) shown in FIG. 18, FIG. 20A is a view showing a waveform of light of pulsed laser emitted from the pulsed-laser oscillation means, FIG. 20B is a view showing a waveform of a monitor signal from the pulsed-laser oscillation means when pulsed-laser oscillation means generates pulsed laser oscillation, FIG. 20C is a view showing a waveform of the monitor signal shown in FIG. 20B after the monitor signal passes through a high magnification amplifier provided for the synchronous signal generating means and through a band-pass filter, and FIG. 20D is a view showing a waveform of sampling clock outputted by a clock device after the signal shown in FIG. 20C is inputted into the clock device provided for the delay circuit unit.

The sampling-clock generating means 24 is provided with the high magnification amplifier 24a, the band pass filter 24b, and the clock device 24c, as shown in FIG. 19A for example.

The band pass filter 24b is composed of one of a LPF, a BPF, and a HPF or is configured in a combination of these filters, in accordance with a frequency property of the high magnification amplifier 24a. Besides, the band pass filter 24b shown in FIG. 19 is illustrated to be composed of the BPF, for the sake of convenience in explanation.

And, the high magnification amplifier 24a and the band pass filter 24b remove set frequency components except a frequency of oscillation of pulsed laser emitted by the pulsed-laser oscillation means 11, such as higher harmonic component for example, from a signal for a detection of pulsed laser oscillation by the pulsed-laser oscillation means 11 with a monitor signal or a time wavelength signal for the detection of the output laser beam, such as: a trigger output signal outputted as an electric signal synchronizing with an oscillation of the pulsed laser from the pulsed-laser oscillation means 11; and an electric signal into which a part of the pulsed laser is photo-electrically converted by a photo detector or a photo multiplier for example.

The clock device 24c is composed of an oscillator or a PLL device or is configured in a combination of these devices. And, the clock device 24c reshapes a signal having passed through the high magnification amplifier 24a and the band pass filter 24b and then outputs a clock signal.

Also, the clock device 24c has a jitter-removing function.

In addition, the clock device 24c has a wide output band range width. In the case where an oscillation frequency of pulsed laser emitted by the pulsed-laser oscillation means 11 is 80 MHz for example, the clock device 24c is configured to be capable of outputting a frequency of from 1/1000 times to 1000 times the oscillation frequency of the pulsed laser (several KHz to several GHz).

Besides, as shown in FIG. 19B for example, the clock device 24c may be configured to consist of: a first clock device $24c_1$ having a jitter-removing function; and a second clock device $24c_2$ having a wide output band range width, the first and second clock devices $24c_1$ and $24c_2$ being connected to each other in a manner of cascade connection.

Also, the high magnification amplifier 24a and the band pass filter 24b may be configured to be a plurality of pairs of high magnification amplifier $24a_{1\ (2\ to\ n)}$ (n denotes a natural number) and band pass filter $24b_{1\ (2\ to\ n)}$ (n denotes a natural number), the high magnification amplifiers $24a_{1\ (2\ to\ n)}$ being paired with the band pass filters $24b_{1\ (2\ to\ n)}$ respectively so that the pairs of the high magnification amplifier and the band pass filter are made to differ from one another in magnification and in transmission band range so as to be capable of dealing with noise levels of detection signals used for detection of oscillation of pulsed laser from the pulsed-laser oscillation means 11 (such as monitor signal or time waveform signal for a detection of the output laser beam), and the pairs of high magnification amplifier and band pass filter being arranged to be in a multistage arrangement, as shown in FIG. 19C for example. In addition, the sampling-clock generating means 24 may be configured to include a switch element 24d which switches conductive paths of a signal for detection of pulsed laser oscillation from the pulsed-laser oscillation means 11, to one another, so as to transmit the signal for detection of oscillation of pulsed laser through a pair of high magnification amplifier and band pass filter having optimum magnification and optimum transmission band range for the signal for detection of oscillation of pulsed laser among the pairs of high magnification amplifier $24a_{1\ (to\ n)}$ and band pass filter $24b_{1\ (to\ n)}$, in accordance with the noise level of the signal for detection of oscillation of pulsed lase.

A procedure for reshaping a signal for detection of oscillation of pulsed laser from the pulsed-laser oscillation means 11 (monitor signal or time waveform signal for a detection of the output laser beam) to output a sampling clock is explained using FIGS. 20A to 20D with respect to the laser scanning type observation apparatus (laser scanning microscope apparatus) according to each of the above described embodiments in which the sampling clock-generating means 24 further has such a constitution as shown in FIG. 18.

The sampling-clock generating means 24 detects oscillation of pulsed laser emitted by the pulsed-laser oscillation means 11 (refer to FIG. 20A), through a trigger output signal outputted as an electric signal synchronizing with the oscillation of the pulsed laser from the pulsed-laser oscillation means 11 or an electric signal into which a part of the pulsed laser is photo-electrically converted by a photo detector or a photo multiplier for example. As shown in FIG. 20B, an oscillation frequency component of pulsed laser mingles with a plurality of frequency components except the oscillation frequency component such as higher harmonic component in a detection signal detected by the sampling-clock generating means 24 (the monitor signal or the time waveform signal for a detection of the output pulsed laser).

If this detection signal is transmitted through the high magnification amplifier 24a and the band pass filter 24b, a plurality of the frequency components except the oscillation frequency component of pulsed laser, such as higher harmonic component causing noise, are removed from the detection signal, as shown in FIG. 20C. At this stage, the detection signal includes small waveforms as jitter.

Next, the detection signal is transmitted through the clock device 24c. As a result, the detection signal is reshaped, so that the small waveforms in the detection signal are removed from the detection signal, as shown in FIG. 20D.

In the laser scanning type observation apparatuses (laser scanning microscope apparatus) of the above described embodiments each of which is provided with the sampling-clock generating means 24 further having such a constitution as shown in FIG. 18, the sampling-clock generating means 24 includes the high magnification amplifier 24a and the band pass filter 24b, and the high magnification amplifier 24a and the band pass filter 24b send, to the clock device 24c, a signal acquired by removing a set frequency component except the oscillation frequency of pulsed laser such as higher harmonic component from the signal for the detection of the oscillation of the pulsed laser. As a result, an accuracy of sampling clock is improved, and it is possible to perform sampling of a detection signal of fluorescence or the like through AD conversion with high accuracy while the sampling is synchronizing with pulsed laser.

Also, in the laser scanning type observation apparatuses (laser scanning microscope apparatus) of the above described embodiments each of which is provided with the sampling-clock generating means 24 further having such a constitution as shown in FIG. 18, the clock device 24c ($24c_1$) which is provided for the sampling-clock generating means 24 has a jitter-removing function, so that jitter which cannot be removed only by the band pass filter 24b can be removed by the clock device 24c ($24c_1$). As a result, it is possible to acquire a sampling clock with high accuracy.

Besides, a method of multiplying sampling timing using an optical system to 4× speed or the like to detect a detection signal or a method of thinning sampling timing to detect a detection signal is also considered as a method of detecting a detection signal with the laser scanning type observation apparatuses (laser scanning microscope apparatus) of the above described embodiments each of which is provided with the sampling-clock means 24 further having such a constitution as shown in FIG. 18, for example. Accordingly, it is preferred that a clock device configured to be capable of dealing with multiplication of and frequency division of sampling clock is used as the clock device 24c in the laser scanning type observation apparatuses (laser scanning microscope apparatus) according to the above described embodiments each of which is provided with the sampling-clock generating means 24 further having such a constitution as shown in FIG. 18.

Also, in the laser scanning type observation apparatuses (laser scanning microscope apparatus) of the above described embodiments each of which is provided with the sampling-clock generating means 24 further having such a constitution as shown in FIG. 18, it is preferred that the clock device 24c provided for the sampling-clock generating means 24 has a wide output band range width.

In the case where an oscillation frequency of pulsed laser emitted by the pulsed-laser oscillation means 11 is 80 MHz for example, it is preferred that a clock device having an output band range from 1/1000 times to 1000 times (several KHz to several GHz) of the oscillation frequency is used as the clock device 24c.

Also, in the laser scanning type observation apparatuses (laser scanning microscope apparatus) of the above described embodiments each of which is provided with the sampling-clock generating means 24 further having such a constitution as shown in FIG. 18, as shown in FIG. 19B, the clock device 24c which is provided for the sampling-clock generating means 24 is configured to be composed of: the first clock device $24c_1$ having a jitter-removing function; and the second clock device $24c_2$ having a wide output band range width, the first clock device $24c_1$ and the second clock device $24c_2$ being connected to each other in a manner of cascade connection. As a result, it is possible for the laser scanning type observation apparatuses to have high performances and it is possible to lower costs for the laser scanning type observation apparatuses, by widening of the range of a selection of clock devices having a jitter-removing function and by widening of the range of a selection of clock devices having a wide output band range width.

Also, in the laser scanning type observation apparatuses (laser scanning type microscope apparatus) of the above described embodiments each of which is provided with the sampling-clock generating means 24 further having such a constitution as shown in FIG. 18, it is preferred that an oscillation frequency of pulsed laser is 70 MHz to 90 MHz. Also, in the laser scanning type observation apparatuses (laser scanning type microscope apparatus) of the above described embodiments each of which is provided with the sampling-clock generating means 24 further having such a constitution as shown in FIG. 18, for example, it is preferred that a transmission band range of the band pass filter 24b ranges approximately from 10 KHz to a frequency 1.2 times the oscillation frequency.

In addition, in the laser scanning type observation apparatuses (laser scanning microscope apparatus) of the above described embodiments each of which is provided with the sampling-clock generating means 24 further having such a constitution as shown in FIG. 18, as shown in FIG. 19C, the sampling-clock generating means 24 includes: a plurality of pairs of high magnification amplifier $24a_{1\ to\ n}$ and band pass filter $24b_{1\ to\ n}$, the high magnification amplifiers $24a_{1\ to\ n}$ being paired with the band pass filters $24b_{1\ to\ n}$ respectively so that the pairs of high magnification amplifier and band pass filter differ from one another in magnification and in transmission band range so as to be capable of dealing with the noise levels of signals for detection of oscillation of pulsed laser from the pulsed-laser oscillation means (monitor signal or time waveform signal for the detection of the output laser beam), and the pairs of high magnification amplifier and band pass filter being arranged to be in a multi-stage arrangement; and the switch element 24d which switches conductive paths of a signal for detection of oscillation of pulsed laser from the pulsed-laser oscillation means, to one another, so as to transmit the signal for detection of oscillation of pulsed laser through a pair of high magnification amplifier and band pass filter having optimum magnification and optimum transmission band range for the signal for detection of oscillation of pulsed laser, in accordance with the noise level of the signal for detection of oscillation of pulsed laser. As a result, it is possible to acquire a sampling clock from which noises are removed with higher accuracy in accordance with the noise level of a signal for detection of oscillation of pulsed laser, so that it is possible to detect fluorescence or the like with higher accuracy.

And, in the laser scanning type observation apparatuses (laser scanning microscope apparatus) of the above described embodiments each of which is provided with the sampling-clock generating means 24 further having such a constitution as shown in FIG. 18, the synchronous signal generating means 13 includes the high magnification amplifier 24a, the band pass filter 24b, and the clock device 24c which are shown in FIG. 19A. Alternatively, the synchronous signal generating means 13 includes the high magnification amplifier 24a, the band pass filter 24b, and the first clock device $24c_1$ which are shown in FIG. 19B. Alternatively, the synchronous signal generating means 13 includes the pairs of the high magnification amplifier $24a_{1\ to\ n}$ and the band pass $24b_{1\ to\ n}$ and the clock device 24c which are shown in FIG. 19C. And, for example, the synchronous signal generating means 13 detects oscillation of pulsed laser emitted by the pulsed-laser oscillation means 11, through: a trigger output signal which is outputted as an electric signal synchronizing with the oscillation of the pulsed laser from the pulsed-laser oscillation means 11; or an electric signal into which a part of the pulsed laser is photo-electrically converted by the photo detector or the photo multiplier for example. And then, a noise is removed from the signal detected by the synchronous signal generating means 13, by the high magnification amplifier 24a and the band pass filter 24b, and a clock signal synchronizing with the oscillation of the pulsed laser emitted by the pulsed-laser oscillation means 11 is outputted by the clock device 24c.

Besides, in the case where the synchronous signal generating means 13 is configured to include the high magnification amplifier 24a, the band pass filter 24b, and the first clock device $24c_1$ which are shown in FIG. 19B, the delay circuit unit 14 should be configured to include the second clock device $24c_2$.

Besides, characteristic constitutions for the laser scanning microscope which is explained using FIGS. 18 to 20 are not limited to the apparatuses which are premised on the above-described embodiments.

Figure 21:
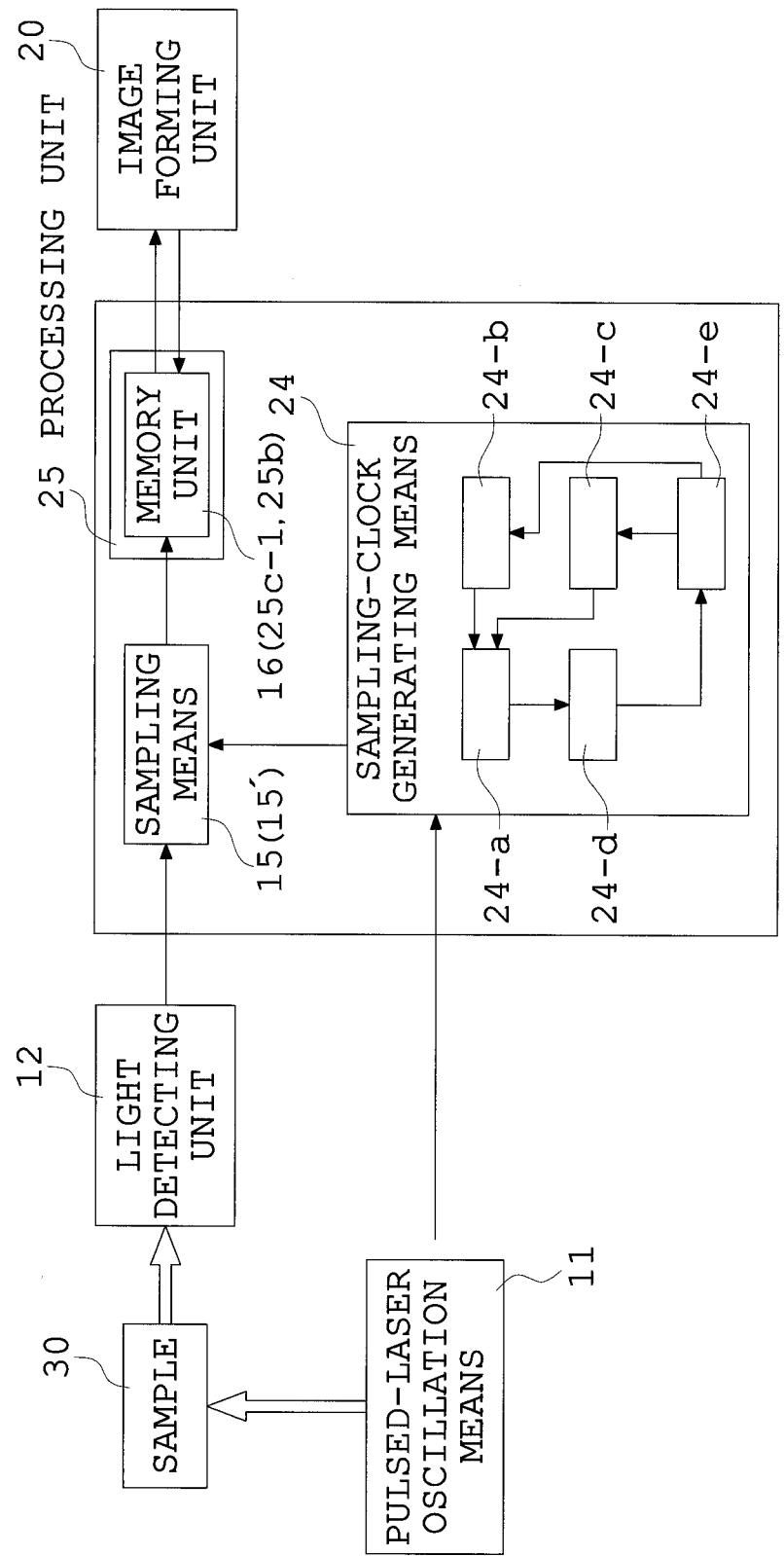
FIG. 21 is a block diagram schematically showing a structure for making it possible to make a clock means with a PPL function continuously track a wide frequency range beyond a frequency range on which the clock means can lock with its PLL function, in the sampling clock generating means provided for the laser scanning type observation apparatus (laser scanning microscope apparatus) according to each of the above-described embodiments.

Also, in the laser scanning type observation apparatuses (laser scanning microscope apparatus) according to the above-described embodiments, as shown in FIG. 21 for example, it is preferred that the sampling-clock generating means 24 further includes: a clock means 24-a having a PLL function, the clock means 24-a converting a signal for detection of oscillation of pulsed laser from the pulsed-laser oscillation means 11, into a clock signal; and a frequency-range setting means 24-b capable of automatically setting a range of frequency tracked by the PLL function and capable of automatically changing a setting of the range of frequency which is given to the clock means 24-a having the PLL function. As a result, the clock means 24-a having the PLL function can be made to continuously track a wide range of frequency beyond a range of frequency which can be tracked with the PLL function.

An oscillation frequency of mode-synchronization ultra-short pulsed laser which is used for a laser scanning microscope varies with temperature change, humidity change, or change of wavelength to be used. In order to adopt the laser scanning microscope apparatus to such variations in oscillation frequency, it is desirable to use a high accurate clock device having a PLL function, such as a PLL frequency synthesizer.

The clock device having a PLL function performs feedback control on the basis of a frequency of a comparison signal set by an operation from the outside so that a difference between an output signal and a standard input signal from the outside in phase is invariable, to generate oscillation of clock signal. As a result, the use of the clock device having a PLL function makes it possible to acquire a sampling clock synchronizing with an oscillation frequency of pulsed laser despite occurrence of variations of the oscillation frequency of the pulsed laser.

However, a range of frequency which the PLL function used in high accurate clock devices such as PLL frequency synthesizer can track is merely a range of a frequency of a comparison signal set by an operation from the outside approximately ±10 ppm, in the case where the clock devices are cheap ones which are generally used.

As a result, when an oscillation frequency of the mode-synchronization ultra-short pulsed laser varies, the oscillation frequency having varied is beyond a range of frequency which a clock device can track, so that the clock device could be inevitably out of its locked state.

In order to put the clock device which is not in its locked state in its locked state, an operation of making a setting of a range of frequency which the PLL function of the clock device can track has to be performed afresh. As a result, acquisition of images has to be stopped as often as the clock device is out of its locked state, so that operation of the laser scanning type observation apparatus inevitably becomes troublesome.

A constitution shown in FIG. 21 is made in the view of such a conventional problem. The objective of the constitution shown in FIG. 21 is to offer a laser scanning microscope apparatus making it possible to acquire a sampling clock synchronizing with an oscillation mode of a laser beam source with a clock device in its locked state and without stopping image acquisition to perform an operation of setting anew a range of frequency which the PLL function of the clock device can track, even if an oscillation frequency of mode-synchronization ultra-short pulsed laser varies to be beyond a range of frequency which the PLL function can track.

Figure 22A:
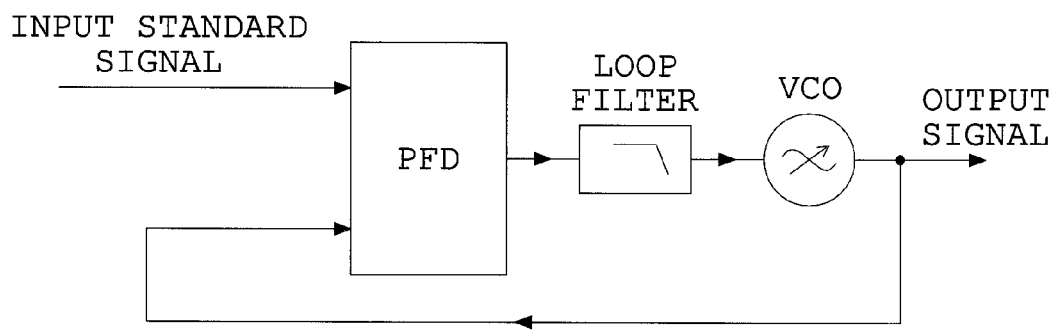
FIGS. 22A and 22B are explanatory views schematically showing a structure of the clock device with the PLL function.
Figure 22B:
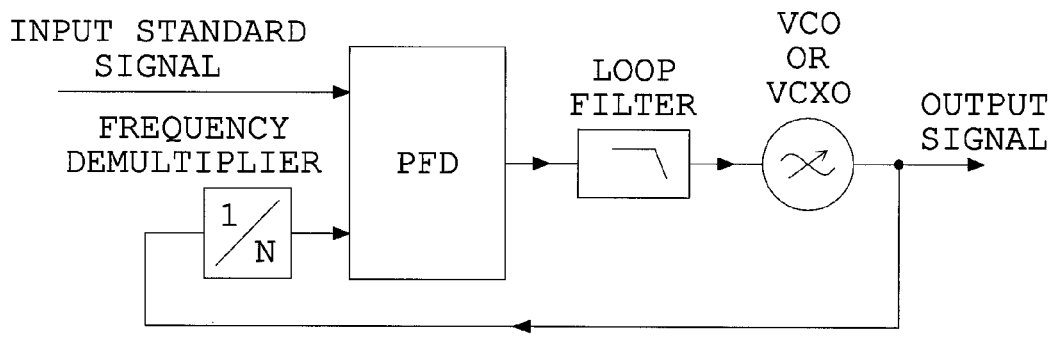
Figure 23:
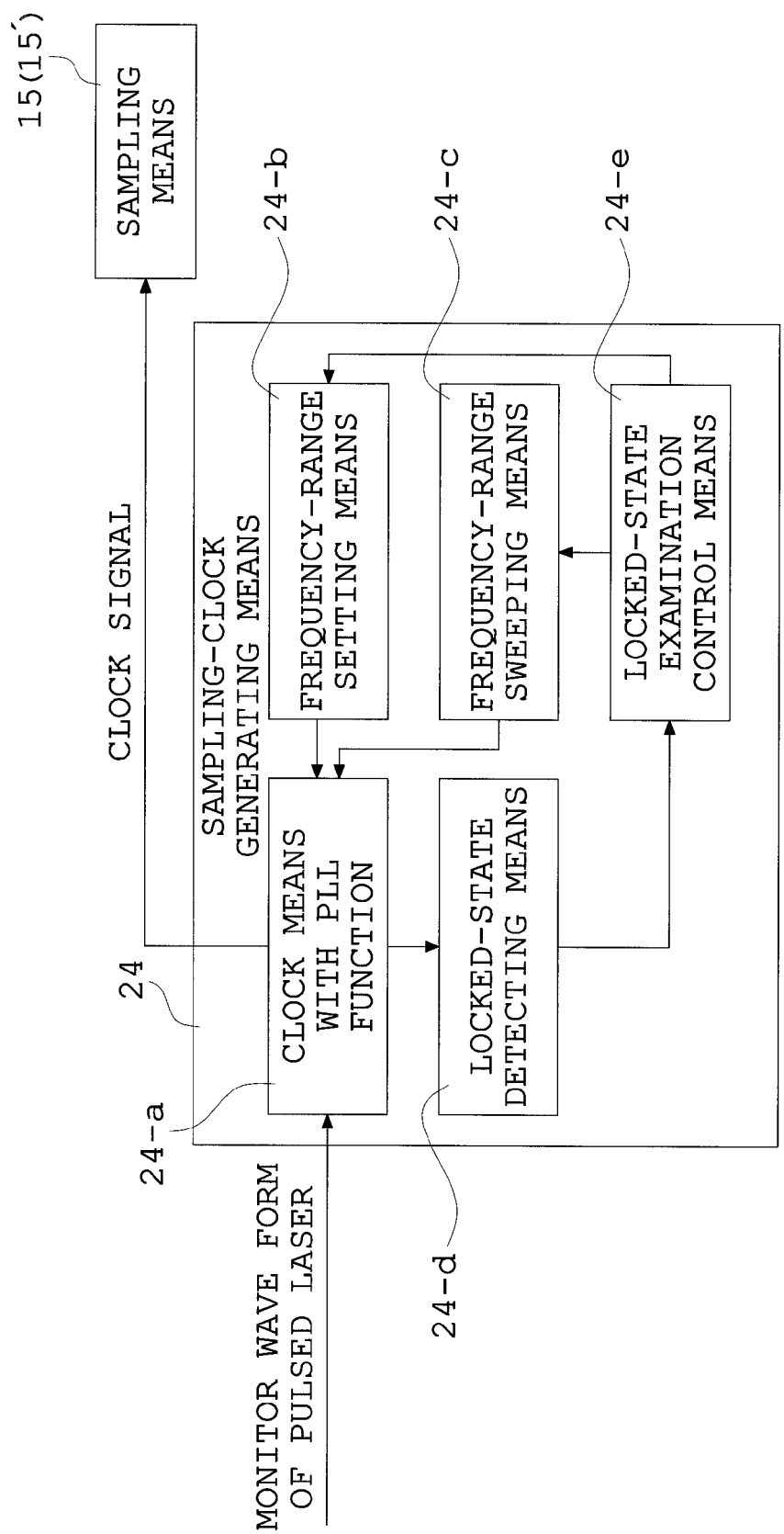
FIG. 23 is a block diagram showing a structure of the sampling-clock generating means of the laser scanning type observation apparatus (laser scanning microscope apparatus) shown in FIG. 21.
Figure 24:
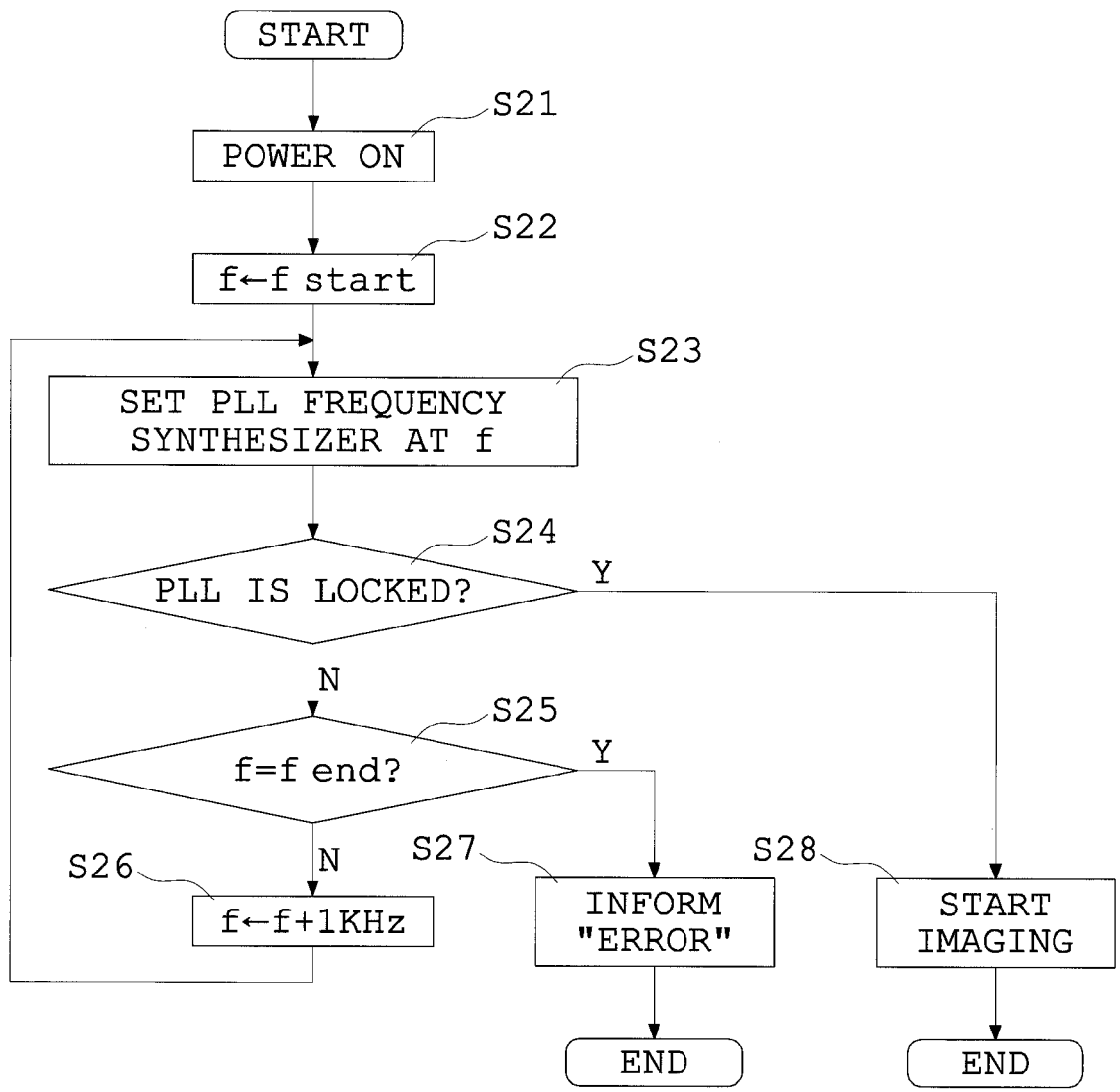
FIG. 24 is a flow chart showing one example of procedures for processes of controlling an examination of a locked state for the sampling clock generating means in the laser scanning type observation apparatus (laser scanning microscope apparatus) shown in FIG. 21.
Figure 25:
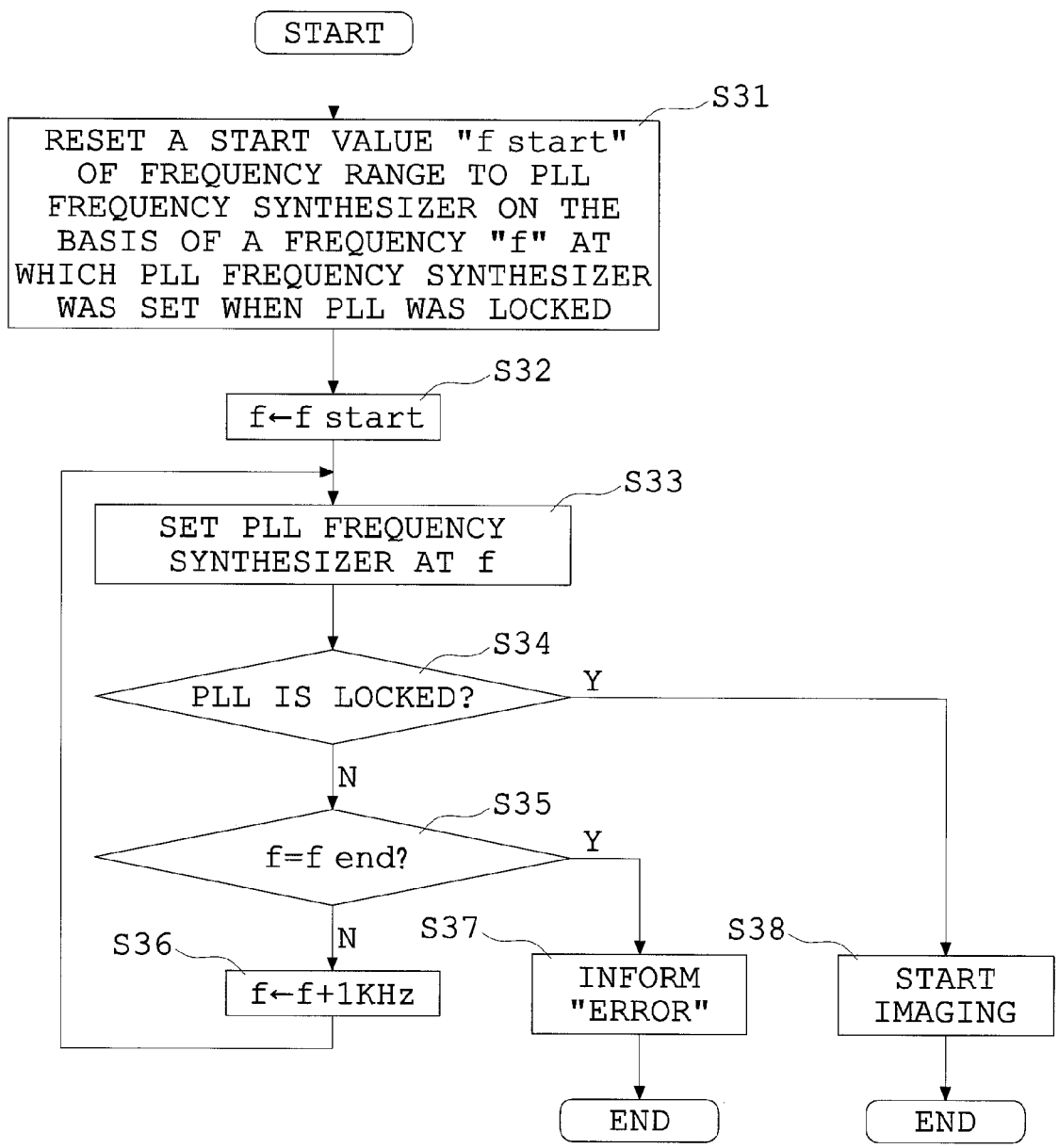
FIG. 25 is a flow chart showing another example of procedures for processes of controlling an examination of a locked state for the sampling clock generating means in the laser scanning type observation apparatus (laser scanning microscope apparatus) shown in FIG. 21.

FIG. 21 is a block diagram schematically showing a structure for making it possible to make a clock means with a PPL function continuously track a wide frequency range beyond a frequency range on which the clock means can lock with its PLL function, in the sampling clock generating means provided for the laser scanning type observation apparatus (laser scanning microscope apparatus) of each of the above-described embodiments. FIGS. 22A and 22B are explanatory views schematically showing a structure of the clock device with the PLL function, FIG. 22A is a block diagram showing a fundamental structure of a PLL oscillator, and FIG. 22B is a block diagram showing a fundamental structure of a PLL frequency synthesizer. FIG. 23 is a block diagram showing a structure of the sampling-clock generating means of the laser scanning type observation apparatus (laser scanning microscope apparatus) shown in FIG. 21. FIG. 24 is a flow chart showing one example of procedures for processes of controlling an examination of a locked state for the sampling clock generating means in the laser scanning type observation apparatus (laser scanning microscope apparatus) shown in FIG. 21. FIG. 25 is a flow chart showing another example of procedures for processes of controlling an examination of a locked state for the sampling clock generating means in the laser scanning type observation apparatus (laser scanning microscope apparatus) shown in FIG. 21.

Now, a clock means having the PLL function is explained using FIG. 22.

The clock means having the PLL function includes a phase frequency detector (PFD), a loop filter, and a voltage controlled oscillator (VCO) (or a voltage controlled crystal oscillator (VCXO)) to be configured as a PLL oscillator (refer to FIG. 22A) or a PLL frequency synthesizer (refer to FIG. 22B).

The phase frequency detector (PFD) compares a phase of a standard signal inputted from the outside with a phase of a comparison signal and then outputs a difference between these phases as a phase difference signal shaped like a pulse. The loop filter is composed of a filter such as a low pass filter (LPF) and cuts off alternating current components in the pulse-shaped phase difference signal outputted by the phase frequency detector (PFD), to output a rectified control voltage. The voltage controlled oscillator (VCO) controls an output frequency on the basis of control voltage outputted by the loop filter.

And, in the clock means having the PLL function, an output signal form the voltage controlled oscillator (VCO) is fed back to the phase frequency detector (PFD) so that a phase difference between: a standard signal inputted from the outside: and the output signal from the voltage controlled oscillator (VCO) is invariable (or in the locked state). Besides, such a PLL frequency synthesizer as shown in FIG. 22B includes a 1/N frequency demultiplier which is placed on a loop circuit on which feedback is performed, in the constitution shown in FIG. 22A. And, the 1/N frequency demultiplier outputs a signal the frequency of which is one over N as large as the frequency of the output signal outputted by the voltage controlled oscillator (VCO), as a comparison signal, so that the frequency of the output signal from the voltage controlled oscillator (VCO) is increased to be N times as large as the frequency of the standard signal inputted from the outside.

Also, in the clock means having the PLL function, a frequency of a comparison signal (a frequency division number N of the frequency demultiplier in the PLL frequency synthesizer shown in FIG. 22B) is set by a manual operation in feedback control relative to the standard signal inputted from the outside.

However, a range of frequency in which conventional clock means with the PPL function can track standard signals inputted from the outside is merely a range of about ±10 ppm of a frequency of comparison signal, the frequency of comparison signal being set by an operation from the outside. In the case where a frequency of comparison signal set by an operation from the outside is fixed at 100 MHz for example, a range of frequency in which the PLL function can track the signals is a range of about ±1 KHz.

Accordingly, in the case where a clock means having the PLL function is used in order to acquire such a sampling clock as synchronizes with an oscillation mode of a mode-synchronization ultra-short pulsed laser used for a laser scanning microscope, if the oscillation frequency of the mode-synchronization ultra-short pulsed laser that is a standard signal inputted from the outside varies, then the oscillation frequency having varied could be beyond the range of frequency capable of being tracked by the clock device (the set frequency ±10 ppm), so that the clock device is inevitably out of its locked state (That is to say, there could occur a state in which a difference between phases of the standard signal inputted from the outside and a signal outputted from the voltage controlled oscillator (VCO) is not invariable).

In order to put the clock device out of the locked state into the locked state, a new range of frequency of comparison signal in which the clock device can track the oscillation frequency of the mode-synchronization ultra-short pulsed laser has to be set anew. However, an operation of a setting of a range of frequency capable of being tracked by the clock device has to be performed manually in the prior art, so that acquisition of images has to be stopped.

As in the laser scanning type observation apparatuses (laser scanning microscope apparatus) according to the above-described embodiments each of which is provided with the sampling-clock generating means 24 further having such a constitution as shown in FIG. 21, the sampling-clock generating means 24 includes: a clock means 24-*a* having a PLL function, the clock means 24-*a* converting a signal for detection of oscillation of pulsed laser from the pulsed-laser oscillation means 11 into a clock signal; and a frequency-range setting means 24-*b* capable of automatically setting a range of frequency tracked by the PLL function and capable of automatically changing a setting of the range of frequency, for the clock means 24-*a* having the PLL function. As a result, even if the oscillation frequency of the pulsed laser widely varies to be beyond a range of frequency capable of being tracked by the PLL function (±10 ppm of the set frequency) and the clock means 24-*a* having the PLL function is out of its locked state, the frequency-range setting means 24-*b* automatically sets a new range of frequency capable of being tracked by the PPL function to change the range of frequency that cannot be tracked by the PLL function to the new range of frequency, so that the clock means 24-*a* with the PLL function can be made to continuously track a wide range of frequency beyond the range of frequency capable of being tracked by the PPL function (±10 ppm of the set frequency). As a result, it is possible to acquire a sampling clock synchronizing with the oscillation mode of the laser beam source with the clock means 24-*a* in its locked state and without performing an operation for setting the range of frequency capable of being tracked by the PLL function of the clock means 24-*a* afresh after stopping acquisition of an image.

Also, in the laser scanning type observation apparatuses (laser scanning microscope apparatus) of the above-described embodiments each of which is provided with the sampling-clock generating means 24 further having such a constitution as shown in FIG. 21, it is preferred that the sampling-clock generating means 24 further includes: a locked-state detecting means 24-*d* which detects the locked state of the clock means 24-*a* with the PPL function; a frequency-range sweeping means 24-*c* which sweeps a set range of frequency in increments of a set frequency to change a range of frequency capable of being tracked by the PLL function to another one, the range of frequency capable of being tracked by the PPL function as a setting being given to the clock means 24-*a* having the PLL function through the frequency-range setting means 24-*b*; and a locked-state examination control means 24-*e* which ends: the sweep performed by the frequency-range sweeping means 24-*c*; and the setting of a new range of frequency to be tracked and the change of a setting of a range of frequency to be tracked that are performed by the frequency-range setting means 24-*b* when the locked-state detecting means 24-*d* detects the locked state of the clock means 24-*a* with the PLL function while the clock means 24-*a* with the PLL function is tracking a tracked range of frequency to which a range of frequency was changed by the frequency-range setting means 24-*b* after the set frequency range is swept by the frequency-range sweeping means 24-*c*.

Such a constitution makes it possible to acquire the locked state of the clock means 24-*a* having the PLL function efficiently, without performing an operation for setting a range of frequency capable of being tracked by the PLL function anew.

Also, in the laser scanning type observation apparatuses (laser scanning microscope apparatus) of the above-described embodiments each of which is provided with the sampling-clock generating means 24 further having such a constitution as shown in FIG. 21, it is preferred that the locked-state examination control means 24-*e* makes the frequency-range setting means 24-*b* automatically make a re-setting of a range of frequency to be tracked by the PLL function which was given to the clock means 24-*a* with the PLL function as a setting, on the basis of a frequency at the time the locked-state detecting means 24-*d* detected the locked state of the clock means 24-*a* having the PLL function, when the locked-state detecting means 24*d* detects the unlocked state of the clock means 24-*a* having the PLL function after having detected the locked state of the clock means 24-*a* having the PLL function.

Such a constitution makes it possible to acquire the locked state of the clock means 24-*a* having the PLL function efficiently, without performing a manual operation for setting a range of frequency capable of being tracked by the PLL function anew, even if the clock means 24-*a* having the PLL function changes from its locked state to its unlocked state.

Also, in the laser scanning type observation apparatuses (laser scanning microscope apparatus) of the above-described embodiments each of which is provided with the sampling-clock generating means 24 further having such a constitution as shown in FIG. 21, it is preferred that the frequency-range setting means 24-*b* can give a setting of frequency to the clock means 24-*a* having the PLL function and can change a setting of frequency, in a range from 70 MHz to 100 MHz.

In addition, in the laser scanning type observation apparatuses (laser scanning microscope apparatus) of the above-described embodiments each of which is provided with the sampling-clock generating means 24 further having such a constitution as shown in FIG. 21, it is preferred that the frequency-range sweeping means 24-*c* sweeps a frequency range of ±10 MHz in increments of 1 KHz.

In such a constitution, even if a range of frequency in which a standard signal inputted from the outside can be tracked by the PLL function of the clock means 24-*a* is merely a range of approximately ±10 ppm of a frequency of a comparison signal set by an operation from the outside, or even if the clock means 24-*a* has a PLL function which can track only a frequency range of about ±1 KHz in the case where the frequency of the comparison signal set by an operation from the outside is 100 MHz for example, an automatic setting of a range of frequency capable of being tracked by the PLL function and an automatic change of a setting of the range of frequency, which are made by the frequency-range setting means 24-*b* at intervals of ±1 KHz in a frequency range of ±10 MHz swept by the frequency-range sweeping means 24-*c*, can make the clock means 24-*a* with the PLL function continuously track a wide range of frequency (10 MHz) beyond the range of frequency capable of being tracked by the PLL function (approximately ±10 ppm of the set frequency, for example ±1 KHz). As a result, it is possible to acquire a sampling clock synchronizing with the oscillation mode of the laser beam source with the clock means 24-*a* in its locked state, without performing an operation for setting a range of frequency capable of being tracked by the PLL function of the clock means 24-*a* anew after stopping an image acquisition.

And, in the laser scanning type observation apparatuses (laser scanning microscope apparatus) of the above-described embodiments each of which is provided with the sampling-clock generating means 24 further having such a constitution as shown in FIG. 21, it is preferred that the sampling-clock generating means 24 includes the clock means 24-*a* having the PPL function, the frequency-range setting means 24-*b*, the frequency-range sweeping means 24-*c*, the locked-state detecting means 24-*d*, and the locked-state examination control means 24-*e*, as shown in FIG. 23 for example.

The clock means 24-*a* with the PLL function is composed of a PLL oscillator as shown in FIG. 22A or a PLL frequency synthesizer as shown in FIG. 22B, for example. And, the clock means 24-*a* performs a feedback control to keep a difference between phases of a standard signal inputted from the outside and a comparison signal invariable (to put the clock means 24-*a* in its locked state) and converts the standard signal into a clock signal, the standard signal inputted from the outside being a signal for detection of oscillation of pulsed laser from the pulsed-laser oscillation means 11, and the comparison signal being a signal outputted by the voltage controlled oscillator (VCO) for example. Also, the clock means 24-*a* with the PLL function is configured to be capable of adjusting a frequency of a comparison signal through an external control device (like CPU or FPGA (Field-Programmable Gate Array)).

The frequency-range setting means 24-*b* is provided for the external control device (such as CPU or FPGA) and is configured: to be capable of automatically setting a range of frequency capable of being tracked by the PLL function for the clock means 24-*a* having the PLL function (for example, the range being a range of about ±10 ppm of a frequency of a signal outputted by the voltage controlled oscillator (VCO) shown in FIG. 22A or of a frequency set as a frequency division number of a frequency demultiplier shown in FIG. 22B); and to be capable of automatically changing a range of frequency that is capable of being tracked by the PLL function.

The frequency-range sweeping means 24-*c* is provided for the external control device (CPU, FPGA, or the like) and is configured to be capable of sweeping a set range of frequency (for example, a range of ±10 MHz) in increments of a set frequency (for example, in increments of 1 KHz) to make the frequency-range setting means 24-*b* change a range of frequency capable of being tracked by the PLL function which was given to the clock means 24-*a* with the PLL function as a setting.

The locked-state detecting means 24-*d* is provided for the clock means 24-*a* having the PLL function and is configured to detect the locked state of the clock means 24-*a* with the PLL function. Besides, FIGS. 21 and 23 show the locked-state detecting means 24-*d* and the clock means 24-*a* having the PLL function in such a way that the locked-state detecting means 24-*d* is separated from the clock means 24-*a*, for the sake of convenience.

The locked-state examination control means 24-*e* is provided for the external control device (CPU, FPGA, or the like). And, the locked-state examination control means 24-*e* is configured to end: sweeping of a set frequency range performed by the frequency-range sweeping means 24-*c*; and a setting of a range of frequency capable of being tracked by the PLL function and a change of the range of frequency that are made by the frequency-range setting means 24-*b*, when the locked-state detecting means 24-*d* detects the locked state of the clock means 24-*a* having the PLL function while the clock means 24-*a* having the PLL function is tracking a range of frequency tracked by the PLL function which is changed by the frequency-range setting means 24-*b* through the sweeping of the set frequency range by the frequency-range sweeping means 24-*c*.

Also, the locked-state examination control means 24-*e* is also configured to make the frequency-range setting means 24-*b* automatically reset a range of frequency to be tracked by the PLL function which was is given to the clock means 24-*a* having the PLL function as a setting, on the basis of a frequency at the time the locked-state detecting means 24-*d* detected the locked state of the clock means 24-*a* having the PLL function, when the locked-state detecting means 24-*d* detects the unlocked state of the clock means 24-*a* having the PLL function after having detected the locked state of the clock means 24-*a* having the PLL function.

A procedure for performing a locked-state examination control process in the sampling-clock generating means 24 is explained with FIGS. 24 and 25, the procedure for performing a locked-state examination control process in the sample-clock generating means 24 being performed in the laser scanning type observation apparatuses (laser scanning microscope apparatus) of the above described embodiments each of which is provided with the sampling-clock generating means 24 further having such a constitution as shown in FIG. 21 when a signal for detection of oscillation of pulsed laser from the pulsed-laser oscillation means 11 (monitor signal, time waveform signal for a detection of output laser beam, or the like) is reshaped to be outputted as a sampling clock.

The locked-state examination control means 24-*e* finds a frequency at which the clock means 24-*a* with the PLL function is in a locked state, in turning on the switch, at the start of the use of the laser scanning type observation apparatus, in changing a wavelength of pulsed laser, or in setting of frequency or a change of a setting of frequency by a user, while the locked-state examination control means 24-*e* is making the frequency-range sweeping means 24-*c* sweep a set range of frequency in increments of a set frequency and is making the frequency-range setting means 24-*b*: make a setting of frequency range capable of being tracked by the PLL function; and change a setting of a frequency range capable of being tracked by the PLL function which was given to the clock means 24-*a* with the PLL function as a setting.

In this explanation, a procedure for performing a locked-state examination control process until the clock means 24-*a* with the PLL function is in the locked state after turning on switch is explained using FIG. 24.

After power is supplied to the sampling-clock generating means 24 (Step S21), the frequency-range setting means 24-*b* is given an initial setting of a start value $f_{start}$ of a range of frequency to be tracked by the PLL function (in this explanation, the start value $f_{start}$ is ±10 MHz), through an external operation means which is not shown in the drawings. After making the setting of the start value $f_{start}$ of the range of frequency, a range of frequency which the frequency-range sweeping means 24-*c* sweeps (and which has a range width of +10 MHz in this explanation) is added to the start value $f_{start}$ of the range of frequency having been set, so that an end value $f_{end}$ for the range of frequency to be given to the clock means 24-*a* with the PLL function as a setting value through the frequency-range setting means 24-*b* is determined (the end value $f_{end}$ is 70 MHz±10 MHz in this explanation). The frequency-range setting means 24-*b* uses the start value $f_{start}$ of frequency which is initially set, as a frequency f to be given to the clock means 24-*a* with the PLL function as a setting (Step S22). And, the frequency-range setting means 24-*b* sets the clock means 24-*a* with the PLL function at the frequency f (Step S23).

The clock means 24-*a* having the PLL function performs feedback control while tracking the range of frequency of about ±10 ppm of the set frequency (a range of ±1 kHz in this explanation), to aim at a state in which a phase difference between: a detection signal for detection of oscillation of pulsed laser which is an inputted standard signal; and a comparison signal is invariable (locked state).

The locked-state detecting means 24-*d* detects whether the clock means 24-*a* with the PLL function is in its locked state or not, while the clock means 24-*a* with the PLL function is tracking the range of frequency (Step S24).

When the locked-state detecting means 24-*d* detects that the clock means 24-*a* with the PLL function is in its locked state, the locked-state examination control means 24-*e* makes is the frequency-range sweeping means 24-*c* stop the sweeping of the frequency range and makes the frequency-range setting means 24-*b*: stop making a setting of a frequency range: and stop changing a setting of frequency range. And, the light detecting unit 12 starts to acquire an image (Step S28).

When the locked-state detecting means 24-*d* detects that the clock means 24-*a* with the PLL function is not in its locked state, the locked-state examination control means 24-*e* checks whether the frequency f given to the clock means 24-*a* having the PLL function as a setting reaches the end value $f_{end}$ for the range of frequency (which is 70 MHz±10 MHz in this explanation) or not (Step S25).

When: the locked-state detecting means 24-*d* detects that the clock means 24-*a* with the PLL function is not in its locked state; and the frequency f given to the clock means 24-*a* with the PLL function as a setting value reaches the end value $f_{end}$ for the range of frequency (which is 70 MHz±10 MHz in this explanation), an error informing means which is not shown in the drawings informs an error message (Step S27).

When: the locked-state detecting means 24-*d* detects that the clock means 24-*a* with the PLL function is not in its locked state; and the frequency f given to the clock means 24-*a* with the PLL function as a setting value does not reach the end value $f_{end}$ for the range of frequency (which is 70 MHz±10 MHz in this explanation), the frequency-range sweeping means 24-*c* performs a frequency sweep to change the frequency f to a frequency (f+1 KHz) acquired by adding 1 KHz to the frequency f, the frequency f having given to the clock means 24-*a* with the PLL function as a setting, and then the frequency-range setting means 24-*b* sets the clock means 24-*a* with the PLL function at the frequency (f+1 KHz) as a new frequency f to be given to the clock means 24-*a* with the PLL function as a setting anew (Step S26). Afterward, the examination control processes of the Steps S23 to S26 are repeated: until the locked-state detecting means 24-*d* detects that the clock means 24-*a* with the PLL function is in its locked state; or until the locked-state detecting means 24-*d* detects that the clock means 24-*a* with the PLL function is not its locked state while the frequency f having given to the clock means 24-*a* with the PLL function as a setting reaches the end value $f_{end}$ for the range of frequency (which is 70 MHz±10 MHz in this explanation).

Next, a procedure for processing examination control until the clock means 24-*a* with PLL function gets its locked state again after changing from its locked state into its unlocked state is explained using FIG. 25.

The locked-state examination control means 24-*e* makes the frequency-range setting means 24-*b* give the clock means 24-*a* with the PLL function a setting of a start value $f_{start}$ of a range of frequency tracked by the PLL function anew, on the basis of the frequency f having been detected by the locked-state detecting means 24-*d* at the time the clock means 24-*a* with the PLL function was in its locked state (Step S31). In this explanation, for the sake of convenience, it is presumed that, when the frequency f was 80 MHz, the locked-state detecting means 24-*d* detected that the clock means 24-*a* with the PLL function was in its locked state. When the start value $f_{start}$ of a frequency to be set is set anew, the range of frequency (±10 MHz in this explanation) in which the frequency-range sweeping means 24-*c* sweeps frequency is added to the start value $f_{start}$ of the frequency range having been set anew, so that an end value $f_{end}$ for the range of frequency (80 MHz±10 MHz, in this explanation) to be given to the clock means 24-*a* with the PLL function as a setting by the frequency-range setting means 24-*b* is determined.

The frequency-range setting means 24-*b* sets the clock means 24-*a* with the PLL function at the start value $f_{start}$ of the range of frequency having been set anew, as the frequency f to be given to the clock means 24-*a* with the PLL function as a setting (Step S12). Afterward, approximately the same examination control process as the process of the Steps S23 to S28 shown in FIG. 24 is performed (Steps S33 to S38).

Besides, in the case where the laser scanning type observation apparatuses (laser scanning microscope apparatus) according to the above-described embodiments each of which is provided with the sampling-clock generating means 24 further having such a constitution as shown in FIG. 21 are configured: to include an ON-OFF switching unit so as to thin sampling timing to perform detection, the ON-OFF switching unit switching irradiation of pulsed laser emitted by the pulsed-laser oscillation means 11 to a test object and non-irradiation of pulsed laser emitted by the pulsed-laser oscillation means 11 to the test object, to each other; or to include a delay optical path unit splitting an optical path of pulsed laser emitted by the pulsed-laser oscillation means 11 into at least two or more optical paths and multiplying a frequency of the pulsed laser emitted by the pulsed-laser oscillation means 11 by differences between the lengths of the different optical paths to irradiate a pulsed laser with the multiplied frequency to the test object 30 so as to multiply sampling timing, it is preferred that a clock means configured to be capable of dealing with both a multiplication of and a frequency division of sampling clock is used as the clock means 24-*a* with the PLL function for each of the laser scanning type observation apparatuses (leaser scanning microscope apparatus).

Besides, the characteristic constitutions of the laser scanning microscope explained using FIGS. 21 to 25 are not limited to the apparatuses which are premised on the above-described embodiments.

Figure 26:
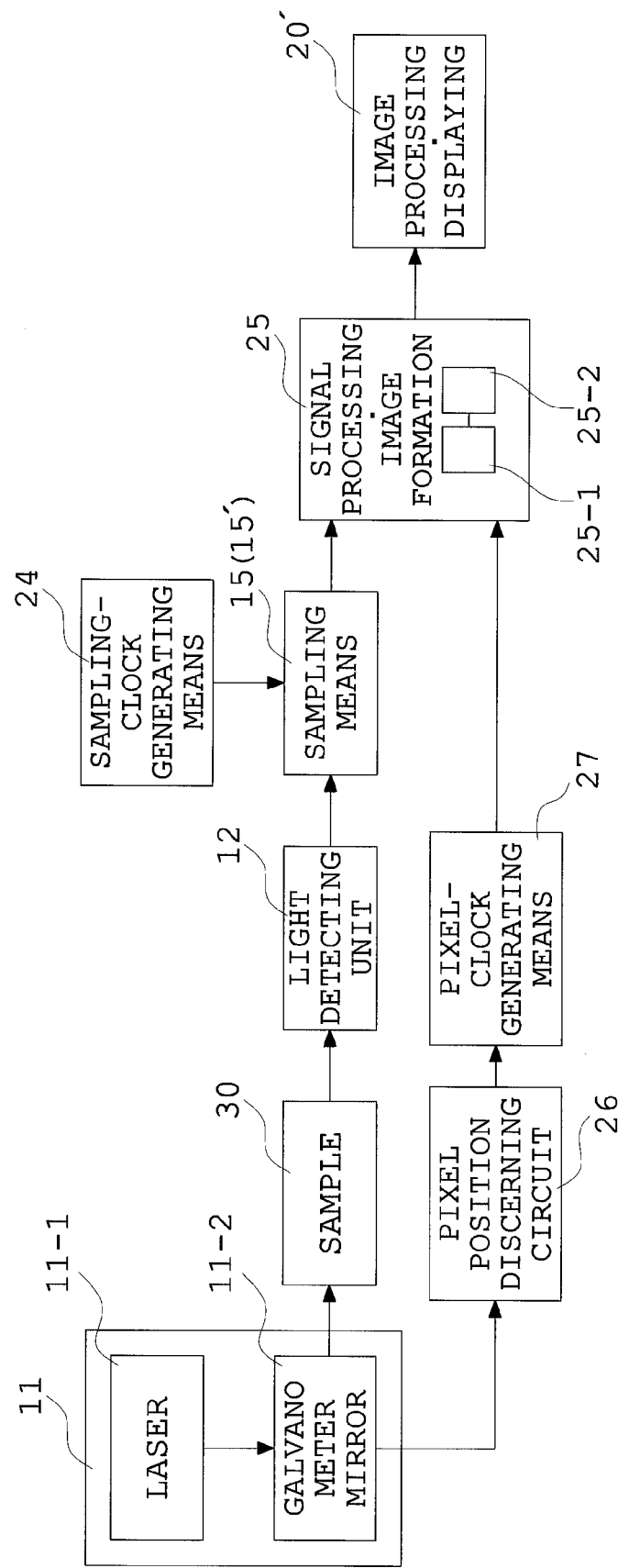
FIG. 26 is a block diagram schematically showing a structure for making it possible to remove difference between pixels in brightness to improve image qualities without complicated operations even though laser-emitting time varies with pixels, in the laser scanning type observation apparatus (laser scanning microscope apparatus) of each of the above-described embodiments.

Also, it is preferred that the laser scanning type observation apparatus (laser scanning microscope apparatus) according to each of the above-described embodiments is configured, as shown in FIG. 26 for example, to have a structure in which: the pulsed-laser oscillation means 11 includes a laser beam source 11-1 generating laser oscillation to irradiate pulsed laser to the test object 30 and a scanning means 11-2 capable of scanning an irradiation point on the test object through resonance phenomenon, the irradiation point on the test object being caused by a laser beam from the laser beam source 11-1; the laser scanning type observation apparatus according to each of the above-described embodiments further includes a pixel-clock generating means 27 which discerns a change in pixel position corresponding to the irradiation point while discerning the change in pixel position corresponding to the irradiation point is synchronizing with the change in irradiation point scanned by the scanning means 11-2 and which outputs a trigger for timing at which a pixel position is changed to another pixel position, as a pixel clock; the sampling-clock generating means 24 outputs sampling clocks many times until the pixel-clock generating means 27 outputs the (n+1)-th pixel clock after outputting the n-th pixel clock; the processing means 25 includes a cumulative addition block 25-1 and a division block 25-2; the cumulative addition block 25-1 cumulatively adds digital data generated by the sampling means 15 (15') performing a plurality of A/D conversions together between a point in time to input the n-th pixel clock outputted by the pixel-clock generating means 27 and a point in time to input the (n+1)-th pixel clock outputted by the pixel-clock generating means 27 while the cumulative addition block 25-1 is counting the number of additions in the cumulative addition, the cumulative addition block 25-1 sends the total sun of the digital data cumulatively added together and the number of additions in the cumulative addition to the division block 25-2 while sending the total sum of the digital data cumulatively added together and the number of additions in the cumulative addition to the division block 25-2 is synchronizing with timing of the input of the (n+1)-th pixel clock, the total sum being acquired by cumulatively adding the digital data together until the (n+1)-th pixel clock is inputted and the number of additions in the cumulative addition being counted until the (n+1)-th pixel clock is inputted, and then the cumulative addition block 25-1 resets its areas for cumulatively adding the digital data together and for counting the number of additions in the cumulative addition into the initial states of the areas respectively; and the division block 25-2 is configured to divide the number of additions in the cumulative addition into the total sum of the digital data cumulatively added together, the total sum of the digital data cumulatively added together being sent by the cumulative addition block 25-1. As a result, it is possible to remove differences between the pixels in brightness to improve image quality without complicated operations in the laser scanning type observation apparatuses according to the above-described embodiments having such a constitution, even if a time period for which laser is irradiated varies with the pixels.

In a laser scanning microscope in general, an irradiation point to which a laser beam is irradiated is scanned by changing an angle of a scanning means such as a galvanometer mirror.

Also, in imaging the test object, a laser beam is irradiated to an area corresponding to one pixel for a given time period and then returning light (reflected light, scattering light, or fluorescence) is detected, so that a pixel value at the position of the pixel is determined.

Conventional methods of determining pixel values in laser scanning type observation apparatuses in the prior art include a method in which a detection signal is integrated through an electric circuit in order to convert a feeble signal from a light detector into a pixel value with a good S/N ratio in fluorescence detection, as performed in a laser microscope disclosed in Japanese patent publication of registration No. 4407423 for example. And, integration of a detection signal and reset operation are repeatedly performed every pixel clock (constituting a trigger for timing at which pixel positions corresponding irradiation points respectively change to one another) in an integration circuit.

Now, in the case where it is desired that a speed of operation of the galvanometer mirror is increased in imaging through a scanning method so that images are acquired with high speed, it is possible to acquire images with higher speed by a scanning method with a resonance phenomenon rather than by a scanning method in which the galvanometer mirror is operated at a fixed speed.

However, in the scanning method with resonance phenomenon, there is a following problem: A scanning speed is not invariable but shows a sine function, so that exposure time, the number of samplings of detection signal, and time for integration vary with pixels. As a result, if data acquired by adding together data which are detected by exposing a test object by the scanning method with resonance phenomenon is used as it is and as a pixel value in imaging the test object, an image at a pixel position corresponding to an irradiation point at which a scanning speed is high becomes dark and the image at a pixel position corresponding to an irradiation point at which a scanning speed is low becomes bright, so that there occurs variations in brightness of the image of the test object.

Methods of removing differences between the pixels in brightness due to differences between the scanning speeds also include a method in which: an integration process for a detection signal is performed with respect to pixels exposed long time for the same period as an integration process for the detection signal is performed with respect to pixels exposed short time; and a part of the detection signal in each of the pixels exposed long time which is not in the integration process period is not used. However, in such a manner, the part of the detection signal that is not used is in vain and the number of integration processes decreases. On the other hand, because a detection signal contains a feeble noise, the noise contained in the detection signal can be averaged if the number of integration processes is increased. As a result, it becomes easy to remove the noises in the detection signal with high accuracy. However, the small number of integration processes easily causes bias of the noise contained in the detection signal, so that it is difficult to remove the noise in the detection signal with high accuracy. As a result, the use of the above-described method in which a part of a detection signal in pixels exposed longer time as compared with pixels exposed short time is not used inevitably deprives laser scanning type observation apparatuses of a chance to remove the noises in the detection signal in the pixels exposed long time with high accuracy.

Also, even in the method in which a test object is imaged with scanning at fixed speed, there is a following problem: a setting of integrated quantities of data detected by exposure (the number of samplings and the number of integration processes for detection signals) has to be changed to another setting as often as a setting of scanning speed is changed to another one, so that operation of such a laser scanning type observation apparatus becomes troublesome.

The configuration shown in FIG. 26 is made in the view of such a conventional problem. The objective of the configuration shown in FIG. 26 is to offer a laser scanning type observation apparatus capable of removing differences between pixels in brightness to improve image quality without complicated operation even in the case where time periods for which pulsed laser is irradiated vary with pixels.

Figure 27:
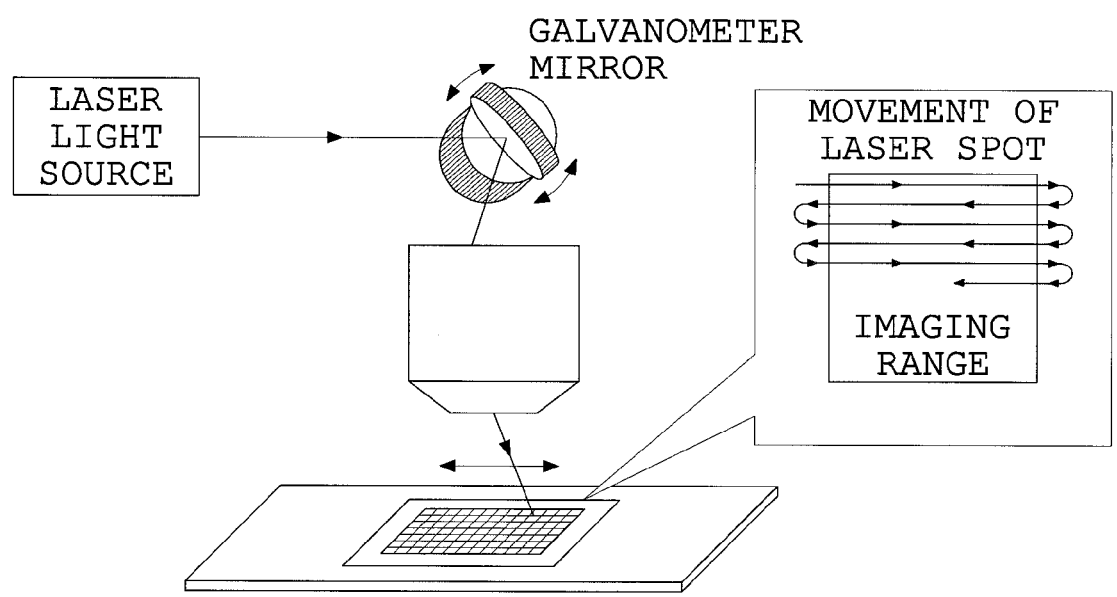
FIG. 27 is an explanatory view conceptually showing a state in which a laser-irradiation point on a test object is scanned through a scanning means using resonance phenomena in the laser scanning microscope apparatus.
Figure 28A:
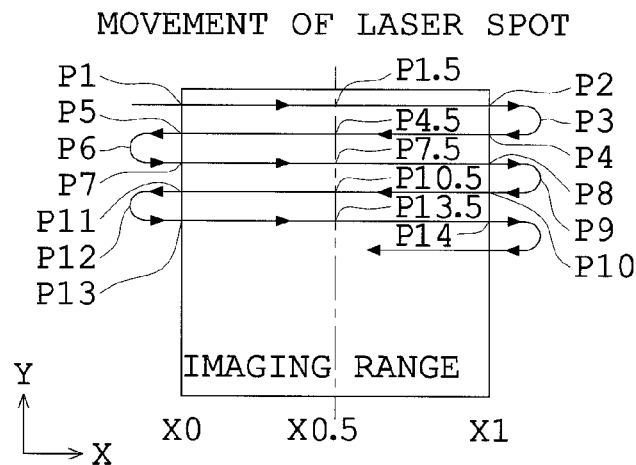
FIGS. 28A to 28D are explanatory views showing a scanning speed at a scanning position of the laser-irradiation point and the number of data on detection signal sampled to be added to one another, in the laser scanning microscope apparatus shown in FIG. 27.
Figure 28B:
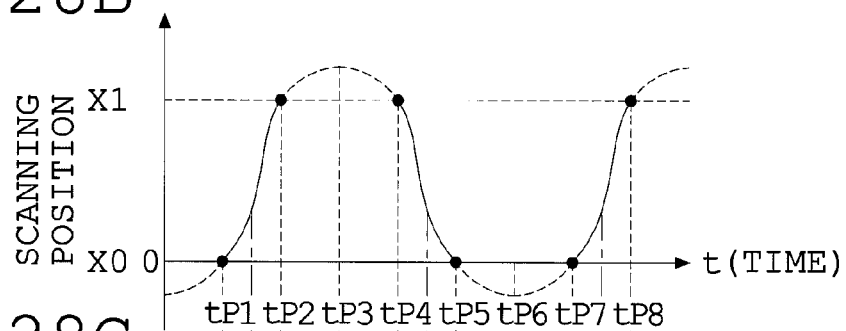
Figure 28C:
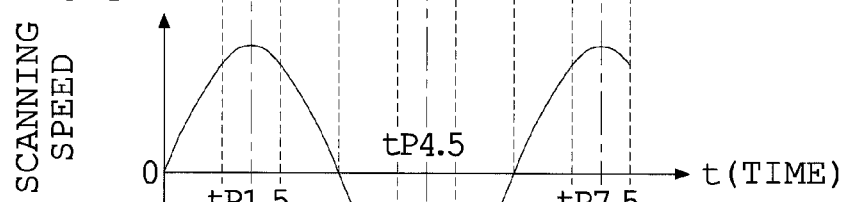
Figure 28D:
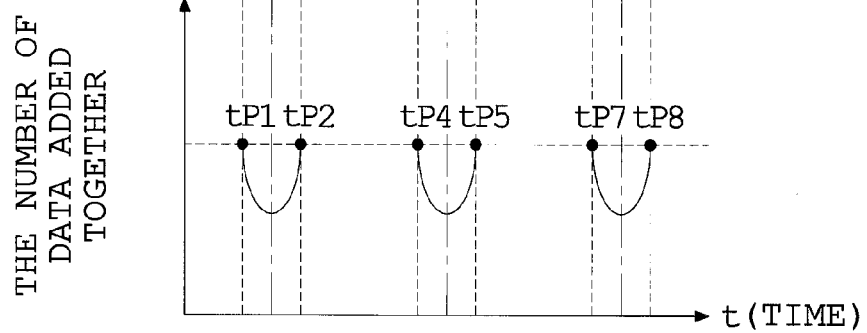
Figure 29:
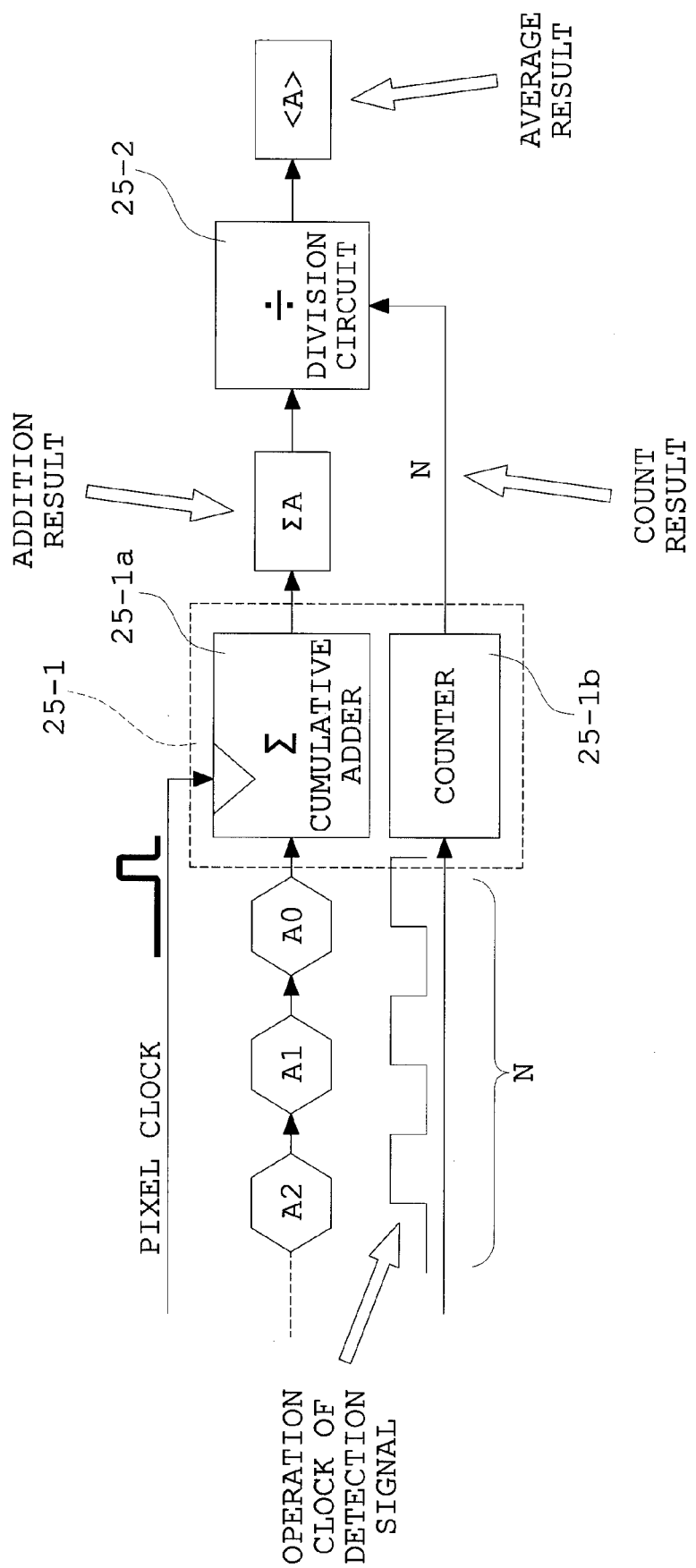
FIG. 29 is an explanatory view showing a structure of a main part of the laser scanning type observation apparatus (laser scanning microscope apparatus) shown in FIG. 26.

FIG. 26 is a block diagram schematically showing a structure for making it possible to remove a difference between pixels in brightness to improve image qualities without requiring complicated operations even though laser-emitting time varies with pixels, in the laser scanning type observation apparatus (laser scanning microscope apparatus) of each of the above-described embodiments. FIG. 27 is an explanatory view conceptually showing a state in which a laser-irradiation point on a test object is scanned through a scanning means using resonance phenomena in the laser scanning microscope apparatus. FIGS. 28A to 28D are explanatory views showing a scanning speed at a scanning position of the laser-irradiation point and the number of data on detection signal sampled to be added to one another, in the laser scanning microscope apparatus shown in FIG. 27, FIG. 28A is a view conceptually showing a movement of the laser-irradiation point, FIG. 28B is a graph showing the movement of the laser-irradiation point shown in FIG. 28A with the relation between scanning position and time, FIG. 28C is a graph showing the movement of the laser-irradiation point shown in FIG. 28A with the relation between scanning speed and time, and FIG. 28D is a graph showing the relation between: the number of data on detection signal sampled to be added to one another; and time corresponding to a set scanning point within an imaging range. FIG. 29 is an explanatory view showing a structure of a main part of the laser scanning type observation apparatus (laser scanning microscope apparatus) shown in FIG. 26.

Figure 32:
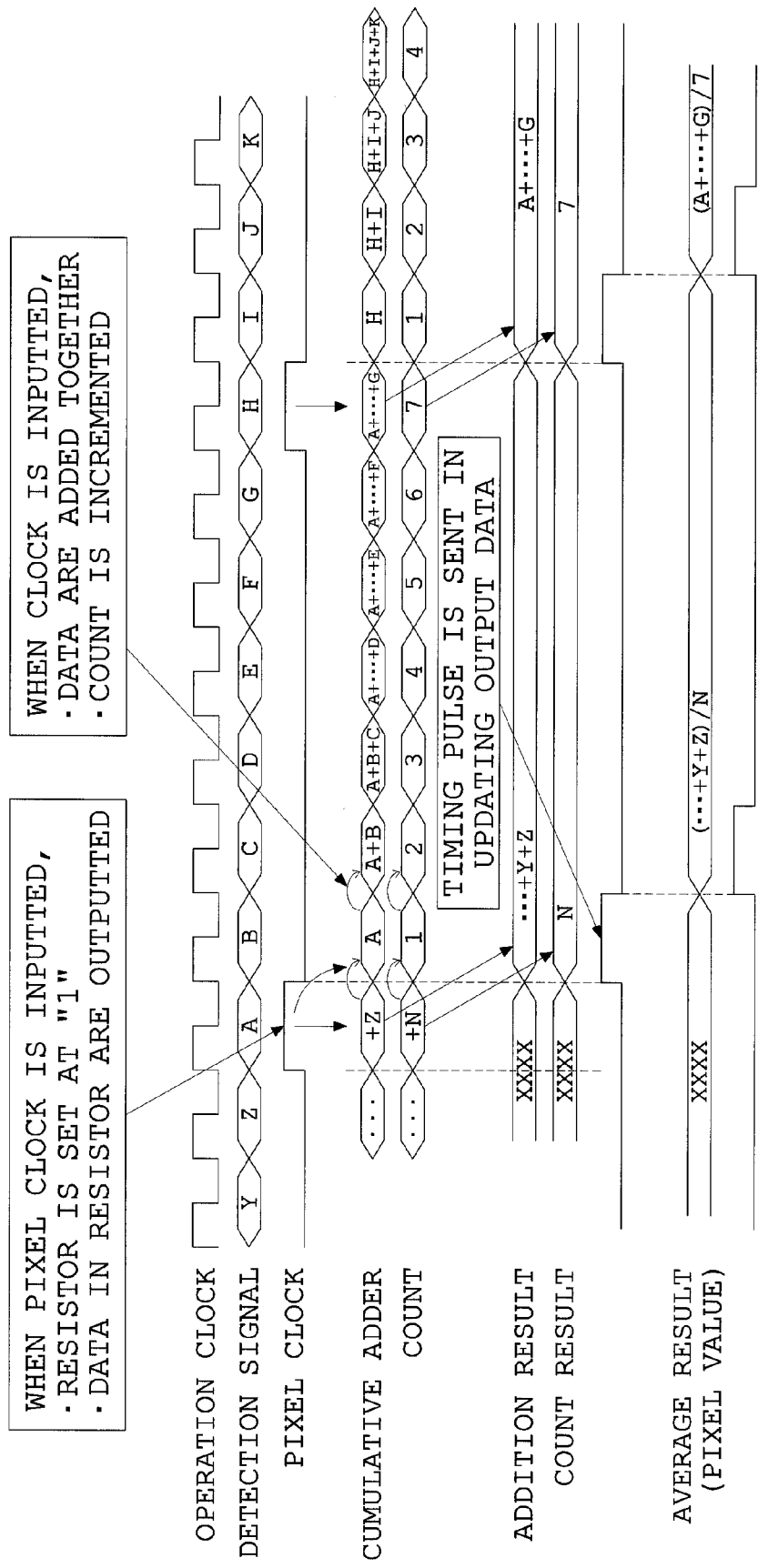
FIG. 32 is a timing chart showing sampling clock, sampled detection signal, pixel clock, data on the detection signal to be cumulatively added to one another, counts of a cumulative addition, data on the total sum of the data on the detection signal to be cumulatively added to one another, the number of the counts of the cumulative addition, and the average of detection signal per pixel, the average of detection signal per pixel being acquired by dividing the data on the total sum of the data on the detection signal to be cumulatively added to one another by the number of the counts of the cumulative addition in each pixel, in the laser scanning type observation apparatuses (laser scanning microscope apparatus) in the above-described embodiments each of which is further provided with a structure as shown in FIG. 26.

FIG. 30 is an explanatory view showing an example of expressions of the reciprocals of 2 to 16 with a formula of addition of negative powers of two. FIGS. 31A and 31B are explanatory views showing an example of a structure of a divider shown in FIG. 29, FIG. 31A is an explanatory view showing a register in which a binary result from a division by a power of two in binary notation is acquired by shifting a binary digit to the right by one bit, and FIG. 31B is an explanatory view showing an example of addition in a combination of registers shown in FIG. 31A in accordance with divisors. FIG. 32 is a timing chart showing sampling clock, sampled detection signal, pixel clock, data on the detection signal to be cumulatively added to one another, counts of additions in the cumulative addition, data on the total sum of the data on the detection signal to be cumulatively added to one another, the number of the counts of additions in the cumulative addition, and the average of detection signal per pixel which is acquired by dividing the data on the total sum of the data on the detection signal to be cumulatively added to one another by the number of the counts of additions in the cumulative addition in each pixel, in the laser scanning type observation apparatuses (laser scanning microscope apparatus) of the above-described embodiments each of which is further provided with a structure as shown in FIG. 26.

In a laser scanning microscope apparatus, as shown in FIG. 27, an irradiation point (laser spot) to which pulsed laser emitted by a laser beam source is irradiated is scanned by changing an angle of an scanning means such as a galvanometer mirror. In imaging a test object, pulsed laser is irradiated to an area corresponding to one pixel for a fixed time period and then returning light (reflective light, scattering light, or fluorescence) is detected, so that a pixel value at a position of the one pixel is determined.

A detected signal is integrated in order to convert the feeble signal from a light detector into a pixel value with a good S/N ratio.

However, in the case where scanning is performed by the scanning means with resonance phenomenon, its scanning speed is not invariable and forms a sine function. For example, in the case where irradiation points are scanned in such a way that the scanning means is made to reciprocate in the X-direction as shown in FIG. 28A, a scanning position reciprocates between an irradiation point X0 and an irradiation point X1 as time t passes by, as shown in FIG. 28B. In this case, the closer the scanning position moves from a boundary point P1 of an imaging range in the X-direction to a middle point P1.5, the higher a scanning speed at which the scanning position moves from the boundary point P1 to a boundary point P2 of the imaging range in the X-direction becomes, as shown in FIG. 28C. And then, the scanning speed becomes the maximum one at the middle point P1.5. Afterward, the closer the scanning position moves from a middle point P1.5 to the boundary point P2, the lower the scanning speed becomes, and the scanning speed becomes approximately zero at a turn point P3. A scanning speed at which the scanning position moves from a boundary point P4 to a boundary point P5, a scanning speed at which the scanning position moves from a boundary point P7 to a boundary point P8, and a scanning speed at which the scanning position moves from a boundary point P10 to a boundary point P11 also vary in the same manner as the scanning speed at which the scanning position moves from the boundary point P1 to the boundary point P2 does.

As described above, the scanning speed of the irradiation point moving in the imaging range varies with pixel positions. On the other hand, sampling of a detection signal is performed at a fixed timing. As a result, the pixels inevitably differ from one another in exposure time, in the number of samplings of the detection signal, and in integration time.

For example, as shown in FIG. 28C, when detected data are imaged as pixel values and as they are, by exposing a test object with irradiation points scanned by a scanning means the scanning speed of which varies with pixel positions, the higher the scanning speed becomes, the more the number of detected data added together at the pixel position decreases, and the lower the scanning speed becomes, the more the number of detected data added together at the pixel position increases, as shown in FIG. 28D. And, in the example shown in FIG. 28, the number of data on the detection signal added together in the imaging range has the maximum value at the boundary points P1, P2, P4, P5, P7, P8, . . . and has the minimum value at the middle points P1.5, P4.5, P7.5, and P10.5.

As a result, if the data on the detection signal to be added together are used as they are and image acquisition is performed, an image at a pixel position corresponding to an irradiation point with a high scanning speed becomes dark, and the image at a pixel position corresponding to an irradiation point with a low scanning speed becomes bright, so that differences in brightness inevitably occur in the image of the test object.

As in the laser scanning type observation apparatus (laser scanning microscope apparatus) according to each of the above-described embodiments further having such a constitution as shown in FIG. 26, the cumulative addition block 25-1 cumulatively adds together digital data which are acquired by a plurality of AD conversion processes performed by the sampling clock means 15 (15'), between: the time the n-th pixel clock outputted by the pixel-clock generating means 27 is inputted; and the time the (n+1)-th pixel clock outputted by the pixel-clock generating means 27 is inputted, the cumulative addition block 25-1 counts the number of additions in the cumulative addition simultaneously with the cumulative addition, the cumulative addition block 25-1 sends to the division block 25-2 the total sum of the digital data cumulatively added together until the (n+1)-th pixel clock is inputted and the number of additions in the cumulative addition counted until the (n+1)-th pixel clock is inputted, while the timing at which the cumulative addition block 25-1 sends the total sum of the digital data cumulatively added together and the count number of additions in the cumulative addition to the division block 25-2 is synchronizing with timing at which the (n+1)-th pixel clock is inputted, an area for cumulative addition of the digital data and an area for counts of additions in the cumulative addition in the cumulative addition block 25-1 are reset into their initial states respectively, and then the division block 25-2 divides the count number of additions in the cumulative addition into the total sum of the digital data cumulatively added together, the data on the total sum of the digital data cumulatively added together being sent by the cumulative addition block 25-1. As a result, it is possible to acquire an average of the detection signal acquired by cumulative addition in accordance with scanning speeds varying with pixels, as pixel values per one sampling. As a result, it is possible to remove differences between the pixels in brightness even if scanning speeds of the scanning means 11-2 vary with scanning positions. In addition, there is no useless part of the detection signal which is detected, in the laser scanning microscopic apparatus, and it becomes easy to remove noises in detection signal with high accuracy by averaging the noises contained in the detection signal. Also, even in the case where a scanning speed of the scanning means is set to become an invariable speed in the whole of a scanning range without the use of resonance phenomenon, there is no necessity that a setting of an integrated quantity of data on exposure should be changed as often as a setting of scanning speed is changed.

Also, in the laser scanning type observation apparatus (laser scanning microscope apparatus) according to each of the above-described embodiments further having such a constitution as shown in FIG. 26, it is preferred that the division block 25-2 includes a division circuit corresponding to a limited divisor.

Also, in the laser scanning type observation apparatus (laser scanning microscope apparatus) according to each of the above-described embodiments further having such a constitution as shown in FIG. 26, it is preferred that the division circuit is composed of only a combination of bit-shift circuits.

Such a configuration makes it possible to avoid a huge scale circuit.

And, in the laser scanning type observation apparatus (laser scanning microscope apparatus) according to each of the above-described embodiments further having such a constitution as shown in FIG. 26, the laser oscillation means 11 includes the laser beam source 11-1 and the galvanometer mirror 11-2 as a scanning means, as shown in FIG. 26. In addition, the laser scanning type observation apparatus (laser scanning microscope apparatus) according to each of the above-described embodiments further having such a constitution as shown in FIG. 26 further includes a pixel-position discerning circuit 26 and the pixel-clock generating means 27. Besides, the reference numeral 20' shown in FIG. 26 denotes an image displaying unit which displays a digital image on the basis of pixel values constructed by the processing unit 25.

The laser beam source 11-1 generates laser oscillation to irradiate a laser beam to the test object 30.

The galvanometer mirror 11-2 is configured to be capable of scanning irradiation points on the test object 30 to which a laser emitted by the laser beam source 11-1 is irradiated, through resonance phenomenon.

The pixel-position discerning circuit 26 discerns a change of pixel position corresponding to the irradiation point while discerning the change of pixel position is synchronizing with a change of irradiation point scanned by the galvanometer mirror 11-2, The pixel-clock generating means 27 outputs a trigger for timing of the change in pixel position which is discerned by the pixel-position discerning circuit 26, as a pixel clock.

The sampling-clock generating means 24 is set to output a plurality of sampling clocks between: the time the pixel-clock generating means 27 outputs the n-th pixel clock; and the time the pixel-clock generating means 27 outputs the (n+1)-th pixel clock.

The processing unit 25 includes the cumulative addition block 25-1 and the division block 25-2.

The cumulative addition block 25-1 is composed of a cumulative adder 25-1$a$ and a cumulative addition counter 25-1$b$, as shown in FIG. 29.

The cumulative adder 25-1$a$ cumulatively adds together digital data which are generated by a plurality of A/D conversion processes performed by the sampling means 15 (15'), between: the time the n-th pixel clock outputted by the pixel-clock generating means 27 is inputted; and the time the (n+1)-th pixel clock outputted by the pixel-clock generating means 27 is inputted a laser for irradiation to the test object 30.

The cumulative addition counter 25-1$b$ counts the number of additions in the cumulative addition of the digital data by the cumulative adder 25-1$a$.

In addition, the cumulative adder 25-1$a$ and the cumulative addition counter 25-1$b$ send to the division block 25-2 the total sum of the digital data which are cumulatively added together until the (n+1)-th pixel clock is inputted and the number of additions in the cumulative addition which is counted until the (n+1)-th pixel clock is inputted, while timing of sending the data on the total sum of the digital data cumulatively added together and the count number of additions in the cumulative addition to the division block 25-2 is synchronizing with timing at which the (n+1)-th pixel clock is inputted, and then the cumulative addition block 25-1 resets its areas for cumulatively adding the digital data together and its area for counting the number of additions in the cumulative addition into their initial states respectively.

The division block 25-2 is composed of a division circuit which performs division operation to divide the count number of additions in the cumulative addition into the total sum of the digital data cumulatively added together, the data on the total sum of the digital data cumulatively added together being sent from the cumulative addition block 25-1.

Now, a specific example of configurations for the division block 25-2 is explained using FIGS. 30 and 31.

When fractions acquired by dividing 1 by divisors 2 to 16 respectively are expressed by additions of fractions acquired by dividing 1 by powers of 2 respectively for example, the fractions acquired by dividing 1 by the divisors 2 to 16 respectively are expressed by fractions of two to the power of minus one to two to the power of minus twelve, as shown in FIG. 30. Also, positions of two to the power of minus one to two to the power of minus twelve in every fraction of the fractions acquired by dividing 1 by the divisors 2 to 16 respectively are aligned with those in the others of those fractions respectively, and the positions of two to the power of minus one to two to the power of minus twelve in each fraction are replaced with bits respectively. It is found that divisions of dividing these fractions by two correspond to a shift to the right side by one bit in binary notation.

Accordingly, resistors (bit shift circuit) which cause a shift to the right side by one bit in binary notation in an input signal are provided, and an addition is performed in a combination of these resistors in accordance with divisors. As a result, a result of division can be acquired.

In the laser scanning type observation apparatus (laser scanning microscope apparatus) according to each of the above-described embodiments further having such a constitution as shown in FIG. 26, the division block 25-2 includes resistors (bit shift circuit) S(1) to S(12) which cause a shift to the right side by one bit in binary notation respectively in an input signal, as shown in FIG. 31A, and the division block 25-2 includes a division circuit which performs addition in a set combination of the resistors S(1) to S(12) in accordance with divisors.

In the case where an input signal is a signal of 13 bits and divisors range from 2 to 16 for example, the division circuit is configured to perform addition in a proper combination of the bit shift circuits S(1) to S(12) so that a result of division can be acquired, as shown in FIG. 31B.

A procedure for calculating pixel values with data on a detection signal from pixels that are different from one another in exposure time of laser in the laser scanning type observation apparatus (laser scanning microscope apparatus) according to each of the above-described embodiments further having such a constitution as shown in FIG. 26 is explained using FIG. 32.

The sampling means 15 (15') gives a detection signal outputted by the light detecting unit 12 an A/D conversion while timing at which the A/D conversion is performed by the sampling means 15 (15') is synchronizing with oscillation of a sampling clock (operation clock) outputted by the sampling-clock generating means 24. A detection signal "Y", "Z", . . . , "J", and "K" shown in FIG. 32 denotes a detection signal acquired after the A/D conversion.

The cumulative adder 25-1a of the cumulative addition block 25-1 cumulatively adds together digital data on the detection signal after the A/D conversion performed by the sampling means 15 (15'). Also, the cumulative addition counter 25-1b of the cumulative addition block 25-1 counts the number of additions in the cumulative addition of the digital data that is performed by the cumulative adder 25-1a.

Now, it is presumed that the n-th pixel clock Sn outputted by the pixel-clock generating means 27 is inputted into the cumulative addition block 25-1. As a result, the cumulative adder 25-1a sends to the division block 25-2 a digital data on the total sum acquired by cumulatively adding the digital data on the detection signal together until the pixel clock Sn is inputted (the digital data on the total sum acquired by cumulatively adding the data on the detection signal together is " . . . +Y+Z" in an example shown in FIG. 32), and then the cumulative adder 25-1a resets its area for cumulatively adding digital data together into its initial state (for example, NULL). Also, the cumulative addition counter 25-1b sends to the division block 25-2 the data on the number of additions in the cumulative addition (the number of additions in the cumulative addition is "N" in the example shown in FIG. 32), the number of additions in the cumulative addition being counted by the cumulative addition counter 25-1b until the pixel clock Sn is inputted, and then the cumulative addition counter 25-1b resets its area for counting the number of additions in cumulative addition into its initial state (for example, "1").

The division block 25-2 performs division operation to divide the number of additions in the cumulative addition "N" into the digital data acquired by the cumulative addition " . . . Y+Z" which is sent by the cumulative addition block 25-1.

As a result, an average of the detection signal . . . , "Y", and "Z" at the pixel position, "( . . . +Y+Z)/N", is acquired as a pixel value.

Similarly, it is presumed that the (n+1)-th pixel clock Sn+1 outputted by the pixel-clock generating means 27 is inputted into the cumulative addition block 25-1. As a result, the cumulative adder 25-1a sends to the division block 25-2 a digital data on the total sum acquired by cumulatively adding digital data on the detection signal together until the pixel clock Sn+1 is inputted (the digital data on the total sum acquired by cumulatively adding the digital data on the detection signal together is "A+ . . . +G" in an example shown in FIG. 32), and then the cumulative adder 25-1 a resets its area for cumulatively adding digital data together into its initial state (for example, NULL). Also, the cumulative addition counter 25-1b sends to the division block 25-2 the number of additions in the cumulative addition (the number of additions in the cumulative addition is "7" in the example shown in FIG. 32), the number of additions in the cumulative addition being counted by the cumulative addition counter 25-1b until the pixel clock Sn+1 is inputted, and then the cumulative addition counter 25-1b resets its area for counting the number of additions in cumulative addition into its initial state (for example, "1").

The division block 25-2 performs division operation to divide the number of additions in the cumulative addition "7" into the digital data on the total sum acquired by the cumulative addition "A+ . . . +G" which is sent by the cumulative addition block 25-1.

As a result, an average of the detection signal, "A", . . . , and "G" at the pixel position, "(A+ . . . +G)/7", is acquired as a pixel value.

In this explanation, the above-described divisors stand for the number of samplings performed between the n-th pixel clock and the (n+1)-th pixel clock. Also, as shown in FIG. 28D, a clock interval between pixel clocks which determines the number of data added together is determined by scanning speed of laser spot, so that the clock interval is in a finite range as well as the number of data added together. That is to say, because the determinations of scanning speed of laser spot and of rate of sampling timing leads to the determination of range of divisors, the divisor circuit has only to be configured to perform division operation with only the limited number of divisors. Accordingly, in the laser scanning type observation apparatus (laser scanning microscope apparatus) according to each of the above-described embodiments further having such a constitution as shown in FIG. 26, the division block 25-2 includes division circuits corresponding to the limited divisors respectively and the division circuits are configured only in a combination of bit shift circuits respectively, so that it is possible to avoid huge scale circuits.

Besides, in the case where the laser scanning type observation apparatus (laser scanning microscope apparatus) according to each of the above-described embodiments further having such a constitution as shown in FIG. 26 is configured: to include an ON-OFF switching unit which switches irradiation of pulsed laser emitted by the pulsed-laser oscillation means 11 to a test object and non-irradiation of pulsed laser to the test object to each other so that detection is performed while sampling timings are being thinned; or to include a delay optical path unit (which is not shown in the drawings,) which splits an optical path of pulsed laser emitted by the pulsed-laser oscillation means 11 into at least two or more optical paths and which multiplies a frequency of the pulsed laser emitted by the pulsed-laser oscillation means 11 by a difference between the different optical paths in length to irradiate a pulsed laser with the multiplied frequency to the test object 30, so as to multiply sampling timing, it is preferred that the cumulative addition block 25-1 and the division block 25-2 which are provided for the processing unit 15 in a laser scanning microscope apparatus are configured to be capable of dealing with multiplication of and frequency division of sampling clock.

Besides, the characteristic constitutions of the laser scanning microscope apparatus which is explained using FIGS. 26 to 32 are not limited to the apparatuses which are premised on only the above-described embodiments.

As explained above, the present invention includes not only characteristics claimed in claims but also characteristics as follows.

(1) A laser scanning microscope, characterized in that the laser scanning microscope includes: a pulsed-laser oscillation means generating pulsed-laser oscillation to irradiate pulsed laser to a test object; a light detecting unit receiving light from the test object to output a detection signal; a sampling-clock generating means including a clock device and reshaping a signal for detection of oscillation of the pulsed laser from the pulsed-laser oscillation means through the clock device to output a sampling clock that synchronizes with an oscillation mode of the pulsed-laser oscillation means; and a sampling means sampling the detection signal outputted by the light detecting unit while timing at which the sampling means samples the detection signal outputted by the light detecting unit is synchronizing with the sampling clock outputted by the sampling-clock generating means, wherein the sampling-clock generating means includes a high magnification amplifier and a band pass filter, and the high magnification amplifier and the band pass filter send to the clock device a signal acquired by removing a set frequency component from the signal for the detection of the oscillation of the pulsed laser from the pulsed-laser oscillation means, the set frequency component being a component different from a oscillation frequency of the pulsed laser.

(2) A laser scanning microscope according to (1), characterized in that the clock device has a jitter-removing function.

(3) A laser scanning microscope according to (2), characterized in that the clock device has a wide output band range width.

(4) A laser scanning microscope according to (1), characterized in that the clock device is configured to consist of: a first clock device having a jitter-removing function; and a second clock device having a wide output band range width, the first and second clock devices being connected to each other in a manner of cascade connection.

(5) A laser scanning microscope according to one of (1) to (4), characterized in that an oscillation frequency of pulsed laser emitted by the pulsed-laser oscillation means is 70 MHz to 90 MHz.

(6) A laser scanning microscope according to one of (1) to (5), characterized in that a transmission band range of the band pass filter is approximately 10 KHz to a frequency 1.2 times the oscillation frequency.

(7) A laser scanning microscope according to one of (1) to (6), characterized in that the sampling-clock generating means includes: a plurality of pairs of high magnification amplifier and band pass filter, the pairs of high magnification amplifier and band pass filter being made in such a way that high magnification amplifiers are paired with band pass filters respectively so that the pairs of high magnification amplifier and band pass filter are made to differ from one another in magnification and in transmission band range so as to be capable of dealing with noise levels of signals for detection of oscillation of pulsed laser from the pulsed-laser oscillation means, and the pairs of high magnification amplifier and band pass filter being arranged to be in a multi-stage arrangement; and the switch element which switches conductive paths of a signal for detection of oscillation of pulsed laser from the pulsed-laser oscillation means to one another so as to transmit the signal for detection of oscillation of pulsed laser through a pair of high magnification amplifier and band pass filter having optimum magnification and optimum transmission band range for the signal for detection of oscillation of pulsed laser, in accordance with a noise level of the signal for detection of oscillation of pulsed laser.

(8) A laser scanning microscope according to one of (1) to (7), characterized in that the sampling-clock generating means further includes: a clock means having a PLL function so that the clock means converts a signal for detection of oscillation of pulsed laser from the pulsed-laser oscillation means into a clock signal; and a frequency-range setting means capable of automatically setting a range of frequency tracked by the PLL function and capable of automatically changing a setting of the range of frequency, to the clock means having the PLL function.

(9) A laser scanning microscope according to (8), characterized in that the sampling-clock generating means further includes: a locked-state detecting means which detects the locked state of the clock means with the PPL function; a frequency-range sweeping means which sweeps a set range of frequency in increments of a set frequency to change a range of frequency capable of being tracked by the PLL function to another one, the range of frequency capable of being tracked by the PPL function being given to the clock means having the PLL function as a setting through the frequency-range setting means; and a locked-state examination control means which ends: the sweep performed by the frequency-range sweeping means; and a setting of a new range of frequency to be tracked and the change of a setting of range of frequency to be tracked that are performed by the frequency-range setting means when the locked-state detecting means detects the locked state of the clock means with the PLL function while the clock means with the PLL function is tracking a range of frequency tracked by the PLL function to which a range of frequency was changed by the frequency-range setting means after a set frequency range is swept by the frequency-range sweeping means.

(10) A laser scanning microscope according to (8) or (9), characterized in that the locked-state examination control means makes the frequency-range setting means automatically make a re-setting of a range of frequency to be tracked by the PLL function which was given to the clock means with the PLL function as a setting, on the basis of a frequency at the time the locked-state detecting means detected the locked state of the clock means having the PLL function, when the locked-state detecting means detects the unlocked state of the clock means having the PLL function after having detected the locked state of the clock means having the PLL function.

(11) A laser scanning microscope according to one of (8) to (10), characterized in that the frequency-range setting means can give a setting of frequency to the clock means having the PLL function and can change a setting of frequency, in a range from 70 MHz to 100 MHz.

(12) A laser scanning microscope according to one of (8) to (11), characterized in that the frequency-range sweeping means sweeps a frequency range of ±10 MHz in increments of 1 KHz.

(13) A laser scanning microscope apparatus, characterized in that the laser scanning microscope apparatus includes: a laser oscillation means which includes a laser beam source generating laser oscillation to irradiate laser to a test object and a scanning means capable of scanning an irradiation point of the test object to which the laser emitted by the laser beam source is irradiated through resonance phenomenon; a light detecting unit which receives light from the test object to output a detection signal; a pixel-position change discerning means which discerns a change in pixel position corresponding to an irradiation point while discerning the change in pixel position corresponding to the irradiation point is synchronizing with a change in the irradiation point scanned by the scanning means; a pixel-clock generating means which outputs a trigger for timing of the change in pixel position which is discerned by the pixel-position change discerning means, as a pixel clock; a sampling-clock generating means which outputs a sampling clock; a sampling means which gives the detection signal detected by the light-detecting unit A/D conversion while timing at which the A/D conversion is performed by the sampling means is synchronizing with the sampling clock outputted by the sampling-clock generating means; and an processing unit which outputs a signal value for forming an image with the detection signal which is given the A/D conversion by the sampling means, wherein: the sampling-clock generating means outputs sampling clocks many times until the pixel-clock generating means outputs the n+1-th pixel clock after having outputted the n-th pixel clock; the processing means includes a cumulative addition block and a division block; the cumulative addition block cumulatively adds digital data generated by the sampling means performing a plurality of A/D conversions together between the time the n-th pixel clock outputted by the pixel-clock generating means is inputted and the time the n+1-th pixel clock outputted by the pixel-clock generating means is inputted, while the cumulative addition block is counting the number of additions in the cumulative addition, the cumulative addition block sends to the division block data on the total sum of the digital data cumulatively added together and the counted number of additions in the cumulative addition until the (n+1)-th pixel clock is inputted, while timing at which data on the total sum of the digital data cumulatively added together and the number of additions in the cumulative addition are sent to the division block is synchronizing with timing of the input of the (n+1)-th pixel clock, and then the cumulative addition block resets its areas for cumulatively adding digital data together and for counting the number of additions in the cumulative addition into initial states of the areas respectively; and the division block performs a division operation to divide the number of additions in the cumulative addition into the total sum of the digital data cumulatively added together, the total sum of the digital data cumulatively added together being sent by the cumulative addition block.

(14) A laser scanning microscope apparatus according to (13), characterized in that the division block includes a division circuit corresponding to a limited divisor.

(15) A laser scanning microscope apparatus according to (14), characterized in that the division circuit is composed of only a combination of bit-shift circuits.

A laser scanning type observation apparatus according to the present invention is useful for every field which requires processes of irradiating pulsed laser to a test object, of detecting returning light from the test object, and of forming an image by using the detected intensity of the retuning light as a pixel value, such as laser scanning microscopes and laser scanning endoscopes, for example.

What is claimed is:

1. A laser scanning type observation apparatus comprising
   a pulsed-laser oscillation means generating pulsed-laser oscillation to irradiate a pulsed laser beam to a test object,
   a light detecting unit receiving light from the test object to output a detection signal,
   a synchronous signal generating means detecting oscillation of pulsed laser from the pulsed-laser oscillation means to output a synchronous signal that is made to synchronize with the oscillation of the pulsed laser beam,
   a delay circuit unit delaying the synchronous signal outputted by the synchronous signal generating means for an optional amount of time, to output a trigger signal,
   a sampling means sampling the detection signal outputted by the light detecting unit while the sampling of the detection signal by the sampling means is being made to synchronize with the trigger signal outputted by the delay circuit unit, and
   a memory unit storing the detection signal sampled by the sampling means,
   the laser scanning type observation apparatus further comprising
   a multi-stage delay setting unit capable of setting delay time for delaying the synchronous signal by the delay circuit unit in at least two or more stages within one period of the synchronous signal, and
   a decision unit determining an optimum delay stage for image formation using data on intensities of the detection signal at the respective delay stages, the detection signal at the respective delay stages being sampled by the sampling means while the sampling of the detection signal at the respective delay stages by the sampling means is being made to synchronize with a trigger signal outputted by the delay circuit unit in accordance with the two or more stages of delay time set by the multi-stage delay setting unit and then the data on the intensities of the detection signal at the respective delay stages being stored in the memory unit,
   the multi-stage delay setting unit setting delay time for which the synchronous signal is delayed by the delay circuit unit, to delay time corresponding to the optimum delay stage for image formation which is determined by the decision unit, and
   the multi-stage delay setting unit fixing delay time for which the synchronous signal is delayed by the delay circuit unit, at delay time corresponding to the optimum delay stage for image formation, so as to be capable of performing observation.

2. The laser scanning type observation apparatus according to claim 1, wherein the decision unit decides on a delay stage at which the detection signal has the largest intensity of the intensities of the detection signal at the respective delay stages which are stored in the memory unit as data, as an optimum delay stage for image formation.

3. The laser scanning type observation apparatus according to claim 1, wherein the laser scanning type observation apparatus further comprises a delay setting switch through which the multi-stage delay setting unit and the decision unit are made to set delay time corresponding to an optimum delay stage for image formation afresh.

4. The laser scanning type observation apparatus according to claim 1, wherein
   the laser scanning type observation apparatus further comprises an ON-OFF switching unit which switches an on-operation of irradiation and an off-operation of irradiation to each other, the on-operation of irradiation causing irradiation of a pulsed laser beam generated by the pulsed-laser oscillation means to the test object and the off-operation of irradiation causing a stop of irradiation of a pulsed laser beam generated by the pulsed-laser oscillation means to the test object, and
   the decision unit determines an optimum delay stage for image formation, using data on intensities of the detection signal at the respective delay stages which are set by the to multi-stage delay setting unit when the on-operation of irradiation or the off-operation of irradiation is performed by the ON-OFF switching unit.

5. The laser scanning type observation apparatus according to claim 4, wherein the decision unit further calculates a value of contrast of the detection signal, using the data on the intensities of the detection signal at the respective delay stages which are set by the multi-stage delay setting unit when the on-operation of irradiation or the off-operation of irradiation is performed by the ON-OFF switching unit.

6. The laser scanning type observation apparatus according to claim 4, wherein the decision unit further detects background noise, using the data on the intensities of the detection signal at the respective delay stages which are set by the multi-stage delay setting unit when the off-operation of irradiation is performed by the ON-OFF switching unit.

7. The laser scanning type observation apparatus according to claim 4, wherein
   the laser scanning type observation apparatus further comprises a delay optical path unit which splits an optical path of a pulsed laser emitted by the pulsed-laser oscillation means into at least two or more optical paths and which multiplies a period of the pulsed laser emitted by the pulsed-laser oscillation means due to a difference between the different optical paths in length to irradiate a pulsed laser with the multiplied period to the test object, the ON-OFF switching unit is placed on at least one of the optical paths into which the optical path of the pulsed laser emitted by the pulsed-laser oscillation means is split by the delay optical path unit, and the ON-OFF switching unit switches from the on-operation of irradiation and the off-operation of irradiation to each other within one period of oscillation of the pulsed laser emitted by the pulsed-laser oscillation means.

8. The laser scanning type observation apparatus according to claim 1, wherein the synchronous signal generating means and the delay circuit unit constitute a sampling-clock generating means which outputs a sampling clock using a signal for detection of oscillation of pulsed laser from the pulsed-laser oscillation means, the sampling clock being made to synchronize with an oscillation mode of the pulsed-laser oscillation means, the laser scanning type observation apparatus further comprises an AC-coupled amplifier which amplifies the detection signal outputted by the light detecting unit to output the amplified signal, the sampling means samples the detection signal which is amplified to be outputted by the AC-coupled amplifier while the sampling of the detection signal by the sampling means is being made to synchronize with the sampling clock outputted by the sampling-clock generating means, the laser scanning type observation apparatus further comprises a processing unit which outputs a signal value for image formation with the detection signal that is sampled by the sampling means, the sampling means includes an AD converter means of two systems, and the processing unit includes a delay setting means and a difference calculating unit, the delay setting means consisting of the memory unit and the decision unit, the memory unit storing the detection signal sampled by the sampling means, the delay setting means being capable of adjusting and setting an amount of a delay of timing at which the detection signal is sampled by each of the two systems of the AD converter means, relative to each of the two systems, and the difference calculating unit outputting a difference between detection signals from the AD converter means of two systems as a signal value for image formation, the detection signals from the AD converter means of two systems being sampled at the timings set by the delay setting means.

9. The laser scanning type observation apparatus according to claim 8, wherein the delay setting means adjusts amounts of delays of timings at which the detection signal is sampled by two systems of the AD converter means respectively, to make the amounts of the delays of the timings differ from each other by a half period of the oscillation frequency of the pulsed laser.

10. The laser scanning type observation apparatus according to claim 8, wherein the delay setting means adjusts an amount of a delay of timing at which the detection signal is sampled by a first system of the AD converter means of two systems so that a detection signal from the first system of the AD converter means has the maximum value, and the delay setting means adjusts an amount of a delay of timing at which the detection signal is sampled by a second system of the AD converter means of two systems so that a detection signal from the second system of the AD converter means has the minimum value.

\* \* \* \* \*